United States Patent [19]
Bayer et al.

[11] Patent Number: 6,063,813
[45] Date of Patent: May 16, 2000

[54] CYANIMINO OXIME ETHERS, PROCESS AND INTERMEDIATES FOR THE PREPARATION AND USE THEREOF FOR THE CONTROL OF NOXIOUS FUNGI AND ANIMAL PESTS

[75] Inventors: Herbert Bayer, Mannheim; Ruth Müller, Friedelsheim; Hubert Sauter, Mannheim; Wassilios Grammenos, Ludwigshafen; Thomas Grote, Schifferstadt; Reinhard Kirstgen, Neustadt; Bernd Müller, Frankenthal; Klaus Oberdorf, Heidelberg; Franz Röhl, Schifferstadt; Eberhard Ammermann, Heppenheim; Volker Harries, Frankenthal; Gisela Lorenz, Hambach; Siegfried Strathmann, Limburgerhof, all of Germany

[73] Assignee: BASF Aktiengesellschaft, Ludwigshafen, Germany

[21] Appl. No.: 09/091,850

[22] PCT Filed: Dec. 16, 1996

[86] PCT No.: PCT/EP96/05641

§ 371 Date: Jun. 25, 1998

§ 102(e) Date: Jun. 25, 1998

[87] PCT Pub. No.: WO97/24319

PCT Pub. Date: Jul. 10, 1997

[30] Foreign Application Priority Data

Dec. 27, 1995 [DE] Germany ............. 195 48 783

[51] Int. Cl.[7] ............ A01N 37/02; A01N 37/12; C07C 255/03; C07C 251/32
[52] U.S. Cl. ............ 514/506; 514/567; 514/538; 514/620; 558/391; 560/22; 562/440; 564/164; 564/265
[58] Field of Search ............... 558/391; 564/265, 564/164; 560/22; 562/440; 514/506, 538, 567, 620

[56] References Cited

FOREIGN PATENT DOCUMENTS

93/16986 9/1993 WIPO .
95/18789 7/1995 WIPO .

Primary Examiner—Joseph McKane
Assistant Examiner—Ebenezer Sackey
Attorney, Agent, or Firm—Keil & Weinkauf

[57] ABSTRACT

Cyanoiminooxime ethers of the formula I

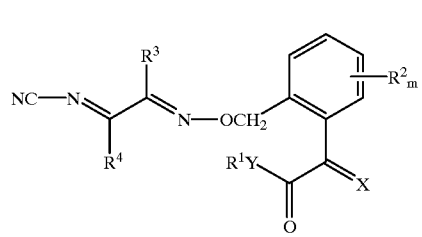

(I)

wherein

X is $NOCH_3$, $CHOCH_3$ or $CHCH_3$;

Y is O or NZ where Z is hydrogen or alkyl;

$R^1$ is hydrogen or $C_1$–$C_4$-alkyl;

$R^2$ is cyano, nitro, halogen, alkyl, trifluoromethyl or alkoxy;

m is 0, 1 or 2;

$R^3$ is hydrogen, cyano, alkyl, haloalkyl, alkoxy or cycloalkyl;

$R^4$ is hydrogen, or unsubstituted or substituted alkyl, alkenyl, alkynyl, cycloalkyl, cycloalkenyl, heterocyclyl, aryl or hetaryl, or a salt thereof, their preparation, intermediates for their preparation, and their use for controlling harmful fungi and animal pests.

12 Claims, No Drawings

CYANIMINO OXIME ETHERS, PROCESS AND INTERMEDIATES FOR THE PREPARATION AND USE THEREOF FOR THE CONTROL OF NOXIOUS FUNGI AND ANIMAL PESTS

This application is a 371 of PCT/EP96/05641 filed on Dec. 16, 1996.

The present invention relates to cyanoiminooxime ethers of the formula I

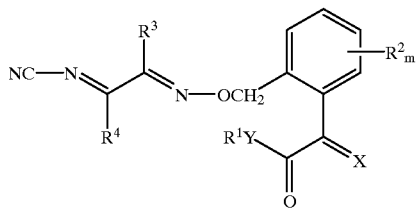

(I)

where the variables have the following meanings:

X is $NOCH_3$, $CHOCH_3$ or $CHCH_3$;

Y is O or NZ where Z is hydrogen or $C_1$–$C_4$-alkyl;

$R^1$ is hydrogen or $C_1$–$C_4$-alkyl;

$R^2$ is cyano, nitro, halogen, $C_1$–$C_4$-alkyl, trifluoromethyl or $C_1$–$C_4$-alkoxy;

m is 0, 1 or 2, it being possible for the radicals $R^2$ to be different when m is 2;

$R^3$ is hydrogen, cyano, alkyl, haloalkyl, alkoxy or cycloalkyl;

$R^4$ is hydrogen or unsubstituted or substituted: alkyl, alkenyl, alkynyl, cycloalkyl, cycloalkenyl, heterocyclyl, aryl or hetaryl, and to salts thereof.

Furthermore, the invention relates to processes and intermediates for the preparation of these compounds, to compositions comprising them, and to the use of the compounds I for controlling animal pests and harmful fungi.

Cyanoiminooxime ethers of the formula I which are fungicidally and insecticidally active have been disclosed in the following publications: WO-A 95/18789 and WO-A 93/16986. However, the active ingredients disclosed in these publications are not yet satisfactory with regard to their activity.

It is an object of the present invention to provide novel compounds with an improved activity against harmful fungi and pests.

We have found that this object is achieved by the cyanoiminooxime ethers I defined at the outset. Furthermore, we have found processes and intermediates for their preparation, compositions comprising them for controlling animal pests and harmful fungi, and the use of the compounds I for this purpose.

The compounds I are obtainable by various routes following processes known per se.

In principle, it is irrelevant when synthesizing the compounds I whether the group —C(X)—CO—$YR^1$ or the group —$CH_2ON$=C($R^3$)—C($R^4$)=N—CN is constructed first.

The construction of the group —C(X)—CO—$YR^1$ has been disclosed, for example, in the following publications: EP-A 422 597, EP-A 463 488, EP-A 370 629, EP-A 460 575, EP-A 472 300, WO-A 90/07493, WO-A 92/13830, WO-A 92/18487, DE Appl. P 44 20 416.7.

In the descriptions of syntheses below, "Houben-Weyl" means: Houben-Weyl, Methoden der Organischen Chemie [methods in Organic Chemistry], Georg Thieme verlag, Stuttgart.

1.1 When constructing the group —$CH_2ON$=C ($R^3$)—C ($R^4$)=N—CN, a procedure is generally followed in which a benzyl derivative of the formula II is reacted with a hydroxyimine of the formula III.

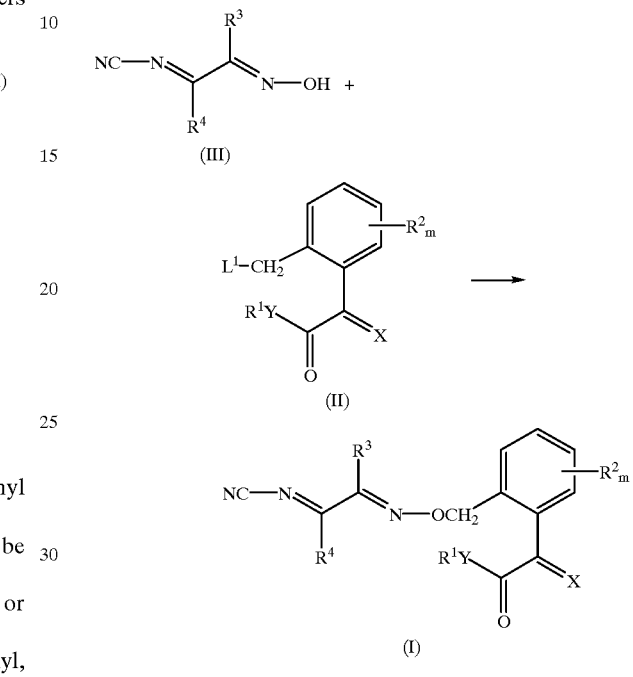

$L^1$ in formula II is a nucleophilically exchangeable leaving group, e.g. halogen or a sulfonate group, preferably chlorine, bromine, iodine, mesylate, tosylate or triflate.

The reaction is carried out in a manner known per se in an inert organic solvent in the presence of a base, e.g. sodium hydride, potassium hydroxide, potassium carbonate or triethylamine, following methods known from the literature (cf. Houben-Weyl, 4th Edition, Vol. E 14b, p. 370 et seq. and Vol. 10/1, p. 1189 et seq.).

1.2 The hydroxyimines III are obtained, for example, by reacting a carbonylhydroxyimino derivative IV with bis(trimethylsilyl)carbodiimide.

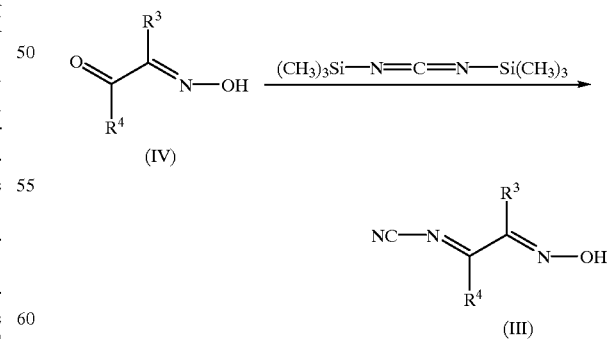

The reaction is carried out in a manner known per se in an inert organic solvent, preferably with fluoride or cyanide catalysis or in the presence of Lewis acids such as titanium tetrachloride (Liebigs Ann. Chem. 1986, page 142 et seq.; Angew. Chemie 96, 1984, page 437 et seq.).

Occasionally, it may be advantageous prior to the reaction to provide the oxime function of IV by generally known methods with a protective group, e.g. an acyl group (alkylcarbonyl group) or a sulfonyl group, which can be reeliminated at a later point in time. This protective-group technology can also be applied to nucleophilic centers in the radical $R^4$.

The carbonylhydroxyimino derivatives IV which have not already been disclosed can be prepared by methods known per se (cf. Org. Synth. 16, 1936, page 46; Bull. Chem. Soc. Jap. 44, 1971, page 219 et seq.; DE-A-27 22 416; Gazz. Chim. Ital. 61, 1931, page 943 et seq.; Chem. Ber 106, 1973 page 1688 et seq.).

2. Alternatively, the compounds I can also be obtained by first reacting the benzyl derivative II with the carbonylhydroxyimino derivative IV to give a corresponding benzyl oxime of the formula V and subsequently to react V with bis(trimethylsilyl)carbodiimide to give I.

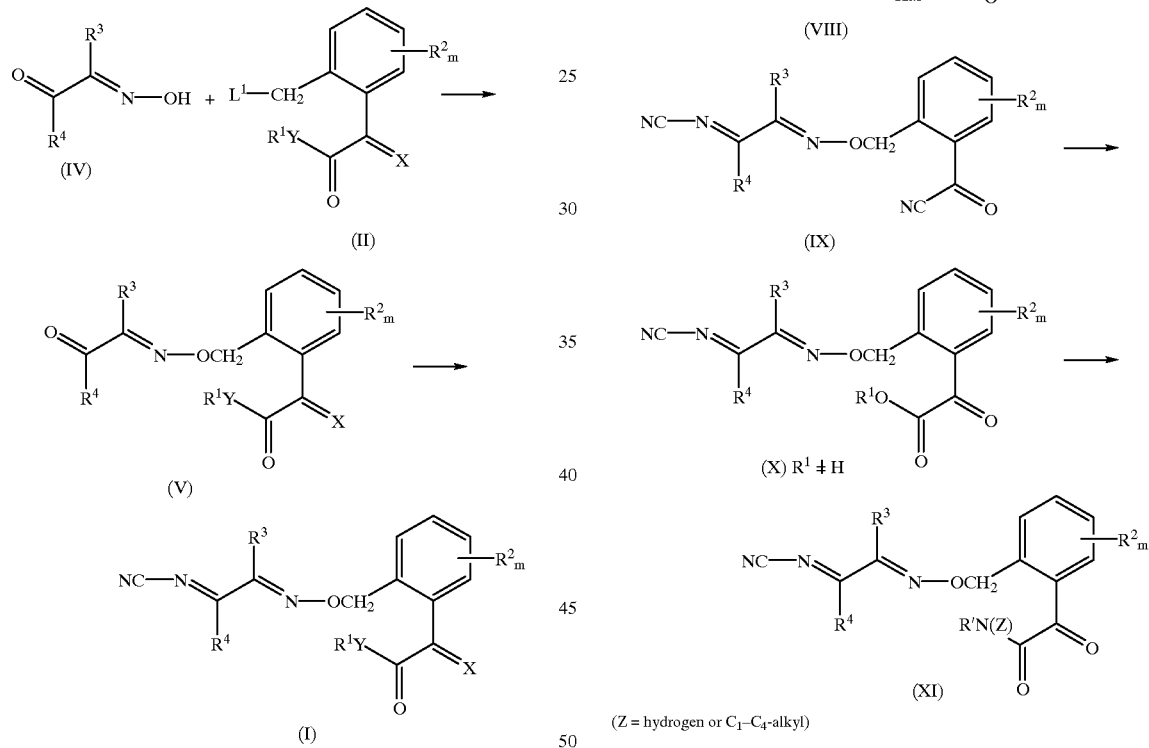

The reaction of IV with II is carried out by a method similar to the synthesis described below for 1.1. The reaction of V with bis(trimethylsilyl)carbodiimide is carried out by a method similar to the synthesis described below under 1.2.

3. Furthermore, the compounds I are obtained by first converting a compound III with a lactan VI as described in EP-A 493 711 to give the corresponding benzoic acid VII and converting VII via the corresponding halides VIII into the cyanocarboxylic acids IX, which are converted into the α-keto esters X via a Pinner-reaction (Angew. Chem. 94, page 1, 1982) and, if desired, further to give the α-ketoamides XI (cf. EP-A 348 766, DE-A 37 05 389, EP-A 178 826, DE-A 36 23 921, Houben-Weyl, 4th Edition, Vol. E5, p. 941 et seq.).

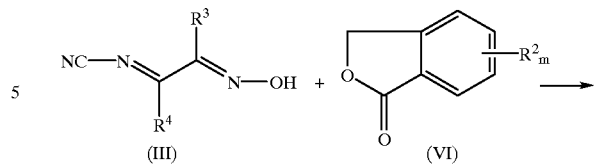
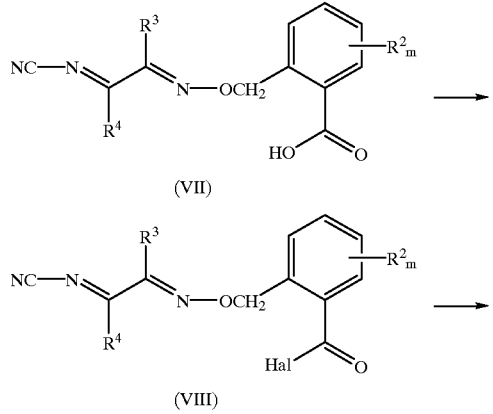
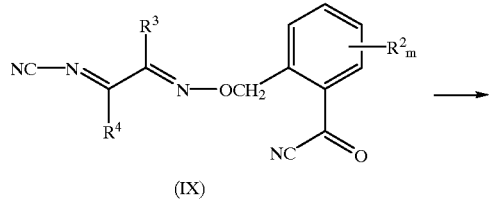
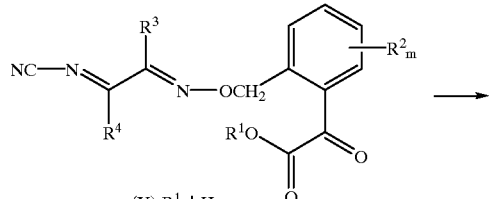
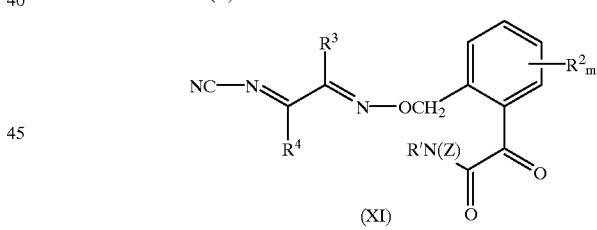

(Z = hydrogen or $C_1$–$C_4$-alkyl)

The α-keto esters X and the α-ketoamides XI can be converted into the compounds I following customary processes (cf. EP-A 178 826, EP-A 348 766, DE-A 36 23 921, DE-A 37 05 389 and the references cited at the outset.

Compounds I where $R^1$ is hydrogen are obtained by hydrolyzing the esters X and subsequently reacting the product to give I.

The compounds I where Y is NZ can also be obtained from the esters (Y=O) by reacting them with the corresponding amines $HN(Z)^1$. Those compounds II which have not already been disclosed in EP-A 513 580, EP-A 477 631, EP-A 463 488, EP-A 251 082, EP-A 400 417 and/or EP-A 585 751 can be prepared by the methods described therein.

Due to their C=C and C=N double bonds, the compounds I can be obtained, upon preparation, as E/Z isomer mixtures which can be separated into the individual compounds in the customary manner, for example by crystallization or chromatography.

If, upon synthesis, isomer mixtures are obtained, separation of the isomers is, however, generally not absolutely necessary since some of the individual isomers can be converted into each other during formulation for use, or upon use (e.g. when exposed to light, acids or bases). Corresponding conversions can also take place after use, for example in the case of the treatment of plants in the treated plant or in the harmful fungus or animal pest to be controlled.

Regarding the C=X double bond, the E isomers of the compounds I are preferred with a view to their activity (configuration based on the —OCH$_3$, or the —CH$_3$, group relative to the —COYR$^1$ group).

With regard to the —C(R$^3$)=NOCH$_2$— double bond, the cis isomers of the compounds I are preferred with a view to their activity (the radical R$^3$ and the —OCH$_2$— group are on the same side of the double bond).

The invention also embraces the acid-resisting salts of the compounds I which contain basic centers, above all basic nitrogen atoms, in particular with mineral acids such as sulfuric acid and phosphoric acid or Lewis acids such as zinc chloride. The type of salt is normally of no importance in this context. Preferred for the purposes of the invention are those salts which do not damage the plants, areas, materials or spaces to be kept free from harmful fungi or animal pests and which do not adversely affect the activity of the compounds I. Especially important are those salts which are suitable for agricultural purposes.

The salts of the compounds I are accessible in a manner known per se, above all by reacting the corresponding compound I with the abovementioned acids in water or in an inert organic solvent at from −80 to 120° C., preferably 0 to 60° C.

Collective terms which generally represent the groups below were used in the definitions of the compounds I given at the outset:

Halogen: fluorine, chlorine, bromine and iodine;

Alkyl: straight-chain or branched alkyl groups having 1 to 4, 6 or 10 carbon atoms, e.g. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylamino: an amino group which has attached to it a straight-chain or branched alkyl group having 1 to 6 carbon atoms as mentioned above;

Dialkylamino: an amino group which has attached to it two independent straight-chain or branched alkyl groups having in each case 1 to 6 carbon atoms as mentioned above;

Alkylcarbonyl: straight-chain or branched alkyl groups having 1 to 10 carbon atoms which are bonded to the skeleton via a carbonyl group (—CO—);

Alkylsulfonyl: straight-chain or branched alkyl groups having 1 to 6 or 10 carbon atoms which are bonded to the skeleton via a sulfonyl group (—SO$_2$—);

Alkylsulfoxyl: straight-chain or branched alkyl groups having 1 to 6 carbon atoms which are bonded to the skeleton via a sulfoxyl group (—S(=O)—);

Alkylaminocarbonyl: alkylamino groups having 1 to 6 carbon atoms as mentioned above which are bonded to the skeleton via a carbonyl group (—CO—);

Dialkylaminocarbonyl: dialkylamino groups having in each case 1 to 6 carbon atoms per alkyl radical as mentioned above which are bonded to the skeleton via a carbonyl group (—CO—);

Alkylaminothiocarbonyl: alkylamino groups having 1 to 6 carbon atoms as mentioned above which are bonded to the skeleton via a thiocarbonyl group (—CS—);

Dialkylaminothiocarbonyl: dialkylamino groups having in each case 1 to 6 carbon atoms per alkyl radical as mentioned above which are bonded to the skeleton via a thiocarbonyl group (—CS—);

Haloalkyl: straight-chain or branched alkyl groups having 1 to 6 carbon atoms, it being possible for some or all of the hydrogen atoms in these groups to be replaced by halogen atoms as mentioned above, e.g. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 or 6 carbon atoms as mentioned above which are bonded to the skeleton via an oxygen atom (—O—), e.g. $C_1$–$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl- 2-methylpropyloxy;

Alkoxycarbonyl: straight-chain or branched alkyl groups having 1 to 6 carbon atoms which are bonded to the skeleton via an oxycarbonyl group (—OC(=O)—);

Alkylenedioxy: e.g. $C_1$–$C_4$-alkylenedioxy: straight-chain or branched alkylene groups having 1 to 4 carbon atoms which are incorporated into the skeleton, or bonded to the skeleton, in two places via in each case one oxygen atom (—O—), such as methylenedioxy (—O—CH$_2$—O—) or 2,2-propylenedioxy (—O—C(CH$_3$)$_2$—O—);

Haloalkoxy: straight-chain or branched alkyl groups having 1 to 6 carbon atoms, it being possible for some or all of the hydrogen atoms in these groups to be replaced by halogen atoms as mentioned above and these groups being bonded to the skeleton via an oxygen atom;

Alkylthio: straight-chain or branched alkyl groups having 1 to 4 or 6 carbon atoms as mentioned above which are bonded to the skeleton via a sulfur atom (—S—), e.g. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Cycloalkyl: monocyclic alkyl groups having 3 to 6 carbon ring members, e.g. cyclopropyl, cyclobutyl, cyclopentyl and cyclohexyl;

Alkenyl: straight-chain or branched alkenyl groups having 2 to 6 or 10 carbon atoms and a double bond in any position, e.g. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl groups having 2 to 6 carbon atoms and a double bond in any position which are bonded to the skeleton via an oxygen atom (—O—);

Alkenylthio or alkenylamino: straight-chain or branched alkenyl groups having 2 to 6 carbon atoms and a double bond in any position which are bonded to the skeleton via a sulfur atom (alkenylthio) or via a nitrogen atom (alkenylamino);

Alkenylcarbonyl: straight-chain or branched alkenyl groups having 2 to 10 carbon atoms and a double bond in any position which are bonded to the skeleton via a carbonyl group (—CO—);

Alkynyl: straight-chain or branched alkynyl groups having 2 to 10 carbon atoms and a triple bond in any position, e.g. $C_2$–$C_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl- 3-butynyl, 1-ethyl-2-butynyl, 1-ethyl-3-butynyl, 2-ethyl-3-butynyl and 1-ethyl-1-methyl-2-propynyl;

Alkynyloxy, alkynylthio and alkynylamino: straight-chain or branched alkynyl groups having 2 to 6 carbon atoms and a triple bond in any position which are bonded to the skeleton via an oxygen atom (alkynyloxy) or via a sulfur atom (alkynylthio) or via a nitrogen atom (alkynylamino);

Alkynycarbonyl: straight-chain or branched alkynyl groups having 3 to 10 carbon atoms and a triple bond in any position which are bonded to the skeleton via a carbonyl group (—CO—);

Cycloalkenyl: cycloalkenyloxy, cycloalkenylthio and cycloalkenylamino: monocyclic alkenyl groups having 3 to 6 carbon ring members which are bonded to the skeleton directly, or via an oxygen atom (cycloalkenyloxy) or via a sulfur atom (cycloalkenylthio) or via a nitrogen atom (cycloalkenylamino), e.g. cyclopropenyl, cyclobutenyl, cyclopentenyl or cyclohexenyl;

Cycloalkyloxy, cycloalkylthio and cycloalkylamino: monocyclic alkyl groups having 3 to 6 carbon ring members which are bonded to the skeleton via an oxygen atom (cycloalkyloxy), via a sulfur atom (cycloalkylthio) or via a nitrogen atom (cycloalkylamino), e.g. cyclopropyl, cyclobutyl, cyclopentyl or cyclohexyl;

Heterocyclyl, heterocyclyloxy, heterocyclylthio and heterocyclylamino: three- to six-membered saturated or partially unsaturated mono- or polycyclic heterocycles which contain one to three hetero atoms selected from a group consisting of oxygen, nitrogen and sulfur and which are bonded to the skeleton directly, or via an oxygen atom (heterocyclyloxy) or via a sulfur atom (heterocyclylthio) or via a nitrogen atom (heterocyclylamino), e.g. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydro-fur-4-yl, 2,3-dihydro-fur-5-yl, 2,5-dihydro-fur-2-yl, 2,5-dihydro-fur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5- dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl;

Aryl: aryloxy, arylthio, arylcarbonyl and arylsulfonyl: aromatic mono- or polycyclic hydrocarbon radicals which are bonded to the skeleton directly, or (aryloxy) via an oxygen atom (—O—), or (arylthio) via a sulfur atom (—S—) or (arylcarbonyl) via a carbonyl group (—CO—) or (arylsulfonyl) via a sulfonyl group (—SO$_2$—), e.g. phenyl, naphthyl and phenanthrenyl, or phenyloxy, naphthyloxy and phenanthrenyloxy and the corresponding carbonyl and sulfonyl radicals;

Arylamino: aromatic mono- or polycyclic hydrocarbon radicals which are bonded to the skeleton via a nitrogen atom;

Hetaryl: hetaryloxy, hetarylthio, hetarylcarbonyl and hetarylsulfonyl: aromatic mono- or polycyclic radicals which, besides carbon ring members, additionally contain one to four nitrogen atoms or one to three nitrogen atoms and an oxygen or a sulfur atom or an oxygen or a sulfur atom and which are bonded to the skeleton directly, or (hetaryloxy) via an oxygen atom (—O—) or (hetarylthio) via a sulfur atom (—S—) or (hetarylcarbonyl) via a carbonyl group (—CO—) or (hetarylsulfonyl) via a sulfonyl group (—SO$_2$—), e.g.

5-membered hetaryl containing one to three nitrogen atoms: 5-membered hetaryl ring groups which, besides carbon atoms, can contain one to three nitrogen atoms as ring members, e.g. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl, containing one to four nitrogen atoms or one to three nitrogen atoms and a sulfur or oxygen atom or an oxygen or a sulfur atom: 5-membered hetaryl ring groups which, besides carbon atoms, can contain one to four nitrogen atoms or one to three nitrogen atoms and a sulfur or oxygen atom or an oxygen or sulfur atom as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl, containing one to three nitrogen atoms or a nitrogen atom and/or an oxygen or sulfur atom: 5-membered hetaryl ring groups which, besides carbon atoms, can contain one to four nitrogen atoms or one to three nitrogen atoms and a sulfur or oxygen atom or an oxygen or a sulfur atom as ring members and in which two adjacent carbon ring members or a nitrogen and an adjacent carbon ring member can be bridged by a buta-1,3-diene-1,4-diyl group;

5-membered hetaryl bonded via nitrogen and containing one to four nitrogen atoms, or benzo-fused 5-membered hetaryl, bonded via nitrogen and containing one to three nitrogen atoms: 5-membered hetaryl ring groups which, besides carbon atoms, can contain one to four nitrogen atoms, or one to three nitrogen atoms, as ring members and in which two adjacent carbon ring members or a nitrogen and an adjacent carbon ring member can be bridged by a buta-1,3-diene-1,4-diyl group, these rings being bonded to the skeleton via one of the nitrogen ring members;

6-membered hetaryl, containing one to three, or one to four, nitrogen atoms: 6-membered hetaryl ring groups which, besides carbon atoms, can contain one to three, or one to four, nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl, containing one to four nitrogen atoms: 6-membered hetaryl ring groups in which two adjacent carbon ring members can be bridged by a buta-1,3-diene-1,4-diyl group, e.g. quinoline, isoquinoline, quinazoline and quinoxaline, and the corresponding oxy, thio, carbonyl or sulfonyl groups.

Hetarylamino: aromatic mono- or polycyclic radicals which, besides carbon ring members, can additionally contain one to four nitrogen atoms or one to three nitrogen atoms and an oxygen or sulfur atom and which are bonded to the skeleton via a nitrogen atom.

The term "partially or fully halogenated" is intended to express that in groups thus characterized some or all of the hydrogen atoms can be replaced by identical or different halogen atoms as mentioned above.

The term "unsubstituted or substituted" is intended to express that in groups thus characterized some or all of the hydrogen atoms can be replaced by identical or different groups, for example those which have been mentioned amongst the collective terms explained above.

Preferred compounds of the formula I with a view to their biological activity are those where the variables have the following meanings:

X is $NOCH_3$, $CHOCH_3$ or $CHCH_3$;

Y is O or NZ, Z being hydrogen or $C_1$–$C_4$-alkyl;

$R^1$ is hydrogen or $C_1$–$C_4$-alkyl;

$R^2$ is cyano, nitro, halogen, $C_1$–$C_4$-alkyl, trifluoromethyl or $C_1$–$C_4$-alkoxy;

m is 0, 1 or 2, it being possible for the radicals $R^2$ to be different when m is 2;

$R^3$ is hydrogen, cyano, $C_1$–$C_4$-alkyl, $C_1$–$C_4$-haloalkyl, $C_1$–$C_4$-alkoxy, cyclopropyl;

$R^4$ is hydrogen;

$C_1$–$C_6$-alkyl, $C_2$–$C_6$-alkenyl, $C_2$–$C_6$-alkynyl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio and hetaryl-$C_1$–$C_4$-alkylthio, it being possible for the cyclic groups, in turn, to be partially or fully halogenated and/or to have attached to them one to three of the following substituents: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio, $C_3$–$C_6$-alkynyloxy, $C_1$–$C_4$-alkylenedioxy which can be halogenated, and $C(=NOR^5)$-$A_n$-$R_6$, A being oxygen, sulfur or nitrogen, the nitrogen having attached to it hydrogen or $C_1$–$C_6$-alkyl, n being 0 or 1, $R^5$ being hydrogen or $C_1$–$C_6$-alkyl and $R^6$ being hydrogen or $C_1$–$C_6$-alkyl;

$C_3$–$C_6$-cycloalkyl, $C_3$–$C_6$-cycloalkenyl, heterocyclyl, it being possible for these radicals to be partially or fully halogenated and/or to have attached to them one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio;

aryl or hetaryl, it being possible for these radicals to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio, $C_3$–$C_6$-alkynyloxy, $C_1$–$C_4$-alkylenedioxy which can be halogenated, and $C(=NOR^5)$—$A_n$—$R^6$, A being oxygen, sulfur or nitrogen and the nitrogen having attached to it hydrogen or $C_1$–$C_6$-alkyl, n being 0 or 1, $R^5$ being hydrogen or $C_1$–$C_6$-alkyl and $R^6$ being hydrogen or $C_1$–$C_6$-alkyl and it being possible for the cyclic groups, in turn, to be partially or fully halogenated and/or to have attached to them one to three of the following substituents: cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy which can be halogenated, and the salts thereof.

Furthermore, preferred compounds of the formula I are those where m is 0.

Equally preferred compounds of the formula I are those where $R^1$ is methyl.

Besides, preferred compounds I are those where $R^3$ is hydrogen, cyclopropyl, methyl, ethyl, 1-methylethyl, trifluoromethyl, cyano or methoxy.

Especially preferred compounds I are those where $R^3$ is methyl.

Moreover, preferred compounds I are those where $R^3$ is trifluoromethyl.

Also especially preferred compounds I are those where $R^3$ is methoxy.

Moreover, preferred compounds I are those where $R^4$ is unsubstituted or substituted $C_1$–$C_6$-alkyl, $C_2$–$C_6$-alkenyl or $C_2$–$C_6$-alkynyl.

Additionally preferred compounds I are those where $R^4$ is unsubstituted or substituted heterocyclyl or unsubstituted or substituted $C_3$–$C_6$-cycloalkenyl.

Especially preferred compounds I are those where $R^4$ is $C_1$–$C_4$-alkyl.

Additionally preferred compounds I are those where $R^4$ is unsubstituted or substituted $C_3$–$C_6$-cycloalkyl.

Moreover, preferred compounds I are those where $R^4$ is unsubstituted or substituted aryl or hetaryl.

Moreover, preferred compounds I are those where $R^4$ is unsubstituted or substituted pyridyl, pyrimidyl, pyrazinyl, pyridazinyl or triazinyl.

Moreover, preferred compounds I are those where $R^4$ is unsubstituted or substituted furyl, thienyl or pyrrolyl.

Moreover, preferred compounds I are those where $R^4$ is unsubstituted or substituted oxazolyl, thiazolyl, isoxazolyl, isothiazolyl, pyrazolyl or imidazolyl.

Moreover, preferred compounds I are those where $R^4$ is unsubstituted or substituted oxadiazolyl, thiadiazolyl or triazolyl.

Additionally preferred compounds I are those where $R^4$ is phenyl which is unsubstituted or has attached to it one or two of the following groups: nitro, cyano, hydroxyl, amino, aminocarbonyl, aminothiocarbonyl, halogen, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, $C_1$–$C_4$-alkylamino, $C_1$–$C_4$-alkylcarbonyl, di-$C_1$–$C_4$-alkylamino, $C_1$–$C_4$-alkylsulfonyl, $C_1$–$C_4$-alkoxycarbonyl, $C_1$–$C_4$-alkylaminocarbonyl, di-$C_1$–$C_4$-alkylaminocarbonyl, $C_1$–$C_4$-alkylthio, $C_2$–$C_6$-alkenyl, $C_2$–$C_6$-alkenyloxy, $C_3$–$C_6$-alkynyloxy and $C_1$–$C_4$-alkylenedioxy which can be halogenated.

Very specially preferred compounds I are those where $R^4$ is phenyl which is unsubstituted or has attached to it one or two of the following groups: nitro, cyano, halogen, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy and $C_1$–$C_4$-alkylenedioxy which can be halogenated.

Besides, preferred compounds of the formula I are those where X is $NOCH_3$.

Besides, preferred compounds of the formula I are those where X is $CHOCH_3$.

Besides, preferred compounds of the formula I are those where X
is $CHCH_3$.

Moreover, preferred compounds of the formula I are those where Y is O.

Additionally preferred compounds of the formula I are those where Y is NH.

Compounds I which are preferred with a view to their use are, in particular, those compiled in the tables which follow.

The tables which follow (1 to 36) are based on the formulae I.1, I.2, I.3 and I.4.

(I.1)

(I.2)

(I.3)

(I.4)

Table 1
Compounds of the formula I.1 where
  $R^3$=hydrogen;
  $R^4$=in each case one line of Table A.
Table 2
Compounds of the formula I.2 where
  $R^3$=hydrogen;
  $R^4$=in each case one line of Table A.
Table 3
Compounds of the formula I.3 where
  $R^3$=hydrogen;
  $R^4$=in each case one line of Table A.
Table 4
Compounds of the formula I.4 where
  $R^3$=hydrogen;
  $R^4$=in each case one line of Table A.
Table 5
Compounds of the formula I.1 where
  $R^3$=methyl;
  $R^4$=in each case one line of Table A.
Table 6
Compounds of the formula I.2 where
  $R^3$=methyl;
  $R^4$=in each case one line of Table A.
Table 7
Compounds of the formula I.3 where
  $R^3$=methyl;
  $R^4$=in each case one line of Table A.
Table 8
Compounds of the formula I.4 where
  $R^3$=methyl;
  $R^4$=in each case one line of Table A.
Table 9
Compounds of the formula I.1 where
  $R^3$=ethyl;
  $R^4$=in each case one line of Table A.
Table 10
Compounds of the formula I.2 where
  $R^3$=ethyl;
  $R^4$=in each case one line of Table A.
Table 11
Compounds of the formula I.3 where
  $R^3$=ethyl;
  $R^4$=in each case one line of Table A.
Table 12
Compounds of the formula I.4 where
  $R^3$=ethyl;
  $R^4$=in each case one line of Table A.
Table 13
Compounds of the formula I.1 where
  $R^3$=n-propyl;
  $R^4$=in each case one line of Table A.
Table 14
Compounds of the formula I.2 where
  $R^3$=n-propyl;
  $R^4$=in each case one line of Table A.
Table 15
Compounds of the formula I.3 where
  $R^3$=n-propyl;
  $R^4$=in each case one line of Table A.
Table 16
Compounds of the formula I.4 where
  $R^3$=n-propyl;
  $R^4$=in each case one line of Table A.
Table 17
Compounds of the formula I.1 where
  $R^3$=isopropyl;
  $R^4$=in each case one line of Table A.

Table 18
Compounds of the formula I.2 where
 $R^3$=isopropyl;
 $R^4$=in each case one line of Table A.
Table 19
Compounds of the formula I.3 where
 $R^3$=isopropyl;
 $R^4$=in each case one line of Table A.
Table 20
Compounds of the formula I.4 where
 $R^3$=isopropyl;
 $R^4$=in each case one line of Table A.
Table 21
Compounds of the formula I.1 where
 $R^3$=cyclopropyl;
 $R^4$=in each case one line of Table A.
Table 22
Compounds of the formula I.2 where
 $R^3$=cyclopropyl;
 $R^4$=in each case one line of Table A.
Table 23
Compounds of the formula I.3 where
 $R^3$=cyclopropyl;
 $R^4$=in each case one line of Table A.
Table 24
Compounds of the formula I.4 where
 $R^3$=cyclopropyl;
 $R^4$=in each case one line of Table A.
Table 25
Compounds of the formula I.1 where
 $R^3$=trifluoromethyl;
 $R^4$=in each case one line of Table A.
Table 26
Compounds of the formula I.2 where
 $R^3$=trifluoromethyl;
 $R^4$=in each case one line of Table A.
Table 27
Compounds of the formula I.3 where
 $R^3$=trifluoromethyl;
 $R^4$=in each case one line of Table A.
Table 28
Compounds of the formula I.4 where
 $R^3$=trifluoromethyl;
 $R^4$=in each case one line of Table A.
Table 29
Compounds of the formula I.1 where
 $R^3$=cyano;
 $R^4$=in each case one line of Table A.
Table 30
Compounds of the formula I.2 where
 $R^3$=cyano;
 $R^4$=in each case one line of Table A.
Table 31
Compounds of the formula I.3 where
 $R^3$=cyano;
 $R^4$=in each case one line of Table A.
Table 32
Compounds of the formula I.4 where
 $R^3$=cyano;
 $R^4$=in each case one line of Table A.

Table 33
Compounds of the formula I.1 where
 $R^3$=methoxy;
 $R^4$=in each case one line of Table A.
Table 34
Compounds of the formula I.2 where
 $R^3$=methoxy;
 $R^4$=in each case one line of Table A.
Table 35
Compounds of the formula I.3 where
 $R^3$=methoxy;
 $R^4$=in each case one line of Table A.
Table 36
Compounds of the formula I.4 where
 $R^3$=methoxy;
 $R^4$=in each case one line of Table A.

TABLE A

| No. | $R^5$ |
|---|---|
| 1 | H |
| 2 | $CH_3$ |
| 3 | $C_2H_5$ |
| 4 | $n\text{-}C_3H_7$ |
| 5 | $i\text{-}C_3H_7$ |
| 6 | cyclopropyl |
| 7 | $n\text{-}C_4H_9$ |
| 8 | $s\text{-}C_4H_9$ |
| 9 | $i\text{-}C_4H_9$ |
| 10 | $t\text{-}C_4H_9$ |
| 11 | $n\text{-}C_5H_{11}$ |
| 12 | $i\text{-}C_5H_{11}$ |
| 13 | neo-$C_5H11$ |
| 14 | cyclopentyl |
| 15 | $n\text{-}C_6H_{13}$ |
| 16 | cyclohexyl |
| 17 | cyclobutyl |
| 18 | $CH_2CH_2Cl$ |
| 19 | $(CH_2)_4Cl$ |
| 20 | $CH_2CN$ |
| 21 | $CH_2CH_2CN$ |
| 22 | $(CH_2)_3CN$ |
| 23 | $(CH_2)_4CN$ |
| 24 | $(CH_2)_6CN$ |
| 25 | cyclohexylmethyl |
| 26 | 2-cyclohexyleth-1-yl |
| 27 | cyclopropylmethyl |
| 28 | 2-cyclopropyleth-1-yl |
| 29 | 2-methoxyeth-1-yl |
| 30 | 2-ethoxyeth-1-yl |
| 31 | 2-isopropoxyeth-1-yl |
| 32 | 3-methoxyprop-1-yl |
| 33 | 3-ethoxyprop-1-yl |
| 34 | 3-isopropoxyprop-1-yl |
| 35 | 4-methoxybut-1-yl |
| 36 | 4-isopropoxybut-1-yl |
| 37 | prop-2-en-1-yl |
| 38 | but-2-en-1-yl |
| 39 | 3-methylbut-2-en-1-yl |
| 40 | 2-vinyloxyeth-1-yl |
| 41 | allyloxyeth-1-yl |
| 42 | 2-trifluoromethoxyeth-1-yl |
| 43 | 3-trifluoromethoxyprop-1-yl |
| 44 | 4-difluoromethoxybut-1-yl |
| 45 | hydroxycarbonylmethyl |
| 46 | methoxycarbonylmethyl |
| 47 | aminocarbonylmethyl |
| 48 | N-methylaminocarbonylmethyl |
| 49 | N,N-dimethylaminocarbonyl-methyl |
| 50 | 2-hydroxycarbonyleth-1-yl |
| 51 | 2-methoxycarbonyleth-1-yl |
| 52 | 2-aminocarbonyleth-1-yl |
| 53 | 2-N-methylaminocarbonyleth-1-yl |
| 54 | 2-dimethylaminocarbonyleth-1-yl |
| 55 | 2-aminoeth-1-yl |

TABLE A-continued

| No. | R⁵ |
|---|---|
| 56 | 2-aminoprop-1-yl |
| 57 | 4-aminobut-1-yl |
| 58 | 3-dimethylaminoprop-1-yl |
| 59 | 4-aminothiocarbonylbut-1-yl |
| 60 | E-3-chloroprop-2-en-1-yl |
| 61 | Z-3-chloroprop-2-en-1-yl |
| 62 | prop-2-yn-1-yl |
| 63 | but-2-yn-1-yl |
| 64 | but-3-yn-1-yl |
| 65 | 3-chloroprop-2-yn-1-yl |
| 66 | 6-aminocarbonylhex-1-yl |
| 67 | 3-aminothiocarbonylprop-1-yl |
| 68 | 2-aminothiocarbonyleth-1-yl |
| 69 | aminothiocarbonylmethyl |
| 70 | 4-(N,N-dimethylamino)but-1-yl |
| 71 | 2-(methylthio)eth-1-yl |
| 72 | 2-(methylsulfonyl)eth-1-yl |
| 73 | 4-(methylthio)prop-1-yl |
| 74 | 4-(methylsulfonyl)prop-1-yl |
| 75 | benzyl |
| 76 | 2-F—$C_6H_4$—$CH_2$ |
| 77 | 3-F—$C_6H_4$—$CH_2$ |
| 78 | 4-F—$C_6H_4$—$CH_2$ |
| 79 | 2,3-$F_2$—$C_6H_3$—$CH_2$ |
| 80 | 2,4-$F_2$—$C_6H_3$—$CH_2$ |
| 81 | 2,5-$F_2$—$C_6H_3$—$CH_2$ |
| 82 | 2,6-$F_2$—$C_6H_3$—$CH_2$ |
| 83 | 3,4-$F_2$—$C_6H_3$—$CH_2$ |
| 84 | 3,5-$F_2$—$C_6H_3$—$CH_2$ |
| 85 | 2-Cl—$C_6H_4$—$CH_2$ |
| 86 | 3-Cl—$C_6H_4$—$CH_2$ |
| 87 | 4-Cl—$C_6H_4$—$CH_2$ |
| 88 | 2,3-$Cl_2$—$C_6H_3$—$CH_2$ |
| 89 | 2,4-$Cl_2$—$C_6H_3$—$CH_2$ |
| 90 | 2,5-$Cl_2$—$C_6H_3$—$CH_2$ |
| 91 | 2,6-$Cl_2$—$C_6H_3$—$CH_2$ |
| 92 | 3,4-$Cl_2$—$C_6H_3$—$CH_2$ |
| 93 | 3,5-$Cl_2$—$C_6H_3$—$CH_2$ |
| 94 | 2,3,4-$Cl_3$—$C_6H_2$—$CH_2$ |
| 95 | 2,3,5-$Cl_3$—$C_6H_2$—$CH_2$ |
| 96 | 2,3,6-$Cl_3$—$C_6H_2$—$CH_2$ |
| 97 | 2,4,5-$Cl_3$—$C_6H_2$—$CH_2$ |
| 98 | 2,4,6-$Cl_3$—$C_6H_2$—$CH_2$ |
| 99 | 3,4,5-$Cl_3$—$C_6H_2$—$CH_2$ |
| 100 | 2-Br—$C_6H_4$—$CH_2$ |
| 101 | 3-Br—$C_6H_4$—$CH_2$ |
| 102 | 4-Br—$C_6H_4$—$CH_2$ |
| 103 | 2,3-$Br_2$—$C_6H_3$—$CH_2$ |
| 104 | 2,4-$Br_2$—$C_6H_3$—$CH_2$ |
| 105 | 2,5-$Br_2$—$C_6H_3$—$CH_2$ |
| 106 | 2,6-$Br_2$—$C_6H_3$—$CH_2$ |
| 107 | 3,4-$Br_2$—$C_6H_3$—$CH_2$ |
| 108 | 3,5-$Br_2$—$C_6H_3$—$CH_2$ |
| 109 | 2-F, 3-Cl—$C_6H_3$—$CH_2$ |
| 110 | 2-F, 4-Cl—$C_6H_3$—$CH_2$ |
| 111 | 2-F, 5-Cl—$C_6H_3$—$CH_2$ |
| 112 | 2-F, 3-Br—$C_6H_3$—$CH_2$ |
| 113 | 2-F, 4-Br—$C_6H_3$—$CH_2$ |
| 114 | 2-F, 5-Br—$C_6H_3$—$CH_2$ |
| 115 | 2-Cl, 3-Br—$C_6H_3$—$CH_2$ |
| 116 | 2-Cl, 4-Br—$C_6H_3$—$CH_2$ |
| 117 | 2-Cl, 5-Br—$C_6H_3$—$CH_2$ |
| 118 | 3-F, 4-Cl—$C_6H_3$—$CH_2$ |
| 119 | 3-F, 5-Cl—$C_6H_3$—$CH_2$ |
| 120 | 3-F, 6-Cl—$C_6H_3$—$CH_2$ |
| 121 | 3-F, 4-Br—$C_6H_3$—$CH_2$ |
| 122 | 3-F, 5-Br—$C_6H_3$—$CH_2$ |
| 123 | 3-F, 6-Br—$C_6H_3$—$CH_2$ |
| 124 | 3-Cl, 4-Br—$C_6H_3$—$CH_2$ |
| 125 | 3-Cl, 5-Br—$C_6H_3$—$CH_2$ |
| 126 | 3-Cl, 6-Br—$C_6H_3$—$CH_2$ |
| 127 | 4-F, 5-Cl—$C_6H_3$—$CH_2$ |
| 128 | 4-F, 6-Cl—$C_6H_3$—$CH_2$ |
| 129 | 4-F, 5-Br—$C_6H_3$—$CH_2$ |
| 130 | 4-F, 6-Br—$C_6H_3$—$CH_2$ |
| 131 | 4-Cl, 5-Br—$C_6H_3$—$CH_2$ |
| 132 | 5-F, 6-Cl—$C_6H_3$—$CH_2$ |
| 133 | 5-F, 6-Br—$C_6H_3$—$CH_2$ |
| 134 | 5-Cl, 6-Br—$C_6H_3$—$CH_2$ |
| 135 | 3-Br, 4-Cl, 5-Br—$C_6H_2$—$CH_2$ |
| 136 | 2-CN—$C_6H_4$—$CH_2$ |
| 137 | 3-CN—$C_6H_4$—$CH_2$ |
| 138 | 4-CN—$C_6H_4$—$CH_2$ |
| 139 | 2-$NO_2$—$C_6H_4$—$CH_2$ |
| 140 | 3-$NO_2$—$C_6H_4$—$CH_2$ |
| 141 | 4-$NO_2$—$C_6H_4$—$CH_2$ |
| 142 | 2-$CH_3$—$C_6H_4$—$CH_2$ |
| 143 | 3-$CH_3$—$C_6H_4$—$CH_2$ |
| 144 | 4-$CH_3$—$C_6H_4$—$CH_2$ |
| 145 | 2,3-$(CH_3)_2$—$C_6H_3$—$CH_2$ |
| 146 | 2,4-$(CH_3)_2$—$C_6H_3$—$CH_2$ |
| 147 | 2,5-$(CH_3)_2$—$C_6H_3$—$CH_2$ |
| 148 | 2,6-$(CH_3)_2$—$C_6H_3$—$CH_2$ |
| 149 | 3,4-$(CH_3)_2$—$C_6H_3$—$CH_2$ |
| 150 | 3,5-$(CH_3)_2$—$C_6H_3$—$CH_2$ |
| 151 | 2-$C_2H_5$—$C_6H_4$—$CH_2$ |
| 152 | 3-$C_2H_5$—$C_6H_4$—$CH_2$ |
| 153 | 4-$C_2H_5$—$C_6H_4$—$CH_2$ |
| 154 | 2-i-$C_3H_7$—$C_6H_4$—$CH_2$ |
| 155 | 3-i-$C_3H_7$—$C_6H_4$—$CH_2$ |
| 156 | 4-i-$C_3H_7$—$C_6H_4$—$CH_2$ |
| 157 | 2-cyclohexyl-$C_6H_4$—$CH_2$ |
| 158 | 3-cyclohexyl-$C_6H_4$—$CH_2$ |
| 159 | 4-cyclohexyl-$C_6H_4$—$CH_2$ |
| 160 | 2-vinyl-$C_6H_4$—$CH_2$ |
| 161 | 3-vinyl-$C_6H_4$—$CH_2$ |
| 162 | 4-vinyl-$C_6H_4$—$CH_2$ |
| 163 | 2-allyl-$C_6H_4$—$CH_2$ |
| 164 | 3-allyl-$C_6H_4$—$CH_2$ |
| 165 | 4-allyl-$C_6H_4$—$CH_2$ |
| 166 | 2-$C_6H_5$—$C_6H_4$—$CH_2$ |
| 167 | 3-$C_6H_5$—$C_6H_4$—$CH_2$ |
| 168 | 4-$C_6H_5$—$C_6H_4$—$CH_2$ |
| 169 | 3-$CH_3$, 5-t-$C_4H_9$—$C_6H_3$—$CH_2$ |
| 170 | 2-OH—$C_6H_4$—$CH_2$ |
| 171 | 3-OH—$C_6H_4$—$CH_2$ |
| 172 | 4-OH—$C_6H_4$—$CH_2$ |
| 173 | 2-$OCH_3$—$C_6H_4$—$CH_2$ |
| 174 | 3-$OCH_3$—$C_6H_4$—$CH_2$ |
| 175 | 4-$OCH_3$—$C_6H_4$—$CH_2$ |
| 176 | 2,3-$(OCH_3)_2$—$C_6H_3$—$CH_2$ |
| 177 | 2,4-$(OCH_3)_2$—$C_6H_3$—$CH_2$ |
| 178 | 2,5-$(OCH_3)_2$—$C_6H_3$—$CH_2$ |
| 179 | 3,4-$(OCH_3)_2$—$C_6H_3$—$CH_2$ |
| 180 | 3,5-$(OCH_3)_2$—$C_6H_3$—$CH_2$ |
| 181 | 3,4,5-$(OCH_3)_3$—$C_6H_2$—$CH_2$ |
| 182 | 2-$OC_2H_5$—$C_6H_4$—$CH_2$ |
| 183 | 3-$OC_2H_5$—$C_6H_4$—$CH_2$ |
| 184 | 4-$OC_2H_5$—$C_6H_4$—$CH_2$ |
| 185 | 2-O-(n-$C_3H_7$)—$C_6H_4$—$CH_2$ |
| 186 | 3-O-(n-$C_3H_7$)—$C_6H_4$—$CH_2$ |
| 187 | 4-O-(n-$C_3H_7$)—$C_6H_4$—$CH_2$ |
| 188 | 2-O-(i-$C_3H_7$)—$C_6H_4$—$CH_2$ |
| 189 | 3-O-(i-$C_3H_7$)—$C_6H_4$—$CH_2$ |
| 190 | 4-O-(i-$C_3H_7$)—$C_6H_4$—$CH_2$ |
| 191 | 4-O-n-$C_4H_9$)—$C_6H_4$—$CH_2$ |
| 192 | 3-O-(t-$C_4H_9$)—$C_6H_4$—$CH_2$ |
| 193 | 4-O-(n-$C_6H_{13}$)—$C_6H_4$—$CH_2$ |
| 194 | 2-O-allyl-$C_6H_4$—$CH_2$ |
| 195 | 3-O-allyl-$C_6H_4$—$CH_2$ |
| 196 | 4-O-allyl-$C_6H_4$—$CH_2$ |
| 197 | 2-$CF_3$—$C_6H_4$—$CH_2$ |
| 198 | 3-$CF_3$—$C_6H_4$—$CH_2$ |
| 199 | 4-$CF_3$—$C_6H_4$—$CH_2$ |
| 200 | 2-acetyl-$C_6H_4$—$CH_2$ |
| 201 | 3-acetyl-$C_6H_4$—$CH_2$ |
| 202 | 4-acetyl-$C_6H_4$—$CH_2$ |
| 203 | 2-methoxycarbonyl-$C_6H_4$—$CH_2$ |
| 204 | 3-methoxycarbonyl-$C_6H_4$—$CH_2$ |
| 205 | 4-methoxycarbonyl-$C_6H_4$—$CH_2$ |
| 206 | 2-aminocarbonyl-$C_6H_4$—$CH_2$ |
| 207 | 3-aminocarbonyl-$C_6H_4$—$CH_2$ |
| 208 | 4-aminocarbonyl-$C_6H_4$—$CH_2$ |
| 209 | 2-dimethylaminocarbonyl-$C_6H_4$—$CH_2$ |

TABLE A-continued

| No. | R⁵ |
|---|---|
| 210 | 3-dimethylaminocarbonyl-C₆H₄—CH₂ |
| 211 | 4-dimethylaminocarbonyl-C₆H₄—CH₂ |
| 212 | 2-(N-methylaminocarbonyl)-C₆H₄—CH₂ |
| 213 | 3-(N-methylaminocarbonyl)-C₆H₄—CH₂ |
| 214 | 4-(N-methylaminocarbonyl)-C₆H₄—CH₂ |
| 215 | 2-H₂N—C₆H₄—CH₂ |
| 216 | 3-H₂N—C₆H₄—CH₂ |
| 217 | 4-H₂N—C₆H₄—H₂ |
| 218 | 2-aminothiocarbonyl-C₆H₄—CH₂ |
| 219 | 3-aminothiocarbonyl-C₆H₄—CH₂ |
| 220 | 4-aminothiocarbonyl-C₆H₄—CH₂ |
| 221 | 2-methoxylminomethyi-C₆H₄—CH₂ |
| 222 | 3-methoxylminomethyi-C₆H₄—CH₂ |
| 223 | 4-methoxylminomethyi-C₆H₄—CH₂ |
| 224 | 3,4-methylenedioxy-C₆H₃—CH₂ |
| 225 | 3,4-difluoromethylenedioxy-C₆H₃—CH₂ |
| 226 | 2,3-methylenedioxy-C₆H₃—CH₂ |
| 227 | 2-(1'-methoxyiminoeth-1'-yl)-C₆H₄—CH₂ |
| 228 | 3-(1'-methoxyiminoeth-1'-yl)-C₆H₄—CH₂ |
| 229 | 4-(1'-methoxyiminoeth-1'-yl)-C₆H₄—CH₂ |
| 230 | 2-SCH₃—C₆H₄—CH₂ |
| 231 | 3-SCH₃—C₆H₄—CH₂ |
| 232 | 4-SCH₃—C₆H₄—CH₂ |
| 233 | 2-SO₂CH₃—C₆H₄—CH₂ |
| 234 | 3-SO₂CH₃—C₆H₄—CH₂ |
| 235 | 4-SO₂CH₃—C₆H₄—CH₂ |
| 236 | 2-OCF₃—C₆H₄—CH₂ |
| 237 | 3-OCF₃—C₆H₄—CH₂ |
| 238 | 4-OCF₃—C₆H₄—CH₂ |
| 239 | 2-OCHF₂—C₆H₄—CH₂ |
| 240 | 3-OCHF₂—C₆H₄—CH₂ |
| 241 | 4-OCHF₂—C₆H₄—CH₂ |
| 242 | 3-CF₃, 4-OCF₃—C₆H₃—CH₂ |
| 243 | 1-naphthyl-CH₂ |
| 244 | 2-naphthyl-CH₂ |
| 245 | 2-phenoxyeth-1-yl |
| 246 | 2-(2'-chlorophenoxy)eth-1-yl |
| 247 | 2-(3'-chlorophenoxy)eth-1-yl |
| 248 | 2-(4'-chlorophenoxy)eth-1-yl |
| 249 | 2-(3',5'-dichlorophenoxy)eth-1-yl |
| 250 | 2-(2'-cyanophenoxy)eth-1-yl |
| 251 | 2-(3'-cyanophenoxy)eth-1-yl |
| 252 | 2-(4'-cyanophenoxy)eth-1-yl |
| 253 | 2-(2'-methylphenoxy)eth-1-yl |
| 254 | 2-(3'-methylphenoxy)eth-1-yl |
| 255 | 2-(4'-methylphenoxy)eth-1-yl |
| 256 | 2-(3'-t-butylphenoxy)eth-1-yl |
| 257 | 2-(4'-t-butylphenoxy)eth-1-yl |
| 258 | 2-(2'-nitrophenoxy)eth-1-yl |
| 259 | 2-(3'-nitrophenoxy)eth-1-yl |
| 260 | 2-(4'-nitrophenoxy)eth-1-yl |
| 261 | 2-(2'-methoxyphenoxy)eth-1-yl |
| 262 | 2-(3'-methoxyphenoxy)eth-1-yl |
| 263 | 2-(4'-methoxyphenoxy)eth-1-yl |
| 264 | 2-(2'-trifluoromethylphenoxy)eth-1-yl |
| 265 | 2-(3'-trifluoromethylphenoxy)eth-1-yl |
| 266 | 2-(4'-trifluoromethylphenoxy)eth-1-yl |
| 267 | 2-(2'-acetylphenoxy)eth-1-yl |
| 268 | 2-(3'-acetylphenoxy)eth-1-yl |
| 269 | 2-(4'-acetylphenoxy)eth-1-yl |
| 270 | 2-(2'-methoxycarbonyl)eth-1-yl |
| 271 | 2-(3'-methoxycarbonyl)eth-1-yl |
| 272 | 2-(4'-methoxycarbonyl)eth-1-yl |
| 273 | 2-(2'-dimethylaminocarbonyl)eth-1-yl |
| 274 | 2-(3'-dimethylaminocarbonyl)eth-1-yl |
| 275 | 2-(4'-dimethylaminocarbonyl)eth-1-yl |
| 276 | 2-(2'-aminothiocarbonyl)eth-1-yl |
| 277 | 2-(3'-aminothiocarbonyl)eth-1-yl |
| 278 | 2-(4'-aminothiocarbonyl)eth-1-yl |
| 279 | 2-(2'-methylsulfonyl)eth-1-yl |
| 280 | 2-(3'-methylsulfonyl)eth-1-yl |
| 281 | 2-(4'-methylsulfonyl)eth-1-yl |
| 282 | 3-phenoxyprop-1-yl |
| 283 | 3-(2'-chlorophenoxy)prop-1-yl |
| 284 | 3-(3'-chlorophenoxy)prop-1-yl |
| 285 | 3-(4'-chlorophenoxy)prop-1-yl |
| 286 | 3-(3',5',dichlorophenoxy)prop-1-yl |
| 287 | 3-(2'-cyanophenoxy)prop-1-yl |
| 288 | 3-(3'-cyanophenoxy)prop-1-yl |
| 289 | 3-(4'-cyanophenoxy)prop-1-yl |
| 290 | 3-(2'-methylphenoxy)prop-1-yl |
| 291 | 3-(3'-methylphenoxy)prop-1-y1 |
| 292 | 3-(4'-methylphenoxy)prop-1-yl |
| 293 | 3-(2'-methoxyphenoxy)prop-1-y1 |
| 294 | 3-(3'-methoxyphenoxy)prop-1-yl |
| 295 | 3-(4'-methoxyphenoxy)prop-1-yl |
| 296 | 3-(2'-trifluoromethylphenoxy)prop-1-yl |
| 297 | 3-(3'-trifluoromethylphenoxy)prop-1-yl |
| 298 | 3-(4'-trifluoromethylphenoxy)prop-1-yl |
| 299 | 4-phenoxybut-1-yl |
| 300 | 2-phenyleth-1-yl |
| 301 | 2-(2'-chlorophenyl)eth-1-yl |
| 302 | 2-(3'-chlorophenyl)eth-1-yl |
| 303 | 2-(4'-chlorophenyl)eth-1-yl |
| 304 | 2-(3',5'-dichlorophenyl)eth-1-yl |
| 305 | 2-(2'-cyanophenyl)eth-1-yl |
| 306 | 2-(3'-cyanophenyl)eth-1-y1 |
| 307 | 2-(4'-cyanophenyl)eth-1-yl |
| 308 | 2-(2'-methylphenyl)eth-1-yl |
| 309 | 2-(3'-methylphenyl)eth-1-yl |
| 310 | 2-(4'-methylphenyl)eth-1-yl |
| 311 | 2-(2'-methoxyphenyl)eth-1-yl |
| 312 | 2-(3'-methoxyphenyl)eth-1-yl |
| 313 | 2-(4'-methoxyphenyl)eth-1-yl |
| 314 | 2-(2'-trifluoromethylphenyl)eth-1-yl |
| 315 | 2-(3'-trifluoromethylphenyl)eth-1-yl |
| 316 | 2-(4'-trifluoromethylphenyl)eth-1-yl |
| 317 | 3-phenylprop-1-yl |
| 318 | 3-(2'-chlorophenyl)prop-1-yl |
| 319 | 3-(3'-chlorophenyl)prop-1-yl |
| 320 | 3-(4'-chlorophenyl)prop-1-yl |
| 321 | 3-(2'-cyanophenyl)prop-1-yl |
| 322 | 3-(3'-cyanophenyl)prop-1-yl |
| 323 | 3-(4'-cyanophenyl)prop-1-yl |
| 324 | 3-(2'-trifluoromethylphenyl)prop-1-yl |
| 325 | 4-phenylbut-1-yl |
| 326 | 4-(4'-chlorophenyl)but-1-yl |
| 327 | 6-(4'-chlorophenyl)hex-1-yl |
| 328 | 2-pyridylmethyl |
| 329 | 3-pyridylmethyl |
| 330 | 4-pyridylmethyl |
| 331 | 4-chloropyridin-2-ylmethyl |
| 332 | 5-chloropyridin-2-ylmethyl |
| 333 | 6-chloropyridin-2-ylmethyl |
| 334 | 5-chloropyridin-3-ylmethyl |
| 335 | 6-chloropyridin-3-ylmethyl |
| 336 | 2-chloropyridin-4-ylmethyl |
| 337 | 2-pyrimidinylmethyl |
| 338 | 4-chloropyrimidin-2-ylmethyl |
| 339 | 5-chloropyrimidin-2-ylmethyl |
| 340 | 2-chloropyrimidin-4-ylmethyl |
| 341 | 6-chloropyrimidin-4-ylmethyl |
| 342 | 2-chloropyrimidin-5-ylmethyl |
| 343 | 4-pyridazinylmethyl |
| 344 | 2-pyrazinylmethyl |
| 345 | 5-chloropyrazin-2-ylmethyl |
| 346 | 6-chloropyrazin-2-ylmethyl |
| 347 | 3-pyridazinylmethyl |
| 348 | 6-chloropyridazin-3-ylmethyl |
| 349 | 1,3,5-triazinylmethyl |
| 350 | 2-furylmethyl |
| 351 | 3-furylmethyl |
| 352 | 4-bromofur-2-ylmethyl |
| 353 | 5-chlorofur-2-ylmethyl |
| 354 | 2-thienylmethyl |
| 355 | 3-thienylmethyl |
| 356 | 5-methylthien-3-ylmethyl |
| 357 | 5-chlorothien-2-ylmethyl |
| 358 | 2-chlorothien-4-ylmethyl |
| 359 | 2-pyrrolylmethyl |
| 360 | 3-pyrrolylmethyl |
| 361 | 2-oxazolylmethyl |
| 362 | 4-methyloxazol-2-ylmethyl |
| 363 | 5-methyloxazol-2-ylmethyl |

TABLE A-continued

| No. | R⁵ |
|---|---|
| 364 | 4-chloro-oxazol-2-ylmethyl |
| 365 | 5-chloro-oxazol-2-ylmethyl |
| 366 | 4-oxazolylmethyl |
| 367 | 2-methyloxazol-4-ylmethyl |
| 368 | 5-methyloxazol-4-ylmethyl |
| 369 | 2-chloro-oxazol-4-ylmethyl |
| 370 | 5-chloro-oxazol-4-ylmethyl |
| 371 | 5-oxazolylmethyl |
| 372 | 2-methyloxazol-5-ylmethyl |
| 373 | 4-methyloxazol-5-ylmethyl |
| 374 | 2-chloro-oxazol-5-ylmethyl |
| 375 | 4-chloro-oxazol-5-ylmethyl |
| 376 | 2-thiazolylmethyl |
| 377 | 4-methylthiazol-2-ylmethyl |
| 378 | 5-methylthiazol-2-ylmethyl |
| 379 | 4-chlorothiazol-2-ylmethyl |
| 380 | 5-chlorothiazol-2-ylmethyl |
| 381 | 4-thiazolylmethyl |
| 382 | 2-methylthiazol-4-ylmethyl |
| 383 | 5-methylthiazol-4-ylmethyl |
| 384 | 2-chlorothiazol-4-ylmethyl |
| 385 | 5-chlorothiazol-4-ylmethyl |
| 386 | 5-thiazolylmethyl |
| 387 | 2-methylthiazol-5-ylmethyl |
| 388 | 4-methylthiazol-5-ylmethyl |
| 389 | 2-chlorothiazol-5-ylmethyl |
| 390 | 4-chlorothiazol-5-ylmethyl |
| 391 | 3-isoxazolylmethyl |
| 392 | 4-methylisoxazol-3-ylmethyl |
| 393 | 5-methylisoxazol-3-ylmethyl |
| 394 | 4-chloroisoxazol-3-ylmethyl |
| 395 | 5-chloroisoxazol-3-ylmethyl |
| 396 | 4-isoxazolylmethyl |
| 397 | 3-methylisoxazol-4-ylmethyl |
| 398 | 5-methylisoxazol-4-ylmethyl |
| 399 | 3-chloroisoxazol-4-ylmethyl |
| 400 | 5-chloroisoxazol-4-ylmethyl |
| 401 | 5-isoxazolylmethyl |
| 402 | 3-methylisoxazol-5-ylmethyl |
| 403 | 4-methylisoxazol-5-ylmethyl |
| 404 | 3-chloroisoxazol-5-ylmethyl |
| 405 | 4-chloroisoxazol-5-ylmethyl |
| 406 | 3-isothiazolylmethyl |
| 407 | 4-methylisothiazol-3-ylmethyl |
| 408 | 5-methylisothiazol-3-ylmethyl |
| 409 | 4-chloroisothiazol-3-ylmethyl |
| 410 | 5-chloroisothiazol-3-ylmethyl |
| 411 | 4-isothiazolylmethyl |
| 412 | 3-methylisothiazol-4-ylmethyl |
| 413 | 5-methylisothiazol-4-ylmethyl |
| 414 | 3-chloroisothiazol-4-ylmethyl |
| 415 | 5-chloroisothiazol-4-ylmethyl |
| 416 | 5-isothiazolylmethyl |
| 417 | 3-methylisothiazol-5-ylmethyl |
| 418 | 4-methylisothiazol-5-ylmethyl |
| 419 | 3-chloroisothiazol-5-ylmethyl |
| 420 | 4-chloroisothiazol-5-ylmethyl |
| 421 | 4-imidazolylmethyl |
| 422 | 1-phenylpyrazol-3-ylmethyl |
| 423 | 1-methylimidazol-4-ylmethyl |
| 424 | 1-phenyl-1,2,4-triazol-3-ylmethyl |
| 425 | 1,2,4-oxadiazol-3-ylmethyl |
| 426 | 5-chloro-1,2,4-oxadiazol-3-ylmethyl |
| 427 | 5-methyl-1,2,4-oxadiazol-3-ylmethyl |
| 428 | 5-trifluoromethyl-1,2,4-oxadiazol-3-ylmethyl |
| 429 | 1,3,4-oxadiazol-2-ylmethyl |
| 430 | 5-chloro-1,3,4-oxadiazol-2-ylmethyl |
| 431 | 5-methyl-1,3,4-oxadiazol-2-ylmethyl |
| 432 | 5-methoxy-1,3,4-oxadiazol-2-ylmethyl |
| 433 | 1,2,4-thiadiazol-3-ylmethyl |
| 434 | 5-chloro-1,2,4-thiadiazol-3-ylmethyl |
| 435 | 5-methyl-1,2,4-thiadiazol-3-ylmethyl |
| 436 | 1,3,4-thiadiazol-2-ylmethyl |
| 437 | 5-chloro-1,3,4-thiadiazol-2-ylmethyl |
| 438 | 5-methyl-1,3,4-thiadiazol-2-ylmethyl |
| 439 | 5-cyano-1,3,4-thiadiazol-2-ylmethyl |
| 440 | 2-(2'-pyridinyloxy)eth-1-yl |
| 441 | 2-(3'-pyridinyloxy)eth-1-yl |
| 442 | 2-(4'-pyridinyloxy)eth-1-yl |
| 443 | 2-(2'-pyrimidinyloxy)eth-1-yl |
| 444 | 2-(4'-pyrimidinyloxy)eth-1-yl |
| 445 | 2-(5'-pyrimidinyloxy)eth-1-yl |
| 446 | 2-(2'-pyrazinyloxy)eth-1-yl |
| 447 | 2-(2'-pyridazinyloxy)eth-1-yl |
| 448 | 2-(3'-pyridazinyloxy)eth-1-yl |
| 449 | 2-(1',3',5'-triazinyloxy)eth-1-yl |
| 450 | 2-(5'-methylisoxazol-3'-yloxy)eth-1-yl |
| 451 | 2-(5'-chloroisoxazol-3'-yloxy)eth-1-yl |
| 452 | 2-(2'-methoxythiazol-4'-yloxy)eth-1-yl |
| 453 | 2-(4'-chloro-oxazol-2'-yloxy)eth-1-yl |
| 454 | 2-(1'-phenyl-1'H-1',2',4'-triazol-3'-yloxy)eth-1-yl |
| 455 | 2-(1'-phenylpyrazol-3'-yloxy)eth-1-yl |
| 456 | $C_6H_5$ |
| 457 | 2-F—$C_6H_4$ |
| 458 | 3-F—$C_6H_4$ |
| 459 | 4-F—$C_6H_4$ |
| 460 | 2,3-$F_2$—$C_6H_3$ |
| 461 | 2,4-$F_2$—$C_6H_3$ |
| 462 | 2,5-$F_2$—$C_6H_3$ |
| 463 | 2,6-$F_2$—$C_6H_3$ |
| 464 | 3,4-$F_2$—$C_6H_3$ |
| 465 | 3,5-$F_2$—$C_6H_3$ |
| 466 | 2-Cl—$C_6H_4$ |
| 467 | 3-Cl—$C_6H_4$ |
| 468 | 4-Cl—$C_6H_4$ |
| 469 | 2,3-$Cl_2$—$C_6H_3$ |
| 470 | 2,4-$Cl_2$—$C_6H_3$ |
| 471 | 2,5-$Cl_2$—$C_6H_3$ |
| 472 | 2,6-$Cl_2$—$C_6H_3$ |
| 473 | 3,4-$Cl_2$—$C_6H_3$ |
| 474 | 3,5-$Cl_2$—$C_6H_3$ |
| 475 | 2,3,4-$Cl_3$—$C_6H_2$ |
| 476 | 2,3,5-$Cl_3$—$C_6H_2$ |
| 477 | 2,3,6-$Cl_3$—$C_6H_2$ |
| 478 | 2,4,5-$Cl_3$—$C_6H_2$ |
| 479 | 2,4,6-$Cl_3$—$C_6H_2$ |
| 480 | 3,4,5-$Cl_3$—$C_6H_2$ |
| 481 | 2-Br—$C_6H_4$ |
| 482 | 3-Br—$C_6H_4$ |
| 483 | 4-Br—$C_6H_4$ |
| 484 | 2,3-$Br_2$—$C_6H_3$ |
| 485 | 2,4-$Br_2$—$C_6H_3$ |
| 486 | 2,5-$Br_2$—$C_6H_3$ |
| 487 | 2,6-$Br_2$—$C_6H_3$ |
| 488 | 3,4-$Br_2$—$C_6H_3$ |
| 489 | 3,5-$Br_2$—$C_6H_3$ |
| 490 | 2-F, 3-Cl—$C_6H_3$ |
| 491 | 2-F, 4-Cl—$C_6H_3$ |
| 492 | 2-F, 5-Cl—$C_6H_3$ |
| 493 | 2-F, 3-Br—$C_6H_3$ |
| 494 | 2-F, 4-Br—$C_6H_3$ |
| 495 | 2-F, 5-Br—$C_6H_3$ |
| 496 | 2-Cl, 3-Br—$C_6H_3$ |
| 497 | 2-Cl, 4-Br—$C_6H_3$ |
| 498 | 2-Cl, 5-Br—$C_6H_3$ |
| 499 | 3-F, 4-Cl—$C_6H_3$ |
| 500 | 3-F, 5-Cl—$C_6H_3$ |
| 501 | 3-F, 6-Cl—$C_6H_3$ |
| 502 | 3-F, 4-Br—$C_6H_3$ |
| 503 | 3-F, 5-Br—$C_6H_3$ |
| 504 | 3-F, 6-Br—$C_6H_3$ |
| 505 | 3-Cl, 4-Br—$C_6H_3$ |
| 506 | 3-Cl, 5-Br—$C_6H_3$ |
| 507 | 3-Cl, 6-Br—$C_6H_3$ |
| 508 | 4-F, 5-Cl—$C_6H_3$ |
| 509 | 4-F, 6-Cl—$C_6H_3$ |
| 510 | 4-F, 5-Br—$C_6H_3$ |
| 511 | 4-F, 6-Br—$C_6H_3$ |
| 512 | 4-Cl, 5-Br—$C_6H_3$ |
| 513 | 5-F, 6-Cl—$C_6H_3$ |
| 514 | 5-F, 6-Br—$C_6H_3$ |
| 515 | 5-Cl, 6-Br—$C_6H_3$ |
| 516 | 3-Br, 4-Cl, 5-Br—$C_6H'2$ |
| 517 | 2-CN—$C_6H_4$ |

TABLE A-continued

| No. | R⁵ |
|---|---|
| 518 | 3-CN—C₆H₄ |
| 519 | 4-CN—C₆H₄ |
| 520 | 2-NO₂—C₆H₄ |
| 521 | 3-NO₂—C₆H₄ |
| 522 | 4-NO₂—C₆H₄ |
| 523 | 2-CH₃—C₆H₄ |
| 524 | 3-CH₃—C₆H₄ |
| 525 | 4-CH₃—C₆H₄ |
| 526 | 2,3-(CH₃)₂—C₆H₃ |
| 527 | 2,4-(CH₃)₂—C₆H₃ |
| 528 | 2,5-(CH₃)₂—C₆H₃ |
| 529 | 2,6-(CH₃)₂—C₆H₃ |
| 530 | 3,4-(CH₃)₂—C₆H₃ |
| 531 | 3,5-(CH₃)₂—C₆H₃ |
| 532 | 2-C₂H₅—C₆H₄ |
| 533 | 3-C₂H₅—C₆H₄ |
| 534 | 4-C₂H₅—C₆H₄ |
| 535 | 2-i-C₃H₇—C₆H₄ |
| 536 | 3-i-C₃H₇—C₆H₄ |
| 537 | 4-i-C₃H₇—C₆H₄ |
| 538 | 3-tert-C₄H₉—C₆H₄ |
| 539 | 4-tert-C₄H₉—C₆H₄ |
| 540 | 2-vinyl-C₆H₄ |
| 541 | 3-vinyl-C₆H₄ |
| 542 | 4-vinyl-C₆H₄ |
| 543 | 2-allyl-C₆H₄ |
| 544 | 3-allyl-C₆H₄ |
| 545 | 4-allyl-C₆H₄ |
| 546 | 2-C₆H₅—C₆H₄ |
| 547 | 3-C₆H₅—C₆H₄ |
| 548 | 4-C₆H₅—C₆H₄ |
| 549 | 3-CH₃, 5-tert-C₄H₉—C₆H₃ |
| 550 | 2-OH—C₆H₄ |
| 551 | 3-OH—C₆H₄ |
| 552 | 4-OH—C₆H₄ |
| 553 | 2-OCH₃—C₆H₄ |
| 554 | 3-OCH₃—C₆H₄ |
| 555 | 4-OCH₃—C₆H₄ |
| 556 | 2,3-(OCH₃)₂—C₆H₃ |
| 557 | 2,4-(OCH₃)₂—C₆H₃ |
| 558 | 2,5-(OCH₃)₂—C₆H₃ |
| 559 | 3,4-(OCH₃)₂—C₆H₃ |
| 560 | 3,5-(OCH₃)₂—C₆H₃ |
| 561 | 3,4,5-(OCH₃)₃—C₆H₂ |
| 562 | 2-OC₂H₅—C₆H₄ |
| 563 | 3-OC₂H₅—C₆H₄ |
| 564 | 4-OC₂H₅—C₆H₄ |
| 565 | 2-O-(n-C₃H₇)—C₆H₄ |
| 566 | 3-O-(n-C₃H₇)—C₆H₄ |
| 567 | 4-O-(n-C₃H₇)—C₆H₄ |
| 568 | 2-O-(i-C₃H₇)—C₆H₄ |
| 569 | 3-O-(i-C₃H₇)—C₆H₄ |
| 570 | 4-O-(i-C₃H₇)—C₆H₄ |
| 571 | 4-O-(n-C₄H₉)—C₆H₄ |
| 572 | 3-O-(t-C₄H₉)—C₆H₄ |
| 573 | 4-O-(t-C₄H₉)—C₆H₄ |
| 574 | 2-O-allyl-C₆H₄ |
| 575 | 3-O-allyl-C₆H₄ |
| 576 | 4-O-allyl-C₆H₄ |
| 577 | 2-CF₃—C₆H₄ |
| 578 | 3-CF₃—C₆H₄ |
| 579 | 4-CF₃—C₆H₄ |
| 580 | 2-acetyl-C₆H₄ |
| 581 | 3-acetyl-C₆H₄ |
| 582 | 4-acetyl-C₆H₄ |
| 583 | 2-methoxycarbonyl-C₆H₄ |
| 584 | 3-methoxycarbonyl-C₆H₄ |
| 585 | 4-methoxycarbonyl-C₆H₄ |
| 586 | 2-aminocarbonyl-C₆H₄ |
| 587 | 3-aminocarbonyl-C₆H₄ |
| 588 | 4-aminocarbonyl-C₆H₄ |
| 589 | 2-dimethylaminocarbonyl-C₆H₄ |
| 590 | 3-dimethylaminocarbonyl-C₆H₄ |
| 591 | 4-dimethylaminocarbonyl-C₆H₄ |
| 592 | 2-(N-methylaminocarbonyl)-C₆H₄ |
| 593 | 3-(N-methylaminocarbonyl)-C₆H₄ |
| 594 | 4-(N-methylaminocarbonyl)-C₆H₄ |
| 595 | 2-H₂N-C₆H₄ |
| 596 | 3-H₂N-C₆H₄ |
| 597 | 4-H₂N-C₆H₄ |
| 598 | 2-aminothiocarbonyl-C₆H₄ |
| 599 | 3-aminothiocarbonyl-C₆H₄ |
| 600 | 4-aminothiocarbonyl-C₆H₄ |
| 601 | 2-methoxylminomethyl-C₆H₄ |
| 602 | 3-methoxylminomethyl-C₆H₄ |
| 603 | 4-methoxylminomethyl-C₆H₄ |
| 604 | 3,4-methylenedioxy-C₆H₃ |
| 605 | 3,4-difluoromethylenedioxy-C₆H₃ |
| 606 | 2,3-methylenedioxy-C₆H₃ |
| 607 | 2-(1'-methoxylminoeth-1-yl)-C₆H₄ |
| 608 | 3-(1'-methoxylminoeth-1'-yl)-C₆H₄ |
| 609 | 4-(1'-methoxylminoeth-1'-yl)-C₆H₄ |
| 610 | 2-SCH₃—C₆H₄ |
| 611 | 3-SCH₃—C₆H₄ |
| 612 | 4-SCH₃—C₆H₄ |
| 613 | 2-SO₂CH₃—C₆H₄ |
| 614 | 3-SO₂CH₃—C₆H₄ |
| 615 | 4-SO₂CH₃—C₆H₄ |
| 616 | 2-OCF₃—C₆H₄ |
| 617 | 3-OCF₃—C₆H₄ |
| 618 | 4-OCF₃—C₆H₄ |
| 619 | 2-OCHF₂—C₆H₄ |
| 620 | 3-OCHF₂—C₆H₄ |
| 621 | 4-OCHF₂—C₆H₄ |
| 622 | 3-CF₃, 4-OCF₃—C₆H₃ |
| 623 | 2-NHCH₃—C₆H₄ |
| 624 | 3-NHCH₃—C₆H₄ |
| 625 | 4-NHCH₃—C₆H₄ |
| 626 | 2-N(CH₃)₂—C₆H₄ |
| 627 | 3-N(CH₃)₂—C₆H₄ |
| 628 | 4-N(CH₃)₂—C₆H₄ |
| 629 | 2-ethoxycarbonyl-C₆H₄ |
| 630 | 3-ethoxycarbonyl-C₆H₄ |
| 631 | 4-ethoxycarbonyl-C₆H₄ |
| 632 | 2-CH₂CH₂F—C₆H₄ |
| 633 | 3-CH₂CH₂F—C₆H₄ |
| 634 | 4-CH₂CH₂F—C₆H₄ |
| 635 | 2-CH₂CF₃—C₆H₄ |
| 636 | 3-CH₂CF₃—C₆H₄ |
| 637 | 4-CH₂CF₃—C₆H₄ |
| 638 | 2-CF₂CHF₂—C₆H₄ |
| 639 | 3-CF₂CHF₂—C₆H₄ |
| 640 | 4-CF₂CHF₂—C₆H₄ |
| 641 | 2-CHF₂—C₆H₄ |
| 642 | 3-CHF₂—C₆H₄ |
| 643 | 4-CHF₂—C₆H₄ |
| 644 | 2-(1'-oxo-n-prop-1-yl)-C₆H₄ |
| 645 | 3-(1'-oxo-n-prop-1-yl)-C₆H₄ |
| 646 | 4-(1'-oxo-n-prop-1-yl)-C₆H₄ |
| 647 | 2-(1'-oxo-isoprop-1-yl)-C₆H₄ |
| 648 | 3-(1'-oxo-isoprop-1-yl)-C₆H₄ |
| 649 | 4-(1'-oxo-isoprop-1-yl)-C₆H₄ |
| 650 | 3-cyclopropyl-C₆H₄ |
| 651 | 4-cyclopropyl-C₆H₄ |
| 652 | 4-cyclohexyl-C₆H₄ |
| 653 | 1-naphthyl |
| 654 | 2-naphthyl |
| 655 | 2-pyridyl |
| 656 | 3-pyridyl |
| 657 | 4-pyridyl |
| 658 | 5-CH₃-pyridin-2-yl |
| 659 | 5-Cl-pyridin-2-yl |
| 660 | 6-Cl-pyridin-2-yl |
| 661 | 3,5-Cl₂-pyridin-2-yl |
| 662 | 6-OCH₃-pyridin-2-yl |
| 663 | 6-CH₃-pyridin-2-yl |
| 664 | 6-Cl-pyridin-3-yl |
| 665 | 6-CH₃-pyridin-3-yl |
| 666 | 6-OCH₃-pyridin-3-yl |
| 667 | 2-pyrimidinyl |
| 668 | 4-OCH₃-pyrimidin-2-yl |
| 669 | 4-OC₂H₅-pyrimidin-2-yl |
| 670 | 4-Cl-pyrimidin-2-yl |
| 671 | 4-CH₃-pyrimidin-2-yl |

TABLE A-continued

| No. | R⁵ |
|---|---|
| 672 | 5-CH₃-pyrimidin-2-yl |
| 673 | 5-Cl-pyrimidin-2-yl |
| 674 | 5-OCH₃-pyrimidin-2-yl |
| 675 | 5-OC₂H₅-pyrimidin-2-yl |
| 676 | 4-pyrimidinyl |
| 677 | 2-Cl-pyrimidin-4-yl |
| 678 | 2-OCH₃-pyrimidin-4-yl |
| 679 | 2-CH₃-pyrimidin-4-yl |
| 680 | 6-Cl-pyrimidin-4-yl |
| 681 | 6-CH₃-pyrimidin-4-yl |
| 682 | 6-OCH₃-pyrimidin-4-yl |
| 683 | 5-pyrimidinyl |
| 684 | 2-CH₃-pyrimidin-5-yl |
| 685 | 2-Cl-pyrimidin-5-yl |
| 686 | 2-OCH₃-pyrimidin-5-yl |
| 687 | 2-OC₂H₅-pyrimidin-5-yl |
| 688 | 2-furyl |
| 689 | 4-C₂H₅-fur-2-yl |
| 690 | 4-CH₃-fur-2-yl |
| 691 | 4-Cl-fur-2-yl |
| 692 | 4-CN-fur-2-yl |
| 693 | 5-CH₃-fur-2-yl |
| 694 | 5-Cl-fur-2-yl |
| 695 | 5-CN-fur-2-yl |
| 696 | 3-furyl |
| 697 | 5-CH₃-fur-3-yl |
| 698 | 5-Cl-fur-3-yl |
| 699 | 5-CN-fur-3-yl |
| 700 | 2-thienyl |
| 701 | 4-CH₃-thien-2-yl |
| 702 | 4-Cl-thien-2-yl |
| 703 | 4-CN-thien-2-yl |
| 704 | 5-CH₃-thien-2-yl |
| 705 | 5-Cl-thien-2-yl |
| 706 | 5-CN-thien-2-yl |
| 707 | 3-thienyl |
| 708 | 5-CH₃-thien-3-yl |
| 709 | 5-Cl-thien-3-yl |
| 710 | 5-CN-thien-3-yl |
| 711 | 4-CH₃-thien-3-yl |
| 712 | 5-F-thien-3-yl |
| 713 | 2-oxazolyl |
| 714 | 4-CH₃-oxazol-2-yl |
| 715 | 4-Cl-oxazol-2-yl |
| 716 | 4-CN-oxazol-2-yl |
| 717 | 5-CH₃-oxazol-2-yl |
| 718 | 5-Cl-oxazol-2-y4 |
| 719 | 5-CN-oxazol-2-yl |
| 720 | 4-oxazolyl |
| 721 | 2-CH₃-oxazol-4-yl |
| 722 | 2-Cl-oxazol-4-yl |
| 723 | 2-CN-oxazol-4-yl |
| 724 | 5-oxazolyl |
| 725 | 2-CH₃-oxazol-5-yl |
| 726 | 2-Cl-oxazol-5-yl |
| 727 | 2-CN-oxazol-5-yl |
| 728 | 3-iso-oxazolyl |
| 729 | 5-CH₃-iso-oxazol-3-yl |
| 730 | 5-Cl-iso-oxazol-3-yl |
| 731 | 5-CN-iso-oxazol-3-yl |
| 732 | 5-iso-oxazolyl |
| 733 | 3-CH₃-iso-oxazol-5-yl |
| 734 | 3-Cl-iso-oxazol-5-yl |
| 735 | 3-CN-iso-oxazol-5-yl |
| 736 | 2-thiazolyl |
| 737 | 4-CH₃-thiazol-2-yl |
| 738 | 4-Cl-thiazol-2-yl |
| 739 | 4-CN-thiazol-2-yl |
| 740 | 5-CH₃-thiazol-2-yl |
| 741 | 5-Cl-thiazol-2-yl |
| 742 | 5-CN-thiazol-2-yl |
| 743 | 4-thiazolyl |
| 744 | 2-CH₃-thiazol-4-yl |
| 745 | 2-Cl-thiazol-4-yl |
| 746 | 2-CN-thiazol-4-yl |
| 747 | 2-SCH₃-thiazol-4-yl |
| 748 | 5-thiazolyl |
| 749 | 2-CH₃-thiazol-5-yl |
| 750 | 2-Cl-thiazol-5-yl |
| 751 | 2-CN-thiazol-5-yl |
| 752 | 3-isothiazolyl |
| 753 | 5-CH₃-isothiazol-3-yl |
| 754 | 5-Cl-isothiazol-3-yl |
| 755 | 5-CN-isothiazol-3-yl |
| 756 | 5-isothiazolyl |
| 757 | 3-CH₃-isothiazol-5-yl |
| 758 | 3-Cl-isothiazol-5-yl |
| 759 | 3-CN-isothiazol-5-yl |
| 760 | 2-imidazolyl |
| 761 | 4-CH₃-imidazol-2-yl |
| 762 | 4-Cl-imidazol-2-yl |
| 763 | 4-CN-imidazol-2-yl |
| 764 | 1-CH₃-imidazol-2-yl |
| 765 | 1-CH₃, 4-Cl-imidazol-2-yl |
| 766 | 1,4-(CH₃)₂-imidazol-2-yl |
| 767 | 1-CH₃, 5-Cl-imidazol-2-yl |
| 768 | 1,5-(CH₃)₂-imidazol-2-yl |
| 769 | 4-imidazolyl |
| 770 | 2-CH₃-imidazol-4-yl |
| 771 | 2-Cl-imidazol-4-yl |
| 772 | 1-CH₃-imidazol-4-yl |
| 773 | 1,2-(CH₃)₂-imidazol-4-yl |
| 774 | 1-CH₃, 2-Cl-imidazol-4-yl |
| 775 | 1-CH₃-imidazol-5-yl |
| 776 | 1-CH₃, 3-Cl-imidazol-5-yl |
| 777 | 1,2-(CH₃)₂-imidazol-5-yl |
| 778 | 3-pyrazolyl |
| 779 | 5-CH₃-pyrazol-3-yl |
| 780 | 5-Cl-pyrazol-3-yl |
| 781 | 5-CN-pyrazol-3-yl |
| 782 | 1-CH₃-pyrazol-3-yl |
| 783 | 1-CH₃, 4-Cl-pyrazol-3-yl |
| 784 | 1-CH₃, 5-Cl-pyrazol-3-yl |
| 785 | 1,5-(CH₃)₂-pyrazol-3-yl |
| 786 | 1-CH₃-pyrazol-5-yl |
| 787 | 1-CH₃, 3-Cl-pyrazol-5-yl |
| 788 | 1,3-(CH₃)₂-pyrazol-5-yl |
| 789 | 4-pyrazolyl |
| 790 | 3-Cl-pyrazol-4-yl |
| 791 | 3-CH₃-pyrazol-4-yl |
| 792 | 1-CH₃-pyrazol-4-yl |
| 793 | 1-CH₃, 3-Cl-pyrazol-4-yl |
| 794 | 1,3-(CH₃)₂-pyrazol-4-yl |
| 795 | 1,3,4-oxadiazol-5-yl |
| 796 | 2-CH₃-1,3,4-oxadiazol-5-yl |
| 797 | 2-Cl-1,3,4-oxadiazol-5-yl |
| 798 | 2-CF₃-1,3,4-oxadiazol-5-yl |
| 799 | 2-i-C₃H₇-1,3,4-oxadiazol-5-yl |
| 800 | 2-OCH₃-1,3,4-oxadiazol-5-yl |
| 801 | 1,2,4-oxadiazol-3-yl |
| 802 | 5-CH₃-1,2,4-oxadiazol-3-yl |
| 803 | 5-i-C₃H₇-1,2,4-oxadiazol-3-yl |
| 804 | 5-Cl-1,2,4-oxadiazol-3-yl |
| 805 | 5-CF₃-1,2,4-oxadiazol-3-yl |
| 806 | 1,2,4-triazol-3,-yl |
| 807 | 1-CH₃-1,2,4-triazol-3-yl |
| 808 | 3-fluoropyridin-2-yl |
| 809 | 3-chloropyridin-2-yl |
| 810 | 3-bromopyridin-2-yl |
| 811 | 3-methylpyridin-2-yl |
| 812 | 3-trifluoromethylpyridin-2-yl |
| 813 | 3-methoxypyridin-2-yl |
| 814 | 4-fluoropyridin-2-yl |
| 815 | 4-chloropyridin-2-yl |
| 816 | 4-bromopyridin-2-yl |
| 817 | 4-methylpyridin-2-yl |
| 818 | 4-trifluoromethylpyridin-2-yl |
| 819 | 4-methoxypyridin-2-yl |
| 820 | 5-fluoropyridin-2-yl |
| 821 | 5-bromopyridin-2-yl |
| 822 | 6-trifluoromethylpyridin-2-yl |
| 823 | 2-fluoropyridin-3-yl |
| 824 | 2-chloropyridin-3-yl |
| 825 | 2-bromopyridin-3-yl |

TABLE A-continued

| No. | R⁵ |
|---|---|
| 826 | 2-methylpyridin-3-yl |
| 827 | 2-trifluoromethylpyridin-3-yl |
| 828 | 3-methoxypyridin-3-yl |
| 829 | 4-fluoropyridin-3-yl |
| 830 | 4-chloropyridin-3-yl |
| 831 | 4-bromopyridin-3-yl |
| 832 | 4-methylpyridin-3-yl |
| 833 | 4-trifluoromethylpyridin-3-yl |
| 834 | 4-methoxypyridin-3-yl |
| 835 | 5-fluoropyridin-3-yl |
| 836 | 5-chloropyridin-3-yl |
| 837 | 5-bromopyridin-3-yl |
| 838 | 5-methylpyridin-3-yl |
| 839 | 5-trifluoromethylpyridin-3-yl |
| 840 | 5-methoxypyridin-3-yl |
| 841 | 6-fluoropyridin-3-yl |
| 842 | 6-bromopyridin-3-yl |
| 843 | 6-trifluoromethylpyridin-3-yl |
| 844 | 2-fluoropyridin-4-yl |
| 845 | 2-chloropyridin-4-yl |
| 846 | 2-bromopyridin-4-yl |
| 847 | 2-methylpyridin-4-yl |
| 848 | 2-trifluoromethylpyridin-4-yl |
| 849 | 2-methoxypyridin-4-yl |
| 850 | 3-fluoropyridin-4-yl |
| 851 | 3-chloropyridin-4-yl |
| 852 | 3-bromopyridin-4-yl |
| 853 | 3-methylpyridin-4-yl |
| 854 | 3-trifluoromethylpyridin-4-yl |
| 855 | 3-methoxypyridin-4-yl |
| 856 | 4-fluoropyrimidin-2-yl |
| 857 | 4-bromopyrimidin-2-yl |
| 858 | 4-trifluoromethylpyrimidin-2-yl |
| 859 | 5-fluoropyrimidin-2-yl |
| 860 | 5-bromopyrimidin-2-yl |
| 861 | 5-trifluoromethylpyrimidin-2-yl |
| 862 | 2-fluoropyrimidin-4-yl |
| 863 | 2-bromopyrimidin-4-yl |
| 864 | 2-trifluoromethylpyrimidin-4-yl |
| 865 | 2-trifluoromethoxypyrimidin-4-yl |
| 866 | 5-fluoropyrimidin-4-yl |
| 867 | 5-chloropyrimidin-4-yl |
| 868 | 5-bromopyrimidin-4-yl |
| 869 | 5-methoxypyrimidin-4-yl |
| 870 | 5-trifluoromethylpyrimidin-4-yl |
| 871 | 5-methylpyrimidin-4-yl |
| 872 | 6-fluoropyrimidin-4-yl |
| 873 | 6-bromopyrimidin-4-yl |
| 874 | 6-trifluoromethylpyrimidin-4-yl |
| 875 | 2-fluoropyrimidin-5-yl |
| 876 | 2-bromopyrimidin-5-yl |
| 877 | 2-trifluoromethylpyrimidin-5-yl |
| 878 | 4-fluoropyrimidin-5-yl |
| 879 | 4-chloropyrimidin-5-yl |
| 880 | 4-bromopyrimidin-5-yl |
| 881 | 4-methylpyrimidin-5-yl |
| 882 | 4-trifluoromethylpyrimidin-5-yl |
| 883 | 3-fluoro-5-trifluoromethylpyridin-2-yl |
| 884 | 3,6-dichloro-5-trifluoromethylpyridin-2-yl |
| 885 | 5,6-dichloro-3-trifluoromethylpyridin-2-yl |
| 886 | 5-chloro-3-trifluoromethylpyridin-2-yl |
| 887 | 3-chloro-5-trifluoromethylpyridin-2-yl |
| 888 | 6-chloro-4-cyanopyridin-2-yl |
| 889 | 3-cyano-5-nitropyridin-2-yl |
| 890 | 2-chloro-6-fluoropyridin-4-yl |
| 891 | 6-chloro-4-fluoropyridin-2-yl |
| 892 | 4,6-difluoropyridin-2-yl |
| 893 | 3,5-dichloro-6-fluoropyridin-2-yl |
| 894 | 6-methoxy-3-nitropyridin-2-yl |
| 895 | 4-cyano-6-fluoropyridin-2-yl |
| 896 | 6-chloro-5-cyanopyridin-2-yl |
| 897 | 6-chloro-3-cyanopyridin-2-y1 |
| 898 | 4-cyano-3,5,6-trifluoropyridin-2-yl |
| 899 | 6-chloro-5-nitropyridin-2-yl |
| 900 | 6-chloro-3-nitropyridin-2-yl |
| 901 | 5-cyano-6-fluoropyridin-2-yl |
| 902 | 3-cyano-6-fluoropyridin-2-yl |
| 903 | 4,6-dicyanopyridin-2-yl |
| 904 | 5-trichloromethylpyridin-2-yl |
| 905 | 5-cyanopyridin-2-yl |
| 906 | 5-bromo-4-trifluoromethylpyridin-2-yl |
| 907 | 3-nitro-5-trifluoromethylpyridin-2-yl |
| 908 | 5-aminopyridin-2-yl |
| 909 | 2,3,5,6-tetrafluoropyridin-4-yl |
| 910 | 5-nitropyridin-2-yl |
| 911 | 4-methyl-5-nitropyridin-2-yl |
| 912 | 5-difluoromethylpyridin-2-yl |
| 913 | 5-fluoromethylpyridin-2-yl |
| 914 | 4,6-difluoropyrimidin-2-yl |
| 915 | 2,6-difluoropyrimidin-4-yl |
| 916 | 2-chloro-6-trichloromethylpyrimidin-4-yl |
| 917 | 2,6-dichloropyrimidin-4-yl |
| 918 | 5-methoxycarbonylpyridin-2-yl |
| 919 | 5-chloro-6-fluoropyridin-2-yl |
| 920 | 5-chloro-6-hydroxypyridin-2-yl |
| 921 | 5-chloro-6-methoxypyridin-2-yl |
| 922 | 5-chloro-6-cyanopyridin-2-yl |
| 923 | 5,6-dichloropyridin-2-yl |
| 924 | 6-bromo-5-chloropyridin-2-yl |
| 925 | 5-bromo-6-fluoropyridin-2-yl |
| 926 | 5-bromo-6-chloropyridin-2-yl |
| 927 | 5-bromo-6-cyanopyridin-2-yl |
| 928 | 5-bromo-6-hydroxypyridin-2-yl |
| 929 | 5-bromo-6-methoxypyridin-2-yl |
| 930 | 5,6-dibromopyridin-2-yl |
| 931 | 4-cyanopyridin-2-yl |
| 932 | 6-cyanopyridin-2-yl |
| 933 | 4-chloro-6-methylpyrimidin-2-yl |
| 934 | 2-chloro-6-fluoropyridin-4-yl |
| 935 | 5-bromo-4-trifluoromethylpyridin-2-yl |
| 936 | 4,5-dichloropyridin-2-yl |
| 937 | 4,5-dibromopyridin-2-yl |
| 938 | 5,6-dichloropyridin-2-yl |
| 939 | 4,6-dichloropyridin-2-yl |
| 940 | 4,6-dibromopyridin-2-yl |
| 941 | 5,6-dibromopyridin-2-yl |
| 942 | 4-bromo-5-chloropyridin-2-yl |
| 943 | 6-bromo-5-chloropyridin-2-yl |
| 944 | 5-bromo-4-chloropyridin-2-yl |
| 945 | 5-bromo-4-chloropyridin-2-yl |
| 946 | 6-bromo-4-chloropyridin-2-yl |
| 947 | 4-bromo-6-chloropyridin-2-yl |
| 948 | 6-chloro-4-methoxypyridin-2-yl |
| 949 | 6-bromo-4-methoxypyridin-2-yl |
| 950 | 6-chloroquinazolin-2-yl |
| 951 | quinazolin-2-yl |
| 952 | 4-cyanopyridin-2-yl |
| 953 | 6-cyanopyridin-2-yl |
| 954 | 5-hydroxymethylpyridin-2-yl |
| 955 | 6-chloro-4-trifluoromethylpyridin-2-yl |
| 956 | 6-chloro-4-trifluoromethylpyridin-2-yl |
| 957 | 6-chloro-4-methylpyridin-2-yl |
| 958 | 2,5-dichloro-6-cyanopyridin-2-yl |
| 959 | 2,5-dichloro-6-carboxypyridin-2-yl |
| 960 | 2,5-dichloro-6-methoxycarbonylpyridin-2-yl |
| 961 | 6-trifluoromethylpyridin-2-yl |
| 962 | 6-methoxycarbonylpyridin-2-yl |
| 963 | 6-carboxypyridin-2-yl |
| 964 | 4-phenoxypyridin-2-yl |
| 965 | 5-phenoxypyridin-2-yl |
| 966 | 6-phenoxypyridin-2-yl |
| 967 | 4-phenoxypyrimidin-4-yl |
| 968 | 4-(4-methylphenoxy)pyrimidin-4-yl |
| 969 | 4-phenoxypyrimidin-2-yl |
| 970 | 4-(2-fluorophenoxy)pyrimidin-2-yl |
| 971 | 4-phenoxypyrimidin-6-yl |
| 972 | 4-(4-chlorophenoxy)pyrimidin-6-yl |
| 973 | 4-(2-pyridyloxy)pyrimidin-6-yl |
| 974 | 4-(6-chloro-2-pyridyloxy)pyrimidin-6-yl |
| 975 | 4-(3-pyridyloxy)pyrimidin-6-yl |
| 976 | 4-(2-methyl-3-pyridyloxy)pyrimidin-6-yl |
| 977 | 4-(4-pyridyloxy)pyrimidin-6-yl |
| 978 | 5-bromo-2-thienyl |
| 979 | 5-nitro-2-thienyl |

TABLE A-continued

| No. | R⁵ |
|---|---|
| 980 | 2-chloro-3-thienyl |
| 981 | 2-bromo-3-thienyl |
| 982 | 1-methyl-3-pyrrolyl |
| 983 | 1-methyl-2-pyrrolyl |
| 984 | 1-benzofuran-2-yl |
| 985 | 1-benzofuran-3-yl |
| 986 | 1-benzothiophen-2-yl |
| 987 | 1-benzothiophen-3-yl |
| 988 | 3-pyrrolyl |
| 989 | 2-pyrrolyl |
| 990 | 3-indolyl |
| 991 | 2-indolyl |
| 992 | 1-methyl-3-indolyl |
| 993 | 1-methyl-2-indolyl |
| 994 | isoxazol-4-yl |
| 995 | isothiazol-4-yl |
| 996 | 1,2-benzisoxazol-3-yl |
| 997 | 1,2-benzisothiazol-3-yl |
| 998 | 1-methylindazol-3-yl |
| 999 | benzoxazol-2-yl |
| 1000 | 5-chlorobenzoxazol-2-yl |
| 1001 | 6-fluorobenzoxazol-2-yl |
| 1002 | benzothiazol-2,yl |
| 1003 | 5-fluorobenzthiazol-2-yl |
| 1004 | 6-fluorobenzthiazol-2-yl |
| 1005 | pyrido[3,2-d]thiazol-2-yl |
| 1006 | (6-chloropyrido)[3,2-,d]thiazol-2-yl |
| 1007 | 1-methyl-1,2,3-triazol-5-yl |
| 1008 | 1-methyl-1,2,3-triazol-4-yl |
| 1009 | 1-methyl-1,2,4-triazol-5-yl |
| 1010 | 1-methyl-1,2,3,4-tetrazol-5-yl |
| 1011 | 2-methyl-1,2,3,4-tetrazol-5-yl |
| 1012 | 5-trifluoromethyl-1,3,4-thiadiazol-2-yl |
| 1013 | 6-chlorobenzoxazol-2-yl |
| 1014 | 5-fluorobenzoxazol-2-yl |
| 1015 | 5-nitrothiazol-2-yl |
| 1016 | 1-CH(CH$_3$)$_2$-pyrrol-3-yl |
| 1017 | 1-C(CH$_3$)$_3$-pyrrol-3-yl |
| 1018 | 1-cyclopropyl-pyrrol-3-yl |
| 1019 | 1-C$_6$H$_5$-pyrrol-3-yl |
| 1020 | 1-(2-CH$_3$-C$_6$H$_4$)-pyrrol-3-yl |
| 1021 | 1-(3-CH$_3$-C$_6$H$_4$)-pyrrol-3-yl |
| 1022 | 1-(4-CH$_3$-C$_6$H$_4$)-pyrrol-3-yl |
| 1023 | 1-(3-OCH$_3$-C$_6$H$_4$)-pyrrol-3-yl |
| 1024 | 1-(4-OCH$_3$-C$_6$H$_4$)-pyrrol-3-yl |
| 1025 | 1-(4-NO$_2$-C$_6$H$_4$)-pyrrol-3-yl |
| 1026 | 1-(3-NO$_2$-C$_6$H$_4$)-pyrrol-3-yl |
| 1027 | 1-(4-CN-C$_6$H$_4$)-pyrrol-3-yl |
| 1028 | 1-(3-CN-C$_6$H$_4$)-pyrrol-3-yl |
| 1029 | 1-(3-CF$_3$-C$_6$H$_4$)-pyrrol-3-yl |
| 1030 | 1-(4-CF$_3$-C$_6$H$_4$)-pyrrol-3-yl |
| 1031 | 1-(4-C(CH$_3$)$_3$-C$_6$H$_4$)-pyrrol-3-yl |
| 1032 | 1-(2-Cl—C$_6$H$_4$)-pyrrol-3-yl |
| 1033 | 1-(3-Cl—C$_6$H$_4$)-pyrrol-3-yl |
| 1034 | 1-(4-Cl—C$_6$H$_4$)-pyrrol-3-yl |
| 1035 | 1-(2-Br—C$_6$H$_4$)-pyrrol-3-yl |
| 1036 | 1-(3-Br—C$_6$H$_4$)-pyrrol-3-yl |
| 1037 | 1-(4-Br—C$_6$H$_4$)-pyrrol-3-yl |
| 1038 | 1-(2-F—C$_6$H$_4$)-pyrrol-3-yl |
| 1039 | 1-(3-F—C$_6$H$_4$)-pyrrol-3-yl |
| 1040 | 1-(4-F—C$_6$H$_4$)-pyrrol-3-yl |
| 1041 | 1-(2,4-Cl$_2$—C$_6$H$_3$)-pyrrol-3-yl |
| 1042 | 1-(2,5-Cl$_2$—C$_6$H$_3$)-pyrrol-3-yl |
| 1043 | 1-(2,6-Cl$_2$—C$_6$H$_3$)-pyrrol-3-yl |
| 1044 | 1-(3,4-Cl$_2$—C$_6$H$_3$)-pyrrol-3-yl |
| 1045 | 1-(2,4-F$_2$—C$_6$H$_3$)-pyrrol-3-yl |
| 1046 | 1-(2,5-F$_2$—C$_6$H$_3$)-pyrrol-3-yl |
| 1047 | 1-(2,6-F$_2$—C$_6$H$_3$)-pyrrol-3-yl |
| 1048 | 1-(3,4-F$_2$—C$_6$H$_3$)-pyrrol-3-yl |
| 1049 | 1-(2-Cl, 5-OCH$_3$—C$_6$H$_3$)-pyrrol-3-yl |
| 1050 | 1-(2-Cl, 5-CH$_3$—C$_6$H$_3$)-pyrrol-3-yl |
| 1051 | 1-(5-Cl, 2-OCH$_3$—C$_6$H$_3$)-pyrrol-3-yl |
| 1052 | 1-(5-Cl, 2-CH$_3$—C$_6$H$_3$)-pyrrol-3-yl |
| 1053 | 1-[2,5-(CH$_3$)$_2$-C$_6$H$_3$]-pyrrol-3-yl |
| 1054 | 1-CH(CH$_3$)$_2$-pyrrol-2-yl |
| 1055 | 1-C(CH$_3$)$_3$-pyrrol-2-yl |
| 1056 | 1-cyclopropyl-pyrrol-2-yl |

TABLE A-continued

| No. | R⁵ |
|---|---|
| 1057 | 1-C$_6$H$_5$-pyrrol-2-yl |
| 1058 | 1-(2-CH$_3$—C$_6$H$_4$)-pyrrol-2-yl |
| 1059 | 1-(3-CH$_3$—C$_6$H$_4$)-pyrrol-2-yl |
| 1060 | 1-(4-CH$_3$—C$_6$H$_4$)-pyrrol-2-yl |
| 1061 | 1-(3-OCH$_3$—C$_6$H$_4$)-pyrrol-2-yl |
| 1062 | 1-(4-OCH$_3$—C$_6$H$_4$)-pyrrol-2-yl |
| 1063 | 1-(4-NO$_2$—C$_6$H$_4$)-pyrrol-2-yl |
| 1064 | 1-(3-NO$_2$—C$_6$H$_4$)-pyrrol-2-yl |
| 1065 | 1-(4-CN—C$_6$H$_4$)-pyrrol-2-yl |
| 1066 | 1-(3-CN—C$_6$H$_4$)-pyrrol-2-yl |
| 1067 | 1-(3-CF$_3$—C$_6$H$_4$)-pyrrol-2-yl |
| 1068 | 1-(4-CF$_3$—C$_6$H$_4$)-pyrrol-2-yl |
| 1069 | 1-(4-C(CH$_3$)$_3$—C$_6$H$_4$)-pyrrol-2-yl |
| 1070 | 1-(2-Cl—C$_6$H$_4$)-pyrrol-2-yl |
| 1071 | 1-(3-Cl—C$_6$H$_4$)-pyrrol-2-yl |
| 1072 | 1-(4-Cl—C$_6$H$_4$)-pyrrol-2-yl |
| 1073 | 1-(2-Br—C$_6$H$_4$)-pyrrol-2-yl |
| 1074 | 1-(3-Br—C$_6$H$_4$)-pyrrol-2-yl |
| 1075 | 1-(4-Br—C$_6$H$_4$)-pyrrol-2-yl |
| 1076 | 1-(2-F—C$_6$H$_4$)-pyrrol-2-yl |
| 1077 | 1-(3-F—C$_6$H$_4$)-pyrrol-2-yl |
| 1078 | 1-(4-F—C$_6$H$_4$)-pyrrol-2-yl |
| 1079 | 1-(2,4-Cl$_2$—C$_6$H$_3$)-pyrrol-2-yl |
| 1080 | 1-(2,5-Cl$_2$—C$_6$H$_3$)-pyrrol-2-yl |
| 1081 | 1-(2,6-Cl$_2$—C$_6$H$_3$)-pyrrol-2-yl |
| 1082 | 1-(3,4-Cl$_2$—C$_6$H$_3$)-pyrrol-2-yl |
| 1083 | 1-(2,4-F$_2$—C$_6$H$_3$)-pyrrol-2-yl |
| 1084 | 1-(2,5-F$_2$—C$_6$H$_3$)-pyrrol-2-yl |
| 1085 | 1-(2,6-F$_2$—C$_6$H$_3$)-pyrrol-2-yl |
| 1086 | 1-(3,4-F$_2$—C$_6$H$_3$)-pyrrol-2-yl |
| 1087 | 1-(2-Cl, 5-OCH$_3$—C$_6$H$_3$)-pyrrol-2-yl |
| 1088 | 1-(2-Cl, 5-CH$_3$—C$_6$H$_3$)-pyrrol-2-yl |
| 1089 | 1-(5-Cl, 2-OCH$_3$—C$_6$H$_3$)-pyrrol-2-yl |
| 1090 | 1-(5-Cl, 2-CH$_3$—C$_6$H$_3$)-pyrrol-2-yl |
| 1091 | 1-[2,5-(CH$_3$)$_2$-C$_6$H$_3$]-pyrrol-2-yl |
| 1092 | 5-CH(CH$_3$)$_2$-furan-2-yl |
| 1093 | 5-C(CH$_3$)$_3$-furan-2-yl |
| 1094 | 5-cyclopropylfuran-2-yl |
| 1095 | 5-C$_6$H$_5$-furan-2-yl |
| 1096 | 5-(2-CH$_3$—C$_6$H$_4$)-furan-2-yl |
| 1097 | 5-(3-CH$_3$—C$_6$H$_4$)-furan-2-yl |
| 1098 | 5-(4-CH$_3$—C$_6$H$_4$)-furan-2-yl |
| 1099 | 5-(3-OCH$_3$—C$_6$H$_4$)-furan-2-yl |
| 1100 | 5-(4-OCH$_3$—C$_6$H$_4$)-furan-2-yl |
| 1101 | 5-(4-NO$_2$—C$_6$H$_4$)-furan-2-yl |
| 1102 | 5-(3-NO$_2$—C$_6$H$_4$)-furan-2-yl |
| 1103 | 5-(4-CN—C$_6$H$_4$)-furan-2-yl |
| 1104 | 5-(3-CN—C$_6$H$_4$)-furan-2-yl |
| 1105 | 5-(3-CF$_3$—C$_6$H$_4$)-furan-2-yl |
| 1106 | 5-(4-CF$_3$—C$_6$H$_4$)-furan-2-yl |
| 1107 | 5-(4-C(CH$_3$)$_3$—C$_6$H$_4$)-furan-2-yl |
| 1108 | 5-(4-C$_6$H$_5$—C$_6$H$_4$)-furan-2-yl |
| 1109 | 5-(2-Cl—C$_6$H$_4$)-furan-2-yl |
| 1110 | 5-(3-Cl—C$_6$H$_4$)-furan-2-yl |
| 1111 | 5-(4-Cl—C$_6$H$_4$)-furan-2-yl |
| 1112 | 5-(2-Br—C$_6$H$_4$)-furan-2-yl |
| 1113 | 5-(3-Br—C$_6$H$_4$)-furan-2-yl |
| 1114 | 5-(4-Br—C$_6$H$_4$)-furan-2-yl |
| 1115 | 5-(2-F—C$_6$H$_4$)-furan-2-yl |
| 1116 | 5-(3-F—C$_6$H$_4$)-furan-2-yl |
| 1117 | 5-(4-F—C$_6$H$_4$)-furan-2-yl |
| 1118 | 5-(2,4-Cl$_2$—C$_6$H$_3$)-furan-2-yl |
| 1119 | 5-(2,5-Cl$_2$—C$_6$H$_3$)-furan-2-yl |
| 1120 | 5-(2,6-Cl$_2$—C$_6$H$_3$)-furan-2-yl |
| 1121 | 5-(3,4-Cl$_2$—C$_6$H$_3$)-furan-2-yl |
| 1122 | 5-(2,4-F$_2$—C$_6$H$_3$)-furan-2-yl |
| 1123 | 5-(2,5-F$_2$—C$_6$H$_3$)-furan-2-yl |
| 1124 | 5-(2,6-F$_2$—C$_6$H$_3$)-furan-2-yl |
| 1125 | 5-(3,4-F$_2$—C$_6$H$_3$)-furan-2-yl |
| 1126 | 5-(2-Cl, 5-OCH$_3$—C$_6$H$_3$)-furan-2-yl |
| 1127 | 5-(2-Cl, 5-CH$_3$—C$_6$H$_3$)-furan-2-yl |
| 1128 | 5-(5-Cl, 2-OCH$_3$—C$_6$H$_3$)-furan-2-yl |
| 1129 | 5-(5-Cl, 2-CH$_3$—C$_6$H$_3$)-furan-2-yl |
| 1130 | 5-[2,5-(CH$_3$)$_2$-C$_6$H$_3$]-furan-2-yl |
| 1131 | 4-CH(CH$_3$)$_2$-furan-2-yl |
| 1132 | 4-C(CH$_3$)$_3$-furan-2-yl |
| 1133 | 4-cyclopropyl-furan-2-yl |

TABLE A-continued

| No. | R⁵ |
|---|---|
| 1134 | 4-C₆H₅-furan-2-yl |
| 1135 | 4-(2-CH₃—C₆H₄)-furan-2-yl |
| 1136 | 4-(3-CH₃—C₆H₄)-furan-2-yl |
| 1137 | 4-(4-CH₃—C₆H₄)-furan-2-yl |
| 1138 | 4-(3-OCH₃—C₆H₄)-furan-2-yl |
| 1139 | 4-(4-OCH₃—C₆H₄)-furan-2-yl |
| 1140 | 4-(4-NO₂—C₆H₄)-furan-2-yl |
| 1141 | 4-(3-NO₂—C₆H₄)-furan-2-yl |
| 1142 | 4-(4-CN—C₆H₄)-furan-2-yl |
| 1143 | 4-(3-CN—C₆H₄)-furan-2-yl |
| 1144 | 4-(3-CF₃—C₆H₄)-furan-2-yl |
| 1145 | 4-(4-CF₃—C₆H₄)-furan-2-yl |
| 1146 | 4-(4-C(CH₃)₃—C₆H₄)-furan-2-yl |
| 1147 | 4-(2-Cl—C₆H₄)-furan-2-yl |
| 1148 | 4-(3-Cl—C₆H₄)-furan-2-yl |
| 1149 | 4-(4-Cl—C₆H₄)-furan-2-yl |
| 1150 | 4-(2-Br—C₆H₄)-furan-2-yl |
| 1151 | 4-(3-Br—C₆H₄)-furan-2-yl |
| 1152 | 4-(4-Br—C₆H₄)-furan-2-yl |
| 1153 | 4-(2-F—C₆H₄)-furan-2-yl |
| 1154 | 4-(3-F—C₆H₄)-furan-2-yl |
| 1155 | 4-(4-F—C₆H₄)-furan-2-yl |
| 1156 | 4-(2,4-Cl₂-C₆H₃)-furan-2-yl |
| 1157 | 4-(2,5-Cl₂—C₆H₃)-furan-2-yl |
| 1158 | 4-(2,6-Cl₂—C₆H₃)-furan-2-yl |
| 1159 | 4-(3,4-Cl₂—C₆H₃)-furan-2-yl |
| 1160 | 4-(2,4-F₂—C₆H₃)-furan-2-yl |
| 1161 | 4-(2,5-F₂—C₆H₃)-furan-2-yl |
| 1162 | 4-(2,6-F₂—C₆H₃)-furan-2-yl |
| 1163 | 4-(3,4-F₂—C₆H₃)-furan-2-yl |
| 1164 | 4-(2-Cl, 5-OCH₃—C₆H₃)-furan-2-yl |
| 1165 | 4-(2-Cl, 5-CH₃—C₆H₃)-furan-2-yl |
| 1166 | 4-(5-Cl, 2-OCH₃—C₆H₃)-furan-2-yl |
| 1167 | 4-(5-Cl, 2-CH₃—C₆H₃)-furan-2-yl |
| 1168 | 4-[2,5-(CH₃)₂—C₆H₃]-furan-2-yl |
| 1169 | 5-CH(CH₃)₂-thien-2-yl |
| 1170 | 5-C(CH₃)3-thien-2-yl |
| 1171 | 5-cyclopropylthien-2-yl |
| 1172 | 5-C₆H₅-thien-2-yl |
| 1173 | 5-(2-CH₃—C₆H₄)-thien-2-yl |
| 1174 | 5-(3-CH₃—C₆H₄)-thien-2-yl |
| 1175 | 5-(4-CH₃—C₆H₄)-thien-2-yl |
| 1176 | 5-(3-OCH₃—C₆H₄)-thien-2-yl |
| 1177 | 5-(4-OCH₃—C₆H₄)-thien-2-yl |
| 1178 | 5-(4-NO₂—C₆H₄)-thien-2-yl |
| 1179 | 5-(3-NO₂—C₆H₄)-thien-2-yl |
| 1180 | 5-(4-CN—C₆H₄)-thien-2-yl |
| 1181 | 5-(3-CN—C₆H₄)-thien-2-yl |
| 1182 | 5-(4-CF₃—C₆H₄)-thien-2-yl |
| 1183 | 5-(4-CF₃—C₆H₄)-thien-2-yl |
| 1184 | 5-(4-C(CH₃)₃—C₆H₄)-thien-2-yl |
| 1185 | 5-(2-Cl—C₆H₄)-thien-2-yl |
| 1186 | 5-(3-Cl—C₆H₄)-thien-2-yl |
| 1187 | 5-(4-Cl—C₆H₄)-thien-2-yl |
| 1188 | 5-(2-Br—C₆H₄)-thien-2-yl |
| 1189 | 5-(3-Br—C₆H₄)-thien-2-yl |
| 1190 | 5-(4-Br—C₆H₄)-thien-2-yl |
| 1191 | 5-(2-F—C₆H₄)-thien-2-yl |
| 1192 | 5-(3-F—C₆H₄)-thien-2-yl |
| 1193 | 5-(4-F—C₆H₄)-thien-2-yl |
| 1194 | 5-(2,4-Cl₂—C₆H₃)-thien-2-yl |
| 1195 | 5-(2,5-Cl₂—C₆H₃)-thien-2-yl |
| 1196 | 5-(2,6-Cl₂—C₆H₃)-thien-2-yl |
| 1197 | 5-(3,4-Cl₂—C₆H₃)-thien-2-yl |
| 1198 | 5-(2,4-F₂—C₆H₃)-thien-2-yl |
| 1199 | 5-(2,5-F₂—C₆H₃)-thien-2-yl |
| 1200 | 5-(2,6-F₂—C₆H₃)-thien-2-yl |
| 1201 | 5-(3,4-F₂—C₆H₃)-thien-2-yl |
| 1202 | 5-(2-Cl, 5-OCH₃—C₆H₃)-thien-2-yl |
| 1203 | 5-(2-Cl, 5-CH₃—C₆H₃)-thien-2-yl |
| 1204 | 5-(5-Cl, 2-OCH₃—C₆H₃)-thien-2-yl |
| 1205 | 5-(5-Cl, 2-CH₃—C₆H₃)-thien-2-yl |
| 1206 | 5-[2,5-(CH₃)₂—C₆H₃]-thien-2-yl |
| 1207 | 4-CH(CH₃)₂-thien-2-yl |
| 1208 | 4-C(CH₃)₃-thien-2-yl |
| 1209 | 4-cyclopropylthien-2-yl |
| 1210 | 4-C₆H₅-thien-2-yl |
| 1211 | 4-(2-CH₃—C₆H₄)-thien-2-yl |
| 1212 | 4-(3-CH₃—C₆H₄)-thien-2-yl |
| 1213 | 4-(4-CH₃—C₆H₄)-thien-2-yl |
| 1214 | 4-(3-OCH₃—C₆H₄)-thien-2-yl |
| 1215 | 4-(4-OCH₃—C₆H₄)-thien-2-y1 |
| 1216 | 4-(4-NO₂—C₆H₄)-thien-2-yl |
| 1217 | 4-(3-NO₂—C₆H₄)-thien-2-yl |
| 1218 | 4-(4-CN—C₆H₄)-thien-2-yl |
| 1219 | 4-(3-CN—C₆H₄)-thien-2-yl |
| 1220 | 4-(3-CF₃—C₆H₄)-thien-2-yl |
| 1221 | 4-(4-CF₃—C₆H₄)-thien-2-yl |
| 1222 | 4-(4-C(CH₃)₃—C₆H₄)-thien-2-yl |
| 1223 | 4-(2-Cl—C₆H₄)-thien-2-yl |
| 1224 | 4-(3-Cl—C₆H₄)-thien-2-yl |
| 1225 | 4-(4-Cl—C₆H₄)-thien-2-yl |
| 1226 | 4-(2-Br—C₆H₄)-thien-2-yl |
| 1227 | 4-(3-Br—C₆H₄)-thien-2-yl |
| 1228 | 4-(4-Br—C₆H₄)-thien-2-yl |
| 1229 | 4-(2-F—C₆H₄)-thien-2-yl |
| 1230 | 4-(3-F—C₆H₄)-thien-2-yl |
| 1231 | 4-(4-F—C₆H₄)-thien-2-yl |
| 1232 | 4-(2,4-Cl₂—C₆H₃)-thien-2-yl |
| 1233 | 4-(2,5-Cl₂—C₆H₃)-thien-2-yl |
| 1234 | 4-(2,6-Cl₂—C₆H₃)-thien-2-yl |
| 1235 | 4-(3,4-Cl₂—C₆H₃)-thien-2-yl |
| 1236 | 4-(2,4-F₂—C₆H₃)-thien-2-yl |
| 1237 | 4-(2,5-F₂—C₆H₃)-thien-2-yl |
| 1238 | 4-(2,6-F₂—C₆H₃)-thien-2-yl |
| 1239 | 4-(3,4-F₂—C₆H₃)-thien-2-yl |
| 1240 | 4-(2-Cl, 5-OCH₃—C₆H₃)-thien-2-yl |
| 1241 | 4-(2-Cl, 5-CH₃—C₆H₃)-thien-2-yl |
| 1242 | 4-(5-Cl, 2-OCH₃—C₆H₃)-thien-2-yl |
| 1243 | 4-(5-Cl, 2-CH₃—C₆H₃)-thien-2-yl |
| 1244 | 4-[2,5-(CH₃)₂—C₆H₃]-thien-2-yl |
| 1245 | 2-CH₃-thien-4-yl |
| 1246 | 2-CH(CH₃)₂-thien-4-yl |
| 1247 | 2-C(CH₃)₃-thien-4-yl |
| 1248 | 2-cyclopropylthien-4-yl |
| 1249 | 2-C₆H₅-thien-4-yl |
| 1250 | 2-(2-CH₃—C₆H₄)-thien-4-yl |
| 1251 | 2-(3-CH₃—C₆H₄)-thien-4-yl |
| 1252 | 2-(4-CH₃—C₆H₄)-thien-4-yl |
| 1253 | 2-(3-OCH₃—C₆H₄)-thien-4-yl |
| 1254 | 2-(4-OCH₃—C₆H₄)-thien-4-yl |
| 1255 | 2-(4-NO₂—C₆H₄)-thien-4-yl |
| 1256 | 2-(3-NO₂—C₆H₄)-thien-4-yl |
| 1257 | 2-(4-CN—C₆H₄)-thien-4-yl |
| 1258 | 2-(3-CN—C₆H₄)-thien-4-yl |
| 1259 | 2-(3-CF₃—C₆H₄)-thien-4-yl |
| 1260 | 2-(4-CF₃—C₆H₄)-thien-4-yl |
| 1261 | 2-(4-C(CH₃)₃—C₆H₄)-thien-4-yl |
| 1262 | 2-(2-Cl—C₆H₄)-thien-4-yl |
| 1263 | 2-(3-Cl—C₆H₄)-thien-4-yl |
| 1264 | 2-(4-Cl—C₆H₄)-thien-4-yl |
| 1265 | 2-(2-Br—C₆H₄)-thien-4-yl |
| 1266 | 2-(3-Br—C₆H₄)-thien-4-yl |
| 1267 | 2-(4-Br—C₆H₄)-thien-4-yl |
| 1268 | 2-(2-F—C₆H₄)-thien-4-yl |
| 1269 | 2-(3-F—C₆H₄)-thien-4-yl |
| 1270 | 2-(4-F—C₆H₄)-thien-4-yl |
| 1271 | 2-(2,4-Cl₂—C₆H₃)-thien-4-yl |
| 1272 | 2-(2,5-Cl₂—C₆H₃)-thien-4-yl |
| 1273 | 2-(2,6-Cl₂—C₆H₃)-thien-4-yl |
| 1274 | 2-(3,4-Cl₂—C₆H₃)-thien-4-yl |
| 1275 | 2-(2,4-F₂—C₆H₃)-thien-4-yl |
| 1276 | 2-(2,5-F₂—C₆H₃)-thien-4-yl |
| 1277 | 2-(2,6-F₂—C₆H₃)-thien-4-yl |
| 1278 | 2-(3,4-F₂—C₆H₃)-thien-4-yl |
| 1279 | 2-(2-Cl, 5-OCH₃—C₆H₃)-thien-4-yl |
| 1280 | 2-(2-Cl, 5-CH₃—C₆H₃)-thien-4-yl |
| 1281 | 2-(5-Cl, 2-OCH₃—C₆H₃)-thien-4-yl |
| 1282 | 2-(5-Cl, 2-CH₃—C₆H₃)-thien-4-yl |
| 1283 | 2-[2,5-(CH₃)₂—C₆H₃]-thien-4-yl |
| 1284 | 1-CH(CH₃)₂-pyrazol-4-yl |
| 1285 | 1-C(CH₃)₃-pyrazol-4-yl |
| 1286 | 1-cyclopropylpyrazol-4-yl |
| 1287 | 1-C₆H₅-pyrazol-4-yl |

TABLE A-continued

| No. | R⁵ |
|---|---|
| 1288 | 1-(2-CH₃—C₆H₄)-pyrazol-4-yl |
| 1289 | 1-(3-CH₃—C₆H₄)-pyrazol-4-yl |
| 1290 | 1-(4-CH₃—C₆H₄)-pyrazol-4-yl |
| 1291 | 1-(3-OCH₃—C₆H₄)-pyrazol-4-yl |
| 1292 | 1-(4-OCH₃—C₆H₄)-pyrazol-4-yl |
| 1293 | 1-(4-NO₂—C₆H₄)-pyrazol-4-yl |
| 1294 | 1-(3-NO₂—C₆H₄)-pyrazol-4-yl |
| 1295 | 1-(4-CN—C₆H₄)-pyrazol-4-yl |
| 1296 | 1-(3-CN—C₆H₄)-pyrazol-4-yl |
| 1297 | 1-(3-CF₃—C₆H₄)-pyrazol-4-yl |
| 1298 | 1-(4-CF₃—C₆H₄)-pyrazol-4-yl |
| 1299 | 1-(4-C(CH₃)₃-C₆H₄)-pyrazol-4-yl |
| 1300 | 1-(2-Cl—C₆H₄)-pyrazol-4-yl |
| 1301 | 1-(3-Cl—C₆H₄)-pyrazol-4-yl |
| 1302 | 1-(4-Cl—C₆H₄)-pyrazol-4-yl |
| 1303 | 1-(2-Br—C₆H₄)-pyrazol-4-yl |
| 1304 | 1-(3-Br—C₆H₄)-pyrazol-4-yl |
| 1305 | 1-(4-Br—C₆H₄)-pyrazol-4-yl |
| 1306 | 1-(2-F—C₆H₄)-pyrazol-4-yl |
| 1307 | 1-(3-F—C₆H₄)-pyrazol-4-yl |
| 1308 | 1-(4-F—C₆H₄)-pyrazol-4-yl |
| 1309 | 1-(2,4-Cl₂—C₆H₃)-pyrazol-4-yl |
| 1310 | 1-(2,5-Cl₂—C₆H₃)-pyrazol-4-yl |
| 1311 | 1-(2,6-Cl₂—C₆H₃)-pyrazol-4-yl |
| 1312 | 1-(3,4-Cl₂—C₆H₃)-pyrazol-4-yl |
| 1313 | 1-(2,4-F₂—C₆H₃)-pyrazol-4-yl |
| 1314 | 1-(2,5-F₂—C₆H₃)-pyrazol-4-yl |
| 1315 | 1-(2,6-F₂—C₆H₃)-pyrazol-4-yl |
| 1316 | 1-(3,4-F₂—C₆H₃)-pyrazol-4-yl |
| 1317 | 1-(2-Cl, 5-OCH₃—C₆H₃)-pyrazol-4-yl |
| 1318 | 1-(2-Cl, 5-CH₃—C₆H₃)-pyrazol-4-yl |
| 1319 | 1-(5-Cl, 2-OCH₃—C₆H₃)-pyrazol-4-yl |
| 1320 | 1-(5-Cl, 2-CH₃—C₆H₃)-pyrazol-4-yl |
| 1321 | 1-[2,5-(CH₃)₂—C₆H₃]-pyrazol-4-yl |
| 1322 | 1-CH(CH₃)₂-pyrazol-3-yl |
| 1323 | 1-C(CH₃)₃-pyrazol-3-yl |
| 1324 | 1-cyclopropylpyrazol-3-yl |
| 1325 | 1-C₆H₅-pyrazol-3-yl |
| 1326 | 1-(2-CH₃—C₆H₄)-pyrazol-3-yl |
| 1327 | 1-(3-CH₃—C₆H₄)-pyrazol-3-yl |
| 1328 | 1-(4-CH₃—C₆H₄)-pyrazol-3-yl |
| 1329 | 1-(3-OCH₃—C₆H₄)-pyrazol-3-yl |
| 1330 | 1-(4-OCH₃—C₆H₄)-pyrazol-3-yl |
| 1331 | 1-(4-NO₂—C₆H₄)-pyrazol-3-yl |
| 1332 | 1-(3-NO₂—C₆H₄)-pyrazol-3-yl |
| 1333 | 1-(4-CN—C₆H₄)-pyrazol-3-yl |
| 1334 | 1-(3-CN—C₆H₄)-pyrazol-3-yl |
| 1335 | 1-(3-CF₃—C₆H₄)-pyrazol-3-yl |
| 1336 | 1-(4-CF₃—C₆H₄)-pyrazol-3-yl |
| 1337 | 1-(4-C(CH₃)₃—C₆H₄)-pyrazol-3-yl |
| 1338 | 1-(2-Cl—C₆H₄)-pyrazol-3-yl |
| 1339 | 1-(3-Cl—C₆H₄)-pyrazol-3-yl |
| 1340 | 1-(4-Cl—C₆H₄)-pyrazol-3-yl |
| 1341 | 1-(2-Br—C₆H₄)-pyrazol-3-yl |
| 1342 | 1-(3-Br—C₆H₄)-pyrazol-3-yl |
| 1343 | 1-(4-Br—C₆H₄)-pyrazol-3-yl |
| 1344 | 1-(2-F—C₆H₄)-pyrazol-3-yl |
| 1345 | 1-(3-F—C₆H₄)-pyrazol-3-yl |
| 1346 | 1-(4-F—C₆H₄)-pyrazol-3-yl |
| 1347 | 1-(2,4-Cl₂—C₆H₃)-pyrazol-3-yl |
| 1348 | 1-(2,5-Cl₂—C₆H₃)-pyrazol-3-yl |
| 1349 | 1-(2,6-Cl₂—C₆H₃)-pyrazol-3-yl |
| 1350 | 1-(3,4-Cl₂—C₆H₃)-pyrazol-3-yl |
| 1351 | 1-(2,4-F₂—C₆H₃)-pyrazol-3-yl |
| 1352 | 1-(2,5-F₂—C₆H₃)-pyrazol-3-yl |
| 1353 | 1-(2,6-F₂—C₆H₃)-pyrazol-3-yl |
| 1354 | 1-(3,4-F₂—C₆H₃)-pyrazol-3-yl |
| 1355 | 1-(2-Cl, 5-OCH₃—C₆H₃)-pyrazol-3-yl |
| 1356 | 1-(2-Cl, 5-CH₃—C₆H₃)-pyrazol-3-yl |
| 1357 | 1-(5-Cl, 2-OCH₃—C₆H₃)-pyrazol-3-yl |
| 1358 | 1-(5-Cl, 2-CH₃—C₆H₃)-pyrazol-3-yl |
| 1359 | 1-[2,5-(CH₃)₂-C₆H₃]-pyrazol-3-yl |
| 1360 | 3-CH(CH₃)₂-isoxazol-5-yl |
| 1361 | 3-C(CH₃)₃-isoxazol-5-yl |
| 1362 | 3-cyclopropylisoxazol-5-yl |
| 1363 | 3-C₆H₅-isoxazol-5-yl |
| 1364 | 3-(2-CH₃—C₆H₄)-isoxazol-5-yl |
| 1365 | 3-(3-CH₃—C₆H₄)-isoxazol-5-yl |
| 1366 | 3-(4-CH₃—C₆H₄)-isoxazol-5-yl |
| 1367 | 3-(3-'OCH₃—C₆H₄)-isoxazol-5-yl |
| 1368 | 3-(4-OCH₃—C₆H₄)-isoxazol-5-yl |
| 1369 | 3-(4-NO₂—C₆H₄)-isoxazol-5-yl |
| 1370 | 3-(3-NO₂—C₆H₄)-isoxazol-5-yl |
| 1371 | 3-(4-CN—C₆H₄)-isoxazol-5-yl |
| 1372 | 3-(3-CN—C₆H₄)-isoxazol-5-yl |
| 1373 | 3-(3-CF₃—C₆H₄)-isoxazol-5-yl |
| 1374 | 3-(4-CF₃—C₆H₄)-isoxazol-5-yl |
| 1375 | 3-(4-C(CH₃)₃—C₆H₄)-isoxazol-5-yl |
| 1376 | 3-(2-Cl—C₆H₄)-isoxazol-5-yl |
| 1377 | 3-(3-Cl—C₆H₄)-isoxazol-5-yl |
| 1378 | 3-(4-Cl—C₆H₄)-isoxazol-5-yl |
| 1379 | 3-(2-Br—C₆H₄)-isoxazol-5-yl |
| 1380 | 3-(3-Br—C₆H₄)-isoxazol-5-yl |
| 1381 | 3-(4-Br—C₆H₄)-isoxazol-5-yl |
| 1382 | 3-(2-F—C₆H₄)-isoxazol-5-yl |
| 1383 | 3-(3-F—C₆H₄)-isoxazol-5-yl |
| 1384 | 3-(4-F—C₆H₄)-isoxazol-5-yl |
| 1385 | 3-(2,4-Cl₂—C₆H₃)-isoxazol-5-yl |
| 1386 | 3-(2,5-Cl₂—C₆H₃)-isoxazol-5-yl |
| 1387 | 3-(2,6-Cl₂—C₆H₃)-isoxazol-5-yl |
| 1388 | 3-(3,4-Cl₂—C₆H₃)-isoxazol-5-yl |
| 1389 | 3-(2,4-F₂—C₆H₃)-isoxazol-5-yl |
| 1390 | 3-(2,5-F₂—C₆H₃)-isoxazol-5-yl |
| 1391 | 3-(2,6-F₂—C₆H₃)-isoxazol-5-yl |
| 1392 | 3-(3,4-F₂—C₆H₃)-isoxazol-5-yl |
| 1393 | 3-(2-Cl, 5-OCH₃—C₆H₃)-isoxazol-5-yl |
| 1394 | 3-(2-Cl, 5-CH₃—C₆H₃)-isoxazol-5-yl |
| 1395 | 3-(5-Cl, 2-OCH₃—C₆H₃)-isoxazol-5-yl |
| 1396 | 3-(5-Cl, 2-CH₃—C₆H₃)-isoxazol-5-yl |
| 1397 | 3-[2,5-(CH₃)₂—C₆H₃]-isoxazol-5-yl |
| 1398 | 5-CH(CH₃)₂-isoxazol-3-yl |
| 1399 | 5-C(CH₃)₃-isoxazol-3-yl |
| 1400 | 5-cyclopropylisoxazol-3-yl |
| 1401 | 5-C₆H₅-isoxazol-3-yl |
| 1402 | 5-(2-CH₃—C₆H₄)-isoxazol-3-yl |
| 1403 | 5-(3-CH₃—C₆H₄)-isoxazol-3-yl |
| 1404 | 5-(4-CH₃—C₆H₄)-isoxazol-3-yl |
| 1405 | 5-(3-OCH₃—C₆H₄)-isoxazol-3-yl |
| 1406 | 5-(4-OCH₃—C₆H₄)-isoxazol-3-yl |
| 1407 | 5-(4-NO₂—C₆H₄)-isoxazol-3-yl |
| 1408 | 5-(3-NO₂—C₆H₄)-isoxazol-3-yl |
| 1409 | 5-(4-CN-C₆H₄)-isoxazol-3-yl |
| 1410 | 5-(3-CN-C₆H₄)-isoxazol-3-yl |
| 1411 | 5-(3-CF₃—C₆H₄)-isoxazol-3-yl |
| 1412 | 5-(4-CF₃—C₆H₄)-isoxazol-3-yl |
| 1413 | 5-(4-C(CH₃)₃—C₆H₄)-isoxazol-3-yl |
| 1414 | 5-(2-Cl—C₆H₄)-isoxazol-3-yl |
| 1415 | 5-(3-Cl—C₆H₄)-isoxazol-3-yl |
| 1416 | 5-(4-Cl—C₆H₄)-isoxazol-3-yl |
| 1417 | 5-(2-Br—C₆H₄)-isoxazol-3-yl |
| 1418 | 5-(3-Br—C₆H₄)-3-yl |
| 1419 | 5-(4-Br—C₆H₄)-isoxazol-3-yl |
| 1420 | 5-(2-F—C₆H₄)-isoxazol-3-yl |
| 1421 | 5-(3-F—C₆H₄)-isoxazol-3-yl |
| 1422 | 5-(4-F—C₆H₄)-isoxazol-3-yl |
| 1423 | 5-(2,4-Cl₂—C₆H₃)-isoxazol-3-yl |
| 1424 | 5-(2,5-Cl₂—C₆H₃)-isoxazol-3-yl |
| 1425 | 5-(2,6-Cl₂—C₆H₃)-isoxazol-3-yl |
| 1426 | 5-(3,4-Cl₂—C₆H₃)-isoxazol-3-yl |
| 1427 | 5-(2,4-F₂—C₆H₃)-isoxazol-3-yl |
| 1428 | 5-(2,5-F₂—C₆H₃)-isoxazol-3-yl |
| 1429 | 5-(2,6-F₂—C₆H₃)-isoxazol-3-yl |
| 1430 | 5-(3,4-F₂—C₆H₃)-isoxazol-3-yl |
| 1431 | 5-(2-Cl, 5-OCH₃—C₆H₃)-isoxazol-3-yl |
| 1432 | 5-(2-Cl, 5-CH₃—C₆H₃)-isoxazol-3-yl |
| 1433 | 5-(5-Cl, 2-OCH₃—C₆H₃)-isoxazol-3-yl |
| 1434 | 5-(5-Cl, 2-CH₃—C₆H₃)-isoxazol-3-yl |
| 1435 | 5-[2,5-(CH₃)₂—C₆H₃]-isoxazol-3-yl |
| 1436 | 3-CH(CH₃)₂-isothiazol-5-yl |
| 1437 | 3-C(CH₃)₃-isothiazol-5-yl |
| 1438 | 3-cyclopropylisothiazol-5-yl |
| 1439 | 3-C₆H₅-isothiazol-5-yl |
| 1440 | 3-(2-CH₃—C₆H₄)-isothiazol-5-yl |
| 1441 | 3-(3-CH₃—C₆H₄)-isothiazol-5-yl |

TABLE A-continued

| No. | R⁵ |
|---|---|
| 1442 | 3-(4-CH₃—C₆H₄)-isothiazol-5-yl |
| 1443 | 3-(3-OCH₃—C₆H₄)-isothiazol-5-yl |
| 1444 | 3-(4-OCH₃—C₆H₄)-isothiazol-5-yl |
| 1445 | 3-(4-NO₂—C₆H₄)-isothiazol-5-yl |
| 1446 | 3-(3-NO₂—C₆H₄)-isothiazol-5-yl |
| 1447 | 3-(4-CN—C₆H₄)-isothiazol-5-yl |
| 1448 | 3-(3-CN—C₆H₄)-isothiazol-5-yl |
| 1449 | 3-(3-CF₃—C₆H₄)-isothiazol-5-yl |
| 1450 | 3-(4-CF₃—C₆H₄)-isothiazol-5-yl |
| 1451 | 3-(4-C(CH₃)₃—C₆H₄)-isothiazol-5-yl |
| 1452 | 3-(2-Cl—C₆H₄)-isothiazol-5-yl |
| 1453 | 3-(3-Cl—C₆H₄)-isothiazol-5-yl |
| 1454 | 3-(4-Cl—C₆H₄)-isothiazol-5-yl |
| 1455 | 3-(2-Br—C₆H₄)-isothiazol-5-yl |
| 1456 | 3-(3-Br—C₆H₄)-isothiazol-5-yl |
| 1457 | 3-(4-Br—C₆H₄)-isothiazol-5-yl |
| 1458 | 3-(2-F—C₆H₄)-isothiazol-5-yl |
| 1459 | 3-(3-F—C₆H₄)-isothiazol-5-yl |
| 1460 | 3-(4-F—C₆H₄)-isothiazol-5-yl |
| 1461 | 3-(2,4-Cl₂—C₆H₃)-isothiazol-5-yl |
| 1462 | 3-(2,5-Cl₂—C₆H₃)-isothiazol-5-yl |
| 1463 | 3-(2,6-Cl₂—C₆H₃)-isothiazol-5-yl |
| 1464 | 3-(3,4-Cl₂—C₆H₃)-isothiazol-5-yl |
| 1465 | 3-(2,4-F₂—C₆H₃)-isothiazol-5-yl |
| 1466 | 3-(2,5-F₂—C₆H₃)-isothiazol-5-yl |
| 1467 | 3-(2,6-F₂—C₆H₃)-isothiazol-5-yl |
| 1468 | 3-(3,4-F₂—C₆H₃)-isothiazol-5-yl |
| 1469 | 3-(2-Cl, 5-OCH₃—C₆H₃)-isothiazol-5-yl |
| 1470 | 3-(2-Cl, 5-CH₃—C₆H₃)-isothiazol-5-yl |
| 1471 | 3-(5-Cl, 2-OCH₃—C₆H₃)-isothiazol-5-yl |
| 1472 | 3-(5-Cl, 2-CH₃-C₆H₃)-isothiazol-5-yl |
| 1473 | 3-[2,5-(CH₃)₂-C₆H₃]-isothiazol-5-yl |
| 1474 | 2-CH(CH₃)₂-oxazol-4-yl |
| 1475 | 2-C(CH₃)₃-oxazol-4-yl |
| 1476 | 2-cyclopropyloxazol-4-yl |
| 1477 | 2-C₆H₅-oxazol-4-yl |
| 1478 | 2-(2-CH₃—C₆H₄)-oxazol-4-yl |
| 1479 | 2-(3-CH₃—C₆H₄)-oxazol-4-yl |
| 1480 | 2-(4-CH₃—C₆H₄)-oxazol-4-yl |
| 1481 | 2-(3-OCH₃—C₆H₄)-oxazol-4-yl |
| 1482 | 2-(4-OCH₃—C₆H₄)-oxazol-4-yl |
| 1483 | 2-(4-NO₂—C₆H₄)-oxazol-4-yl |
| 1484 | 2-(3-NO₂—C₆H₄)-oxazol-4-yl |
| 1485 | 2-(4-CN—C₆H₄)-oxazol-4-yl |
| 1486 | 2-(3-CN—C₆H₄)-oxazol-4-yl |
| 1487 | 2-(3-CF₃—C₆H₄)-oxazol-4-yl |
| 1488 | 2-(4-CF₃—C₆H₄)-oxazol-4-yl |
| 1489 | 2-(4-C(CH₃)₃—C₆H₄)-oxazol-4-yl |
| 1490 | 2-(2-Cl—C₆H₄)-oxazol-4-yl |
| 1491 | 2-(3-Cl—C₆H₄)-oxazol-4-yl |
| 1492 | 2-(4-Cl—C₆H₄)-oxazol-4-yl |
| 1493 | 2-(2-Br—C₆H₄)-oxazol-4-yl |
| 1494 | 2-(3-Br—C₆H₄)-oxazol-4-yl |
| 1495 | 2-(4-Br—C₆H₄)-oxazol-4-yl |
| 1496 | 2-(2-F—C₆H₄)-oxazol-4-yl |
| 1497 | 2-(3-F—C₆H₄)-oxazol-4-yl |
| 1498 | 2-(4-F—C₆H₄)-oxazol-4-yl |
| 1499 | 2-(2,4-Cl₂—C₆H₃)-oxazol-4-yl |
| 1500 | 2-(2,5-Cl₂—C₆H₃)-oxazol-4-yl |
| 1501 | 2-(2,6-Cl₂—C₆H₃)-oxazol-4-yl |
| 1502 | 2-(3,4-Cl₂—C₆H₃)-oxazol-4-yl |
| 1503 | 2-(2,4-F₂—C₆H₃)-oxazol-4-yl |
| 1504 | 2-(2,5-F₂—C₆H₃)-oxazol-4-yl |
| 1505 | 2-(2,6-F₂—C₆H₃)-oxazol-4-yl |
| 1506 | 2-(3,4-F₂—C₆H₃)-oxazol-4-yl |
| 1507 | 2-(2-Cl, 5-OCH₃—C₆H₃)-oxazol-4-yl |
| 1508 | 2-(2-Cl, 5-CH₃—C₆H₃)-oxazol-4-yl |
| 1509 | 2-(5-Cl, 2-OCH₃—C₆H₃)-oxazol-4-yl |
| 1510 | 2-(5-Cl, 2-CH₃—C₆H₃)-oxazol-4-yl |
| 1511 | 2-[2,5-(CH₃)₂—C₆H₃]-oxazol-4-yl |
| 1512 | 2-CH(CH₃)₂-thiazol-4-yl |
| 1513 | 2-C(CH₃)₃-thiazol-4-yl |
| 1514 | 2-cyclopropylthiazol-4-yl |
| 1515 | 2-C₆H₅-thiazol-4-yl |
| 1516 | 2-(2-CH₃—C₆H₄)-thiazol-4-yl |
| 1517 | 2-(3-CH₃—C₆H₄) thiazol-4-yl |
| 1518 | 2-(4-CH₃—C₆H₄)-thiazol-4-yl |
| 1519 | 2-(3-OCH₃—C₆H₄)-thiazol-4-yl |
| 1520 | 2-(4-OCH₃—C₆H₄)-thiazol-4-yl |
| 1521 | 2-(4-NO₂—C₆H₄)-thiazol-4-yl |
| 1522 | 2-(3-NO₂—C₆H₄)-thiazol-4-yl |
| 1523 | 2-(4-CN—C₆H₄)-thiazol-4-yl |
| 1524 | 2-(3-CN—C₆H₄)-thiazol-4-yl |
| 1525 | 2-(3-CF₃—C₆H₄)-thiazol-4-yl |
| 1526 | 2-(4-CF₃—C₆H₄)-thiazol-4-yl |
| 1527 | 2-(4-C(CH₃)₃—C₆H₄)-thiazol-4-yl |
| 1528 | 2-(2-Cl—C₆H₄)-thiazol-4-yl |
| 1529 | 2-(3-Cl—C₆H₄)-thiazol-4-yl |
| 1530 | 2-(4-Cl—C₆H₄)-thiazol-4-yl |
| 1531 | 2-(2-Br—C₆H₄)-thiazol-4-yl |
| 1532 | 2-(3-Br—C₆H₄)-thiazol-4-yl |
| 1533 | 2-(4-Br—C₆H₄)-thiazol-4-yl |
| 1534 | 2-(2-F—C₆H₄)-thiazol-4-yl |
| 1535 | 2-(3-F—C₆H₄)-thiazol-4-yl |
| 1536 | 2-(4-F—C₆H₄)-thiazol-4-yl |
| 1537 | 2-(2,4-Cl₂—C₆H₃)-thiazol-4-yl |
| 1538 | 2-(2,5-Cl₂—C₆H₃)-thiazol-4-yl |
| 1539 | 2-(2,6-Cl₂—C₆H₃)-thiazol-4-yl |
| 1540 | 2-(3,4-Cl₂—C₆H₃)-thiazol-4-yl |
| 1541 | 2-(2,4-F₂—C₆H₃)-thiazol-4-yl |
| 1542 | 2-(2,5-F₂—C₆H₃)-thiazol-4-yl |
| 1543 | 2-(2,6-F₂—C₆H₃)-thiazol-4-yl |
| 1544 | 2-(3,4-F₂—C₆H₃)-thiazol-4-yl |
| 1545 | 2-(2-Cl, 5-OCH₃—C₆H₃)-thiazol-4-yl |
| 1546 | 2-(2-Cl, 5-CH₃—C₆H₃)-thiazol-4-yl |
| 1547 | 2-(5-Cl, 2-OCH₃—C₆H₃)-thiazol-4-yl |
| 1548 | 2-(5-Cl, 2-CH₃—C₆H₃)-thiazol-4-yl |
| 1549 | 2-[2,5-(CH₃)₂—C₆H₃]-thiazol-4-yl |
| 1550 | 1,3-(CH₃)₂-1,2,4-triazol-5-yl |
| 1551 | 1-CH(CH₃)₂-1,2,4-triazol-3-yl |
| 1552 | 1-C(CH₃)₃.1,2,4-triazol-3-yl |
| 1553 | 1-cyclopropyl-1,2,4-triazol-3-yl |
| 1554 | 1-C₆H₅-1,2,4-triazol-3-yl |
| 1555 | 1-(2-CH₃.C₆H₄)-1,2,4-triazol-3-yl |
| 1556 | 1-(3-CH₃—C₆H₄)-1,2,4-triazol-3-yl |
| 1557 | 1-(4-CH₃.C₆H₄)-1,2,4-triazol-3-yl |
| 1558 | 1-(3-OCH₃.C₆H₄)-1,2,4-triazol-3-yl |
| 1559 | 1-(4-OCH₃—C₆H₄)-1,2,4-triazol-3-yl |
| 1560 | 1-(4-NO₂—C₆H₄)-1,2,4-triazol-3-yl |
| 1561 | 1-(3-NO₂—C₆H₄)-1,2,4-triazol-3-yl |
| 1562 | 1-(4-CN—C₆H₄)-1,2,4-triazol-3-yl |
| 1563 | 1-(3-CN—C₆H₄)-1,2,4-triazol-3-yl |
| 1564 | 1-(3-CF₃.C₆H₄)-1,2,4-triazol-3-yl |
| 1565 | 1-(4-CF₃.C₆H₄)-1,2,4-triazol-3-yl |
| 1566 | 1-(4-C(CH₃)₃.C₆H₄)-1,2,4-triazol-3-yl |
| 1567 | 1-(4-C₆H₅—C₆H₄)-1,2,4-triazol-3-yl |
| 1568 | 1-(2-Cl—C₆H₄)-1,2,4-triazol-3-yl |
| 1569 | 1-(3-Cl—C₆H₄)-1,2,4-triazol-3-yl |
| 1570 | 1-(4-Cl—C₆H₄)-1,2,4-triazol-3-yl |
| 1571 | 1-(2-Br—C₆H₄)-1,2,4-triazol-3-yl |
| 1572 | 1-(3-Br—C₆H₄)-1,2,4-triazol-3-yl |
| 1573 | 1-(4-Br—C₆H₄)-1,2,4-triazol-3-yl |
| 1574 | 1-(2-F—C₆H₄)-1,2,4-triazol-3-yl |
| 1575 | 1-(3-F—C₆H₄)-1,2,4-triazol-3-yl |
| 1576 | 1-(4-F—C₆H₄)-1,2,4-triazol-3-yl |
| 1577 | 1-(2,4-Cl₂—C₆H₃)-1,2,4-triazol-3-yl |
| 1578 | 1-(2,5-Cl₂—C₆H₃)-1,2,4-triazol-3-yl |
| 1579 | 1-(2,6-Cl₂—C₆H₃)-1,2,4-triazol-3-yl |
| 1580 | 1-(3,4-Cl₂—C₆H₃)-1,2,4-triazol-3-yl |
| 1581 | 1-(2,4-F₂—C₆H₃)-1,2,4-triazol-3-yl |
| 1582 | 1-(2,5-F₂—C₆H₃)-1,2,4-triazol-3-yl |
| 1583 | 1-(2,6-F₂—C₆H₃)-1,2,4-triazol-3-yl |
| 1584 | 1-(3,4-F₂—C₆H₃)-1,2,4-triazol-3-yl |
| 1585 | 1-(2-Cl, 5-OCH₃.C₆H₃)-1,2,4-triazol-3-yl |
| 1586 | 1-(2-Cl, 5-CH₃—C₆H₃)-1,2,4-triazol-3-yl |
| 1587 | 1-(5-Cl, 2-OCH₃—C₆H₃)-1,2,4-triazol-3-yl |
| 1588 | 1-(5-Cl, 2-CH₃—C₆H₃)-1,2,4-triazol-3-yl |
| 1589 | 1-[2,5-(CH₃)₂-C₆H₃]-1,2,4-triazol-3-yl |
| 1590 | 5-C(CH₃)₃.1,3,4-oxadiazol-2-yl |
| 1591 | 5-cyclopropyl-1,3,4-oxadiazol-2-yl |
| 1592 | 5-C₆H₅-1,3,4-oxadiazol-2-yl |
| 1593 | 5-(2-CH₃.C₆H₄)-1,3,4-oxadiazol-2-yl |
| 1594 | 5-(3-CH₃.C₆H₄)-1,3,4-oxadiazol-2-yl |
| 1595 | 5-(4-CH₃.C₆H₄)-1,3,4-oxadiazol-2-yl |

TABLE A-continued

| No. | R⁵ |
|---|---|
| 1596 | 5-(3-OCH₃.C₆H₄)-1,3,4-oxadiazol-2-yl |
| 1597 | 5-(4-OCH₃.C₆H₄)-1,3,4-oxadiazol-2-yl |
| 1598 | 5-(4-NO₂—C₆H₄)-1,3,4-oxadiazol-2-yl |
| 1599 | 5-(3-NO₂—C₆H₄)-1,3,4-oxadiazol-2-yl |
| 1600 | 5-(4-CN—C₆H₄)-1,3,4-oxadiazol-2-yl |
| 1601 | 5-(3-CN—C₆H₄)-1,3,4-oxadiazol-2-yl |
| 1602 | 5-(3-CF₃.C₆H₄)-1,3,4-oxadiazol-2-yl |
| 1603 | 5-(4-CF₃.C₆H₄)-1,3,4-oxadiazol-2-yl |
| 1604 | 5-(4-C(CH₃)₃.C₆H₄)-1,3,4-oxadiazol-2-yl |
| 1605 | 5-(2-Cl—C₆H₄)-1,3,4-oxadiazol-2-yl |
| 1606 | 5-(3-Cl—C₆H₄)-1,3,4-oxadiazol-2-yl |
| 1607 | 5-(4-Cl—C₆H₄)-1,3,4-oxadiazol-2-yl |
| 1608 | 5-(2-Br—C₆H₄)-1,3,4-oxadiazol-2-yl |
| 1609 | 5-(3-Br—C₆H₄)-1,3,4-oxadiazol-2-yl |
| 1610 | 5-(4-Br—C₆H₄)-1,3,4-oxadiazol-2-yl |
| 1611 | 5-(2-F—C₆H₄)-1,3,4-oxadiazol-2-yl |
| 1612 | 5-(3-F—C₆H₄)-1,3,4-oxadiazol-2-yl |
| 1613 | 5-(4-F—C₆H₄)-1,3,4-oxadiazol-2-yl |
| 1614 | 5-(2,4-Cl₂—C₆H₃)-1,3,4-oxadiazol-2-yl |
| 1615 | 5-(2,5-Cl₂—C₆H₃)-1,3,4-oxadiazol-2-yl |
| 1616 | 5-(2,6-Cl₂—C₆H₃)-1,3,4-oxadiazol-2-yl |
| 1617 | 5-(3,4-Cl₂—C₆H₃)-1,3,4-oxadiazol-2-yl |
| 1618 | 5-(2,4-F₂—C₆H₃)-1,3,4-oxadiazol-2-yl |
| 1619 | 5-(2,5-F₂—C₆H₃)-1,3,4-oxadiazol-2-yl |
| 1620 | 5-(2,6-F₂—C₆H₃)-1,3,4-oxadiazol-2-yl |
| 1621 | 5-(3,4-F₂—C₆H₃)-1,3,4-oxadiazol-2-yl |
| 1622 | 5-(2-Cl, 5-OCH₃.C₆H₃)-1,3,4-oxadiazol-2-yl |
| 1623 | 5-(2-Cl, 5-CH₃.C₆H₃)-1,3,4-oxadiazol-2-yl |
| 1624 | 5-(5-Cl, 2-OCH₃.C₆H₃)-1,3,4-oxadiazol-2-yl |
| 1625 | 5-(5-Cl, 2-CH₃.C₆H₃)-1,3,4-oxadiazol-2-yl |
| 1626 | 5-[2,5-(CH₃)₂—C₆H₃]-1,3,4-oxadiazol-2-yl |
| 1627 | 5-C(CH₃)₃.1,2,4-oxadiazol-3-1 |
| 1628 | 5-cyclopropyl-1,2,4-oxadiazol-3-yl |
| 1629 | 5-C₆H₅.1,2,4-oxadiazol-3-yl |
| 1630 | 5-(2-CH₃.C₆H₄)-1,2,4-oxadiazol-3-yl |
| 1631 | 5-(3-CH₃.C₆H₄)-1,2,4-oxadiazol-3-yl |
| 1632 | 5-(4-CH₃.C₆H₄)-1,2,4-oxadiazol-3-yl |
| 1633 | 5-(3-OCH₃.C₆H₄)-1,2,4-oxadiazol-3-yl |
| 1634 | 5-(4-OCH₃.C₆H₄)-1,2,4-oxadiazol-3-yl |
| 1635 | 5-(4-NO₂—C₆H₄)-1,2,4-oxadiazol-3-yl |
| 1636 | 5-(3-NO₂—C₆H₄)-1,2,4-oxadiazol-3-yl |
| 1637 | 5-(4-CN—C₆H₄)-1,2,4-oxadiazol-3-yl |
| 1638 | 5-(3-CN—C₆H₄)-1,2,4-oxadiazol-3-yl |
| 1639 | 5-(3-CF₃.C₆H₄)-1,2,4-oxadiazol-3-yl |
| 1640 | 5-(4-CF₃.C₆H₄)-1,2,4-oxadiazol-3-yl |
| 1641 | 5-(4-C(CH₃)₃.C₆H₄)-1,2,4-oxadiazol-3-yl |
| 1642 | 5-(2-Cl—C₆H₄)-1,2,4-oxadiazol-3-yl |
| 1643 | 5-(3-Cl—C₆H₄)-1,2,4-oxadiazol-3-yl |
| 1644 | 5-(4-Cl—C₆H₄)-1,2,4-oxadiazol-3-yl |
| 1645 | 5-(2-Br—C₆H₄)-1,2,4-oxadiazol-3-yl |
| 1646 | 5-(3-Br—C₆H₄)-1,2,4-oxadiazol-3-yl |
| 1647 | 5-(4-Br—C₆H₄)-1,2,4-oxadiazol-3-yl |
| 1648 | 5-(2-F—C₆H₄)-1,2,4-oxadiazol-3-yl |
| 1649 | 5-(3-F—C₆H₄)-1,2,4-oxadiazol-3-yl |
| 1650 | 5-(4-F—C₆H₄)-1,2,4-oxadiazol-3-yl |
| 1651 | 5-(2,4-Cl₂—C₆H₃)-1,2,4-oxadiazol-3-yl |
| 1652 | 5-(2,5-Cl₂—C₆H₃)-1,2,4-oxadiazol-3-yl |
| 1653 | 5-(2,6-Cl₂—C₆H₃)-1,2,4-oxadiazol-3-yl |
| 1654 | 5-(3,4-Cl₂—C₆H₃)-1,2,4-oxadiazol-3-yl |
| 1655 | 5-(2,4-F₂—C₆H₃)-1,2,4-oxadiazol-3-yl |
| 1656 | 5-(2,5-F₂—C₆H₃)-1,2,4-oxadiazol-3-yl |
| 1657 | 5-(2,6-F₂—C₆H₃)-1,2,4-oxadiazol-3-yl |
| 1658 | 5-(3,4-F₂—C₆H₃)-1,2,4-oxadiazol-3-yl |
| 1659 | 5-(2-Cl, 5-OCH₃.C₆H₃)-1,2,4-oxadiazol-3-yl |
| 1660 | 5-(2-Cl, 5-CH₃.C₆H₃)-1,2,4-oxadiazol-3-yl |
| 1661 | 5-(5-Cl, 2-OCH₃.C₆H₃)-1,2,4-oxadiazol-3-yl |
| 1662 | 5-(5-Cl, 2-CH₃.C₆H₃)-1,2,4-oxadiazol-3-yl |
| 1663 | 5-[2,5-(CH₃)₂—C₆H₃]-1,2,4-oxadiazol-3-yl |
| 1664 | 3-CH₃.1,2,4-oxadiazol-5-yl |
| 1665 | 3-CH(CH₃)₂-1,2,4-oxadiazol-5-yl |
| 1666 | 3-C(CH₃)₃.1,2,4-oxadiazol-5-yl |
| 1667 | 3-cyclopropyl-1,2,4-oxadiazol-5-yl |
| 1668 | 3-C₆H₅-1,2,4-oxadiazol-5-yl |
| 1669 | 3-(2-CH₃.C₆H₄)-1,2,4-oxadiazol-5-yl |
| 1670 | 3-(3-CH₃.C₆H₄)-1,2,4-oxadiazol-5-yl |
| 1671 | 3-(4-CH₃.C₆H₄)-1,2,4-oxadiazol-5-yl |
| 1672 | 3-(3-OCH₃.C₆H₄)-1,2,4-oxadiazol-5-yl |
| 1673 | 3-(4-OCH₃.C₆H₄)-1,2,4-oxadiazol-5-yl |
| 1674 | 3-(4-NO₂—C₆H₄)-1,2,4-oxadiazol-5-yl |
| 1675 | 3-(3-NO₂—C₆H₄)-1,2,4-oxadiazol-5-yl |
| 1676 | 3-(4-CN—C₆H₄)-1,2,4-oxadiazol-5-yl |
| 1677 | 3-(3-CN—C₆H₄)-1,2,4-oxadiazol-5-yl |
| 1678 | 3-(3-CF₃.C₆H₄)-1,2,4-oxadiazol-5-yl |
| 1679 | 3-(4-CF₃.C₆H₄)-1,2,4-oxadiazol-5-yl |
| 1680 | 3-(4-C(CH₃)₃.C₆H₄)-1,2,4-oxadiazol-5-yl |
| 1681 | 3-(2-Cl—C₆H₄)-1,2,4-oxadiazol-5-yl |
| 1682 | 3-(3-Cl—C₆H₄)-1,2,4-oxadiazol-5-yl |
| 1683 | 3-(4-Cl—C₆H₄)-1,2,4-oxadiazol-5-yl |
| 1684 | 3-(2-Br—C₆H₄)-1,2,4-oxadiazol-5-yl |
| 1685 | 3-(3-Br—C₆H₄)-1,2,4-oxadiazol-5-yl |
| 1686 | 3-(4-Br—C₆H₄)-1,2,4-oxadiazol-5-yl |
| 1687 | 3-(2-F—C₆H₄)-1,2,4-oxadiazol-5-yl |
| 1688 | 3-(3-F—C₆H₄)-1,2,4-oxadiazol-5-yl |
| 1689 | 3-(4-F—C₆H₄)-1,2,4-oxadiazol-5-yl |
| 1690 | 3-(2,4-Cl₂—C₆H₃)-1,2,4-oxadiazol-5-yl |
| 1691 | 3-(2,5-Cl₂—C₆H₃)-1,2,4-oxadiazol-5-yl |
| 1692 | 3-(2,6-Cl₂—C₆H₃)-1,2,4-oxadiazol-5-yl |
| 1693 | 3-(3,4-Cl₂—C₆H₃)-1,2,4-oxadiazol-5-yl |
| 1694 | 3-(2,4-F₂—C₆H₃)-1,2,4-oxadiazol-5-yl |
| 1695 | 3-(2,5-F₂—C₆H₃)-1,2,4-oxadiazol-5-yl |
| 1696 | 3-(2,6-F₂—C₆H₃)-1,2,4-oxadiazol-5-yl |
| 1697 | 3-(3,4-F₂—C₆H₃)-1,2,4-oxadiazol-5-yl |
| 1698 | 3-(2-Cl, 5-OCH₃.C₆H₃)-1,2,4-oxadiazol-5-yl |
| 1699 | 3-(2-Cl, 5-CH₃.C₆H₃)-1,2,4-oxadiazol-5-yl |
| 1700 | 3-(5-Cl, 2-OCH₃.C₆H₃)-1,2,4-oxadiazol-5-yl |
| 1701 | 3-(5-Cl, 2-CH₃.C₆H₃)-1,2,4-oxadiazol-5-yl |
| 1702 | 3-[2,5-(CH₃)₂—C₆H₃]-1,2,4-oxadiazol-5-yl |
| 1703 | 5-CH₃.1,2,4-thiadiazol-3-yl |
| 1704 | 5-CH(CH₃)₂-1,2,4-thiadiazol-3-yl |
| 1705 | 5-C(CH₃)₃-1,2,4-thiadiazol-3-yl |
| 1706 | 5-cyclopropyl-1,2,4-thiadiazol-3-yl |
| 1707 | 5-C₆H₅-1,2,4-thiadiazol-3-yl |
| 1708 | 5-(2-CH₃.C₆H₄)-1,2,4-thiadiazol-3-yl |
| 1709 | 5-(3-CH₃.C₆H₄)-1,2,4-thiadiazol-3-yl |
| 1710 | 5-(4-CH₃.C₆H₄)-1,2,4-thiadiazol-3-yl |
| 1711 | 5-(3-OCH₃.C₆H₄)-1,2,4-thiadiazol-3-yl |
| 1712 | 5-(4-OCH₃.C₆H₄)-1,2,4-thiadiazol-3-yl |
| 1713 | 5-(4-NO₂—C₆H₄)-1,2,4-thiadiazol-3-yl |
| 1714 | 5-(3-NO₂—C₆H₄)-1,2,4-thiadiazol-3-yl |
| 1715 | 5-(4-CN—C₆H₄)-1,2,4-thiadiazol-3-yl |
| 1716 | 5-(3-CN—C₆H₄)-1,2,4-thiadiazol-3-yl |
| 1717 | 5-(3-CF₃.C₆H₄)-1,2,4-thiadiazol-3-yl |
| 1718 | 5-(4-CF₃.C₆H₄)-1,2,4-thiadiazol-3-yl |
| 1719 | 5-(4-C(CH₃)₃.C₆H₄)-1,2,4-thiadiazol-3-yl |
| 1720 | 5-(2-Cl—C₆H₄)-1,2,4-thiadiazol-3-yl |
| 1721 | 5-(3-Cl—C₆H₄)-1,2,4-thiadiazol-3-yl |
| 1722 | 5-(4-Cl—C₆H₄)-1,2,4-thiadiazol-3-yl |
| 1723 | 5-(2-Br—C₆H₄)-1,2,4-thiadiazol-3-yl |
| 1724 | 5-(3-Br—C₆H₄)-1,2,4-thiadiazol-3-yl |
| 1725 | 5-(4-Br—C₆H₄)-1,2,4-thiadiazol-3-yl |
| 1726 | 5-(2-F—C₆H₄)-1,2,4-thiadiazol-3-yl |
| 1727 | 5-(3-F—C₆H₄)-1,2,4-thiadiazol-3-yl |
| 1728 | 5-(4-F—C₆H₄)-1,2,4-thiadiazol-3-yl |
| 1729 | 5-(2,4-Cl₂—C₆H₃)-1,2,4-thiadiazol-3-yl |
| 1730 | 5-(2,5-Cl₂—C₆H₃)-1,2,4-thiadiazol-3-yl |
| 1731 | 5-(2,6-Cl₂—C₆H₃)-1,2,4-thiadiazol-3-yl |
| 1732 | 5-(3,4-Cl₂—C₆H₃)-1,2,4-thiadiazol-3-yl |
| 1733 | 5-(2,4-F₂—C₆H₃)-1,2,4-thiadiazol-3-yl |
| 1734 | 5-(2,5-F₂—C₆H₃)-1,2,4-thiadiazol-3-yl |
| 1735 | 5-(2,6-F₂—C₆H₃)-1,2,4-thiadiazol-3-yl |
| 1736 | 5-(3,4-F₂—C₆H₃)-1,2,4-thiadiazol-3-yl |
| 1737 | 5-(2-Cl, 5-OCH₃.C₆H₃)-1,2,4-thiadiazol-3-yl |
| 1738 | 5-(2-Cl, 5-CH₃.C₆H₃)-1,2,4-thiadiazol-3-yl |
| 1739 | 5-(5-Cl, 2-OCH₃.C₆H₃)-1,2,4-thiadiazol-3-yl |
| 1740 | 5-(5-Cl, 2-CH₃.C₆H₃)-1,2,4-thiadiazol-3-yl |
| 1741 | 5-[2,5-(CH₃)₂—C₆H₃]-1,2,4-thiadiazol-3-yl |
| 1742 | 5-CH₃.1,3,4-thiadiazol-2-yl |
| 1743 | 5-CH(CH₃)₂-1,3,4-thiadiazol-2-yl |
| 1744 | 5-C(CH₃)₃.1,3,4-thiadiazol-2-yl |
| 1745 | 5-cyclopropyl-1,3,4-thiadiazol-2-yl |
| 1746 | 5-C₆H₅-1,3,4-thiadiazol-2-yl |
| 1747 | 5-(2-CH₃.C₆H₄)-1,3,4-thiadiazol-2-yl |
| 1748 | 5-(3-CH₃.C₆H₄)-1,3,4-thiadiazol-2-yl |
| 1749 | 5-(4-CH₃.C₆H₄)-1,3,4-thiadiazol-2-yl |

TABLE A-continued

| No. | R⁵ |
|---|---|
| 1750 | 5-(3-OCH$_3$.C$_6$H$_4$)-1,3,4-thiadiazol-2-yl |
| 1751 | 5-(4-OCH$_3$.C$_6$H$_4$)-1,3,4-thiadiazol-2-yl |
| 1752 | 5-(4-NO$_2$—C$_6$H$_4$)-1,3,4-thiadiazol-2-yl |
| 1753 | 5-(3-NO$_2$—C$_6$H$_4$)-1,3,4-thiadiazol-2-yl |
| 1754 | 5-(4-CN—C$_6$H$_4$)-1,3,4-thiadiazol-2-yl |
| 1755 | 5-(3-CN—C$_6$H$_4$)-1,3,4-thiadiazol-2-yl |
| 1756 | 5-(3-CF$_3$.C$_6$H$_4$)-1,3,4-thiadiazol-2-yl |
| 1757 | 5-(4-CF$_3$.C$_6$H$_4$)-1,3,4-thiadiazol-2-yl |
| 1758 | 5-(4-C(CH$_3$)$_3$.C$_6$H$_4$)-1,3,4-thiadiazol-2-yl |
| 1759 | 5-(2-Cl—C$_6$H$_4$)-1,3,4-thiadiazol-2-yl |
| 1760 | 5-(3-Cl—C$_6$H$_4$)-1,3,4-thiadiazol-2-yl |
| 1762 | 5-(2-Br—C$_6$H$_4$)-1,3,4-thiadiazol-2-yl |
| 1763 | 5-(3-Br—C$_6$H$_4$)-1,3,4-thiadiazol-2-yl |
| 1764 | 5-(4-Br—C$_6$H$_4$)-1,3,4-thiadiazol-2-yl |
| 1765 | 5-(2-F—C$_6$H$_4$)-1,3,4-thiadiazol-2-yl |
| 1766 | 5-(3-F—C$_6$H$_4$)-1,3,4-thiadiazol-2-yl |
| 1767 | 5-(4-F—C$_6$H$_4$)-1,3,4-thiadiazol-2-yl |
| 1768 | 5-(2,4-Cl$_2$—C$_6$H$_3$)-1,3,4-thiadiazol-2-yl |
| 1769 | 5-(2,5-Cl$_2$—C$_6$H$_3$)-1,3,4-thiadiazol-2-yl |
| 1770 | 5-(2,6-Cl$_2$—C$_6$H$_3$)-1,3,4-thiadiazol-2-yl |
| 1771 | 5-(3,4-Cl$_2$—C$_6$H$_3$)-1,3,4-thiadiazol-2-yl |
| 1772 | 5-(2,4-F$_2$—C$_6$H$_3$)-1,3,4-thiadiazol-2-yl |
| 1773 | 5-(2,5-F$_2$—C$_6$H$_3$)-1,3,4-thiadiazol-2-yl |
| 1774 | 5-(2,6-F$_2$—C$_6$H$_3$)-1,3,4-thiadiazol-2-yl |
| 1775 | 5-(3,4-F$_2$—C$_6$H$_3$)-1,3,4-thiadiazol-2-yl |
| 1776 | 5-(2-Cl, 5-OCH$_3$.C$_6$H$_3$)-1,3,4-thiadiazol-2-yl |
| 1777 | 5-(2-Cl, 5-CH$_3$.C$_6$H$_3$)-1,3,4-thiadiazol-2-yl |
| 1778 | 5-(5-Cl, 2-OCH$_3$.C$_6$H$_3$)-1,3,4-thiadiazol-2-yl |
| 1779 | 5-(5-Cl, 2-CH$_3$.C$_6$H$_3$)-1,3,4-thiadiazol-2-yl |
| 1780 | 5-[2,5-(CH$_3$)$_2$—C$_6$H$_3$]-1,3,4-thiadiazol-2-yl |
| 1781 | 1-CH(CH$_3$)$_2$-imidazol-4-yl |
| 1782 | 1-C(CH$_3$)$_3$.imidazol-4-yl |
| 1783 | 1-cyclopropl-imidazol-4-yl |
| 1784 | 1-C$_6$H$_5$-imidazol-4-yl |
| 1785 | 1-(2-CH$_3$.C$_6$H$_4$)-imidazol-4-yl |
| 1786 | 1-(3-CH$_3$.C$_6$H$_4$)-imidazol-4-yl |
| 1787 | 1-(4-CH$_3$.C$_6$H$_4$)-imidazol-4-yl |
| 1788 | 1-(3-OCH$_3$.C$_6$H$_4$)-imidazol-4-yl |
| 1789 | 1-(4-OCH$_3$.C$_6$H$_4$)-imidazol-4-yl |
| 1790 | 1-(4-NO$_2$—C$_6$H$_4$)-imidazol-4-yl |
| 1791 | 1-(3-NO$_2$—C$_6$H$_4$)-imidazol-4-yl |
| 1792 | 1-(4-CN—C$_6$H$_4$)-imidazol-4-yl |
| 1793 | 1-(3-CN—C$_6$H$_4$)-imidazol-4-yl |
| 1794 | 1-(3-CF$_3$.C$_6$H$_4$)-imidazol-4-yl |
| 1795 | 1-(4-CF$_3$.C$_6$H$_4$)-imidazol-4-yl |
| 1796 | 1-(4-C(CH$_3$)$_3$.C$_6$H$_4$)-imidazol-4-yl |
| 1797 | 1-(2-Cl—C$_6$H$_4$)-imidazol-4-yl |
| 1798 | 1-(3-Cl—C$_6$H$_4$)-imidazol-4-yl |
| 1799 | 1-(4-Cl—C$_6$H$_4$)-imidazol-4-yl |
| 1800 | 1-(2-Br—C$_6$H$_4$)-imidazol-4-yl |
| 1801 | 1-(3-Br—C$_6$H$_4$)-imidazol-4-yl |
| 1802 | 1-(4-Br—C$_6$H$_4$)-imidazol-4-yl |
| 1803 | 1-(2-F—C$_6$H$_4$)-imidazol-4-yl |
| 1804 | 1-(3-F—C$_6$H$_4$)-imidazol-4-yl |
| 1805 | 1-(4-F—C$_6$H$_4$)-imtdazol-4-yl |
| 1806 | 1-(2,4-Cl$_2$—C$_6$H$_3$)-imidazol-4-yl |
| 1807 | 1-(2,5-Cl$_2$—C$_6$H$_3$)-imidazol-4-yl |
| 1808 | 1-(2,6-Cl$_2$—C$_6$H$_3$)-imidazol-4-yl |
| 1809 | 1-(3,4-Cl$_2$—C$_6$H$_3$)-imidazol-4-yl |
| 1810 | 1-(2,4-F$_2$—C$_6$H$_3$)-imidazol-4-yl |
| 1811 | 1-(2,5-F$_2$—C$_6$H$_3$)-imidazol-4-yl |
| 1812 | 1-(2,6-F$_2$—C$_6$H$_3$)-imidazol-4-yl |
| 1813 | 1-(3,4-F$_2$—C$_6$H$_3$)-imidazol-4-yl |
| 1814 | 1-(2-Cl, 5-OCH$_3$.C$_6$H$_3$)-imidazol-4-yl |
| 1815 | 1-(2-Cl, 5-CH$_3$.C$_6$H$_3$)-imidazol-4-yl |
| 1816 | 1-(5-Cl, 2-OCH$_3$.C$_6$H$_3$)-imidazol-4-yl |
| 1817 | 1-(5-Cl, 2-CH$_3$.C$_6$H$_3$)-imidazol-4-yl |
| 1818 | 17 [2,5-(CH$_3$)$_2$—C$_6$H$_3$]-imidazol-4-yl |

The compounds I are suitable for controlling harmful fungi and animal pests.

Depending on their chemical and physical properties, they can be formulated with customary formulation auxiliaries, i.e. those conventionally used by a skilled worker. The products of this procedure are also termed "compositions".

Examples of suitable formulation auxiliaries are solid or liquid carriers, surfactants and tackifiers.

Liquid carriers are to be understood as meaning liquid solvents such as water and organic solvents, the latter acting as an auxiliary solvent, above all when the solvent used is water. Organic solvents which can be used are: aromatics such as xylene, toluene and alkylnaphthalenes, chlorinated aromatics or chlorinated aliphatic hydrocarbons such as chlorobenzenes, chloroethylenes and methylene chloride, aliphatic hydrocarbons such as cyclohexane and paraffins, e.g. mineral oil fractions, alcohols such as butanol, isobutanol, cyclohexanol and glycol and the corresponding ethers and esters, ketones such as acetone, methyl ethyl ketone, methyl isobutyl ketone and cyclohexanone, aprotic dipolar solvents such as dimethylformamide, N-methyl-2-pyrrolidone and dimethyl sulfoxide.

Examples of suitable solid carriers are: ground natural minerals and mineral earths such as silicas, silicates, kaolins, clays, bole, loess, talc, chalk, limestone, lime, dolomite, magnesium oxide, quartz, attapulgite, montmorillonite and diatomaceous earth; ground synthetic minerals such as highly-disperse silica or meals of synthetic alumina and of synthetic silicates. Examples of solid carriers which are especially suitable for granules are: crushed and fractionated natural rocks such as calcite, marble, pumice, sepiolite; synthetic granules of inorganic and organic meals; granules of organic materials such as sawdust, coconut shells, maize cobs or tobacco stalks.

Suitable surfactants are non-ionic and anionic emulsifiers/foam-formers and dispersants:

fatty acid polyoxyethylene esters such as lauryl alcohol polyoxyethylene ether acetate, alkyl polyoxyethylene ethers or alkyl polyoxypropylene ethers, such as of isotridecyl alcohol, and fatty alcohol polyoxyethylene ethers, alkylaryl alcohol polyoxyethylene ethers such as octylphenyl polyoxyethylene ether, tributylphenyl polyoxyethylene ether, ethoxylated isooctylphenol, octylphenol or nonylphenol or castor oil, sorbitol esters, arylsulfonic acids, alkylsulfonic acids, alkylsulfuric acids, alkali metal, alkaline earth metal and ammonium salts of arylsulfonic acids, e.g. ligno-, phenol-, naphthalene- and dibutylnaphthalenesulfonic acid, of alkylsulfonic acids, of alkylarylsulfonic acids, of alkylsulfuric acids, of lauryl ether sulfuric acids and of fatty alcohol sulfuric acids, of fatty acids, of sulfated hexa-, hepta- and octadecanols and of fatty alcohol glycol ethers, condensates of sulfonated naphthalene and its derivatives with formaldehyde, condensates of naphthalenesulfonic acids with phenol and formaldehyde, protein hydrolysates and in particular as dispersants: lignin-sulfite waste liquors and methylcellulose.

Examples of suitable tackifiers are: carboxymethylcellulose; natural and synthetic polymers in the form of powders, granules or latices such as gum arabic, polyvinyl alcohol, polyvinyl acetate, natural phospholipids such as cephalins and lecithins, synthetic phospholipids.

Furthermore, the compositions may comprise one or more representatives of the following groups of substances: colorants, other known active ingredients, trace nutrients and other additives. Suitable colorants are, for example, inorganic pigments such as iron oxide, titanium oxide, Prussian Blue, furthermore organic pigments such as alizarin, azo and metal phthalocyanin colorants. Other known active ingredients are to be understood as meaning, for example, other fungicides and also insecticides, acaricides, herbicides and growth regulators. Examples of trace nutrients are salts of iron, manganese, boron, copper, cobalt, molybdenum and zinc. Substances which are suitable as other additives are, for example, mineral oils and vegetable oils.

In addition, the compositions can be mixed with other components which are important under practice conditions, such as fertilizers or other finished compositions comprising active ingredients.

Depending on the chemical and physical properties of the substances employed, the compositions are prepared in a manner known per se, for example by mixing, concomitant grinding, spraying on, extruding, granulating or dissolving in water, the latter, if required, with the aid of an organic solvent. Powders, materials for spreading and dusts can be obtained for example by mixing or concomitantly grinding the compounds I together with a solid carrier.

Depending on the substances employed, the compositions are, for example, solutions, emulsions, suspensions, powders, foams, pastes, granules, aerosols or microencapsulations in polymeric substances or in coating compositions for seed.

For use, the compositions, which are generally commercially available as concentrates, are, if required, dissolved, diluted and the like in the customary manner, normally using water in the case of wettable powders, water-dispersible granules, emulsifiable concentrates, dispersions and in some cases also microgranules. Preparations in the forms of dusts and granulated preparations, and also sprayable solutions, are in most cases not diluted further with other inert substances prior to use.

The compositions are applied in a manner known per se, such as by spraying, atomizing, dusting, spreading or pouring. As a rule, the plants are sprayed or dusted with the compositions. Alternatively, or additionally, the seeds of the plants are treated in a manner known per se.

Examples of such preparations are:

I. a solution of 90 parts by weight of a compound I according to the invention and 10 parts by weight of N-methyl-2-pyrrolidone, which is suitable for use in the form of microdrops;

II. a mixture of 20 parts by weight of a compound I according to the invention, 80 parts by weight of xylene, 10 parts by weight of the adduct of 8 to 10 mol of ethylene oxide and 1 mol of oleic acid N-monoethanolamide, 5 parts by weight of calcium dodecylbenzenesulfonate, 5 parts by weight of the adduct of 40 mol of ethylene oxide and 1 mol of castor oil: a dispersion is obtained by finely distributing the solution in water;

III. an aqueous dispersion of 20 parts by weight of a compound I according to the invention, 40 parts by weight of cyclohexanone, 30 parts by weight of isobutanol, 20 parts by weight of the adduct of 40 mol of ethylene oxide and 1 mol of castor oil;

IV. an aqueous dispersion of 20 parts by weight of a compound I according to the invention, 25 parts by weight of cyclohexanol, 65 parts by weight of a mineral oil fraction of boiling point 210 to 280° C. and 10 parts by weight of the adduct of 40 mol of ethylene oxide and 1 mol of castor oil;

V. a mixture, ground in a hammer mill, of 80 parts by weight of a compound I according to the invention, 3 parts by weight of sodium diisobutylnaphtalene-1-sulfonate, 10 parts by weight of the sodium salt of a lignosulfonic acid, sulfite waste liquor and 7 parts by weight of pulverulent silica gel: a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 92 parts by weight of pulverulent silica gel and 8 parts by weight of paraffin oil which had been sprayed onto the surface of this silica gel; this formulation imparts good adhesion to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a paraffinic mineral oil.

If the compounds I are applied as such, the most important factor is that they are finely distributed.

The compounds I and the compositions according to the invention are distinguished by an outstanding activity against a broad spectrum of harmful fungi (phytopathogenic fungi), in particular from the classes of the Ascomycetes, Basidiomycetes, Deuteromycetes and Phycomycetes.

Some of them act systemically and can be employed as foliar- and soil-acting fungicides.

They are especially important for controlling a large number of fungi on a variety of crop plants such as wheat, rye, barley, oats, rice, maize, grass, cotton, soybeans, coffee, sugar cane, grapevines, fruit species, ornamentals and vegetables such as cucumbers, beans and cucurbits, and on the seeds of these plants.

Compounds I and their salts and the compositions according to the invention are applied by treating the harmful fungi, their environment, or the seeds, plants, areas, materials or spaces to be protected against fungal infection, with a fungicidally active amount of the compositions or of the compounds I or the salts thereof. Application can be effected before or after infection by the fungi.

Specifically, the compositions according to the invention and the compounds I are suitable for controlling the following plant diseases:

*Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, grapevines, ornamentals and vegetables, *Cercospora arachidicola* on peanuts, *Pseudocercosporella herpotri-* choides on wheat, barley, *Pyricularia oryzae* on rice, *Phytophthora infestans* on potatoes and tomatoes, Fusarium and Verticillium species on a variety of plants, *Plasmopara viticola* on grapevines, Pseudoperonospora species in hops and cucumbers, and Alternaria species on vegetables and fruit.

In general, the fungicidal compositions comprise from 0.1 to 95, preferably from 0.5 to 90, % by weight of active ingredient.

Depending on the nature of the desired effect, the application rates are from 0.01 to 2.0 kg of active ingredient per ha.

In the treatment of seed, amounts of from 0.001 to 0.1 g, preferably 0.01 to 0.05 g, of active ingredient are generally required per kilogram of seed. In the use form as fungicides, the compositions according to the invention can also be present together with other active ingredients, e.g. with herbicides, insecticides, growth regulators, fungicides or else with fertilizers.

In many cases, a mixture with fungicides results in a widened fungicidal spectrum of action The following list of fungicides together with which the compounds according to the invention can be used concomitantly is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide; nitro derivatives, such as dinitro(1-methylheptyl)phenyl crotonate, 2-sec-butyl-4,6-dinitrophenyl 3,3-dimethyl acrylate, 2-sec-butyl-4,6-dinitrophenyl isopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethylphthalimidophosphonothioate, 5-amino-1-[bis(dimethylamino) phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis(2,2,2-trichloroethyl)formamide, 1-(3,4-dichloroanilino)-1-formylamino-2,2,2-trichloroethane, 2,6-dimethyl-N-tridecyl-morpholine and its salts, 2,6-dimethyl-N-cyclododecylmorpholine and its salts, N-[3-(p-tert-butylphenyl)-2-methylpropyl]-cis-2,6-dimethyl-morpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-buyl-2-dimethylamino-4-hydoxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidin, 3-[3,5-dichlorophenyl(-5-methyl-5-methoxy-methyl]-1,3-oxazolidine-2,4-dione [sic], 3-(3,5-dichlorophenyl)-1-isopropylcarbamoylhydantoin,N-(3,5-dichlorophenyl)-1,2-dimethylcyclopropane-1,2-dicarboximide,2-cyano-[N-(ethylaminocarbonyl)-2-methoximin] acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)methyl)-1H-1,2,4-triazole, strobilurins such as methyl E-methoximino-[α-(o-tolyloxy)-o-tolyl]-acetate, methyl E-2-{2-[6-(2-cyanophenoxy)-pyrimidin-4-yloxy]phenyl}-3-methoxyacrylate, N-methyl E-methoximino-[α-(2-phenoxyphenyl)]-acetamide, N-methyl E-methoximino-[α-(2, 5-dimethylphenoxy)-o-tolyl]-acetamide, anilinopyrimidines such as N-(4,6-dimethylpyrimidin-2-yl)aniline, N-[4-methyl-6-(1-propynyl)pyrimidin-2-yl]-aniline, N-(4-methyl-6-cyclopropylpyrimidin-2-yl)-aniline, phenylpyrrols such as 4-(2,2-difluoro-1,3-benzodioxol-4-yl)-pyrrole-3-carbonitrile, cinnamamides such as 3-(4-chlorophenyl)-3-(3,4-dimethoxyphenyl)-acryloylmorpholine, (2RS, 3SR)-1-[3-(2-chlorophenyl)-2-[4-fluorophenyl] oxiran-2-ylmethyl]-1H-1,2,4-triazole.

The compounds of the formula I are, moreover, suitable for effectively controlling animal pests, above all from the classes of the insects, arachnids and nematodes. They can be employed as pesticides in crop protection and in the hygiene, stored-product and veterinary sectors.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheima-* tobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.

From the order of the beetles (Coleoptera), for example, Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.

From the order of the dipterans (Diptera), for example, Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.

From the order of thrips (Thysanoptera), for example, Frankliniella fusca, Frankliniella occidentalis, Frankliniella tritici, Scirtothrips citri, Thrips oryzae, Thrips palmi, Thrips tabaci.

From the order of the hymenopterans (Hymenoptera), for example, Athalia rosae, Atta cephalotes, Atta sexdens, Atta texana, Hoplocampa minuta, Hoplocampa testudinea, Monomorium pharaonis, Solenopsis geminata, Solenopsis inyicta.

From the order of the heteropterans (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.

From the order of the homopterans (Homoptera), for example, Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparyata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.

From the order of the termites (Isoptera), for example, Calotermes flavicollis, Leucotermes flavipes, Reticulitermes lucifugus, Termes natalensis.

From the order of the orthopterans (Orthoptera), for example, Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.

From the class of the Arachnoidea, for example, arachnids (Acarina) such as Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.

From the class of the nematodes, for example, root knot nematodes, e.g. Meloidogyne hapla, Meloidogyne incognita, Meloidogyne javanica, cyst-forming nematodes, e.g. Globodera rostochiensis, Heterodera avenae, Heterodera glycines, Heterodera schachtii, Heterodera trifolii, stem eelworms and foliar nematodes, e.g. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curyitatus, Pratylenchus goodeyi.

In the ready-to-use preparations, the concentrations of active ingredient can be varied within substantial ranges.

In general, they are between 0.0001 and 10%, preferably between 0.01 and 1%.

The active ingredients can also be used very successfully in the ultra-low volume method (ULV), it being possible to apply formulations with over 95% by weight of active ingredient, or even the active ingredient without additives.

Under the conditions in the open, the rate of application of active ingredient for controlling pests is from 0.1 to 2.0, preferably 0.2 to 1.0 kg/ha.

Synthesis examples

The protocols given in the synthesis examples below can be used for obtaining other representatives of the compounds I by altering the starting compounds. The chemical shifts (δ [ppm]) of the $^1$H NMR spectra was measured against tetramethylsilane (br=broad signal, s=singlet, d=doublet, m=multiplet).

EXAMPLE 1

Methyl (E,E)-2-methoxyimino-2-(2'-[{1"-methyl, 1"-benzoyl}iminooxymethyl]phenyl)acetate

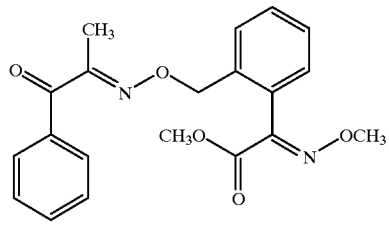

27 g of sodium methoxide solution (30% strength in methanol; 0.15 mol) were added to a solution of 24.5 g (0.15 mol) of 1-phenyl-1,2-propanedione 2-E-oxime and 43 g (0.15 mol) of methyl E-2-methoxyimino-2-[(2'-bromomethyl) phenyl]acetate (cf. EP-A 400 417) in 150 ml of N,N-dimethylformamide and the mixture was stirred for 2 h at room temperature. The reaction mixture was poured into cold dilute hydrochloric acid and then extracted with methyl tert-butyl ether, the organic phase was washed with water and dried over $Na_2SO_4$, and the solvent was distilled off. After triturating the residue with methanol, 42.7 g of the title compound were obtained as a white powder of melting point 94–95° C.

$^1$H NMR (CDCl$_3$): 2.09 (s,3H); 3.81 (s,3H); 4.01 (s,3H); 5.13 (s,2H); 7.18–7.79 (m,9H).

EXAMPLE 2

N-Monomethyl-(E,E)-2-methoxyimino-2-(2'-[{1"-methyl, 1"-benzoyl}iminooxymethyl]phenyl)acetamide

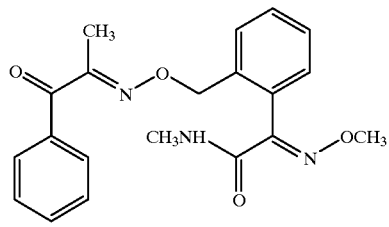

42.7 g (0.12 mol) of the product of Example 1 were dissolved in 400 ml of THF, 100 ml of 40% strength by weight of aqueous monomethylamine solution were added, and the mixture was left to stand for 16 hours at room temperature. 2 N hydrochloric acid was then added, the mixture was extracted with methyl tert-butyl ether, the organic phase was washed with water and dried over sodium sulfate, and the solvent was removed. 34.7 g of the title compound remained as the residue in the form of a white powder of melting point 114–118° C.

$^1$H NMR (CDCl$_3$): 2.09 (s,3H); 2.85 (d,3H); 3.90 (s,3H); 5.15 (s,2H); 6.71 (s,br,1H); 7.19–7.80 (m,9H).

EXAMPLE 3

N-Monomethyl-(E,E,E)-2-methoxyimino-2-[2'-[[1"-methyl, 1"-[(1'"-cyanoimino, 1'"-phenyl)methyl]] iminooxymethyl]phenyl]acetamide

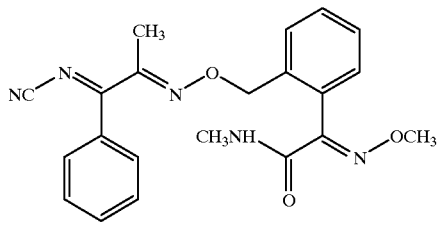

5.0 g (27 mmol) of bis(trimethylsilyl)carbodiimide were added to a solution of 2.5 g (6.8 mmol) of the product of Example 2 in 50 ml of methylene chloride, and the mixture was stirred for 60 hours at room temperature with the exclusion of moisture. The mixture was subsequently treated with 5.1 g (27 mmol) of titanium tetrachloride, and the mixture was again stirred for 16 hours at room temperature. Then, the reaction batch was poured into ice-water and extracted with methylene chloride. The organic phase was washed with water and dried over $Na_2SO_4$, and the solvent was distilled off. 1.8 g of the title compound remained as the residue in the form of a colorless oil.

$^1$H NMR (CDCl$_3$): 2.12 (s,3H); 2.90 (d,3H); 3.91 (s,3H); 5.10 (s,2H); 6.77 (s,br,1H); 7.15–7.56 (m,9H).

IR (KBr): 3361, 2182, 1661, 1564, 1555, 1038, 1002, 996, 978, 704 cm$^{-1}$

EXAMPLE 4

Methyl (E,E)-2-methoxyimino-2-{2'-[(1"-methyl, 1"-(4'"-chlorobenzoyl)]-iminooxymethyl}phenyl]acetate

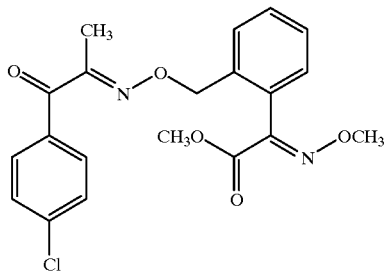

6.3 g of sodium methoxide solution (30% strength in methanol; 35 mmol) were added to a solution of 5.6 g (35 mmol) of 1-(4'-chlorophenyl)-1,2-propanedione 2-E-oxime and 10 g (35 mmol) of methyl E-2-methoxyimino-2-[(2-'bromomethyl)phenyl]acetate [cf. EP-A 400 417] in 150 ml of N,N-dimethylformamide and the mixture was stirred for 16 hours at room temperature (approximately 25° C.). The reaction mixture was poured into cold dilute hydrochloric acid and extracted with tert-butyl methyl ether. The organic phase was washed with water and subsequently dried and concentrated under reduced pressure. This gave 12.3 g of the title compound as a pale yellow oil.

$^1$H NMR (CDCl$_3$): 2.07 (s,3H); 3.82 (s,3H); 4.01 (s,3H); 5.13 (s,2H); 7.17–7.71 (m,8H).

EXAMPLE 5

Methyl (E,E,E)-2-methoxyimino-2-{2'-[(1"-methyl, 1"-((1"'-cyanoimino, 1'"- (4'"-chlorophenyl))methyl)-iminooxymethyl}phenyl]acetate

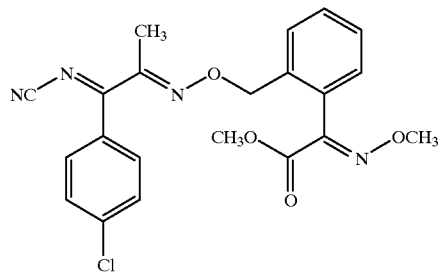

First, 9.2 g (49.7 mmol) of bis(trimethylsilyl) carbodiimide and subsequently 9.4 g of titanium tetrachloride were added to a solution of 5.0 g (12.4 mmol) of the product of Example 4 in 100 ml of methylene chloride, and the mixture was then stirred for 60 hours at room temperature (approximately 25° C.) with the exclusion of moisture. The reaction mixture was then poured into ice-water and extracted with methylene chloride. The organic phase was washed with water, dried and concentrated under reduced pressure. The resulting residue was chromatographed over a silica gel column (tert-butyl methyl ether/cyclohexane). This gave 1.7 g of the title compound as a colorless oil.

$^1$H NMR (CDCl$_3$): 2.10 (s,3H); 3.84 (s,3H); 4.00 (s,3H); 5.09 (s,2H); 7.15–7.48 (m,8H).

TABLE I (I)

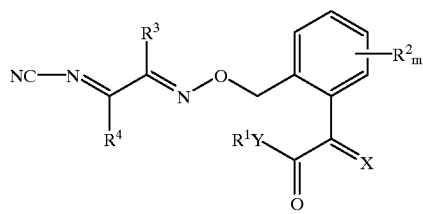

| No. | R$^1$ | Y | X | R$^2_m$ | R$^3$ | R$^4$ | Physical data [IR (cm$^{-1}$)] |
|---|---|---|---|---|---|---|---|
| I.1 | CH$_3$ | NH | NOCH$_3$ (E) | H | CH$_3$ | C$_6$H$_5$ | 3361, 2945, 2182, 1661, 1564, 1555, 1038, 1002, 996, 978, 704 (KBr) |
| I.2 | CH$_3$ | O | NOCH$_3$ (E) | H | CH$_3$ | 2-CF$_3$—C$_6$H$_4$ | 2960, 2200, 1728, 1319, 1224, 1168, 1127, 1069, 1035, 1015, 995, 768 (film) |
| I.3 | CH$_3$ | O | NOCH$_3$ (E) | H | CH$_3$ | 3-CF$_3$—C$_6$H$_4$ | 2950, 2200, 1728, 1570, 1318, 1221, 1201, 1169, 1129, 1072, 1051, 1020 (film) |
| I.4 | CH$_3$ | O | NOCH$_3$ (E) | H | CH$_3$ | 3-CN-C$_6$H$_4$ | 2955, 2187, 1727, 1584, 1222, 1202, 1067, 1047, 1020, 1000, 961 (KBr) |
| I.5 | CH$_3$ | O | NOCH$_3$ (E) | H | CH$_3$ | 4-CN—C$_6$H$_4$ | 2960, 2187, 1727, 1576, 1221, 1208, 1069, 1048, 1019, 999, 959 (film) |
| I.6 | CH$_3$ | O | NOCH$_3$ (E) | H | CH$_3$ | 4-C(CH$_3$)$_3$—C$_6$H$_4$ | 2964, 2185, 1726, 1572, 1222, 1112, 1070, 1018 (KBr) |
| I.7 | CH$_3$ | O | NOCH$_3$ (E) | H | CH$_3$ | 4-Cl—C$_6$H$_4$ | 2950, 2190, 1727, 1576, |

TABLE I-continued (I)

$$\text{NC-N=C(R}^3\text{)-C(R}^4\text{)=N-O-CH}_2\text{-C}_6\text{H}_4\text{(R}^2_m\text{)-C(=X)-C(=O)-YR}^1$$

| No. | R¹ | Y | X | R²ₘ | R³ | R⁴ | Physical data [IR (cm⁻¹)] |
|---|---|---|---|---|---|---|---|
| | | | | | | | 1557, 1220, 1205, 1092, 1069, 1047, 1015, 958 (film) |
| I.8 | CH₃ | NH | NOCH₃ (E) | H | CH₃ | 2-CF₃—C₆H₄ | 3350, 2930, 2180, 1673, 1569, 1528, 1316, 1175, 1131, 1071, 1035, 1002, 980 (film) |
| I.9 | CH₃ | NH | NOCH₃ (E) | H | CH₃ | 3-CF₃—C₆H₄ | 3290, 2940, 2180, 1646, 1563, 1323, 1316, 1181, 1172, 1127, 1040, 998, 980 (KBr) |
| I.10 | CH₃ | NH | NOCH₃ (E) | H | CH₃ | 4-C(CH₃)₃—C₆H₄ | 3350, 2965, 2184, 1676, 1606, 1572, 1549, 1528, 1038, 998, 979 (film) |
| I.11 | CH₃ | NH | NOCH₃ (E) | H | CH₃ | 4-Cl—C₆H₄ | 3360, 2930, 2185, 1674, 1575, 1555, 1528, 1092, 1037, 1013, 999, 980 (film) |
| I.12 | CH₃ | NH | NOCH₃ (E) | H | CH₃ | 3,5-Cl₂—C₆H₃ | 3350, 2930, 2175, 1667, 1563, 1527, 1316, 1188, 1038, 1005, 980, 798, 748 (film) |

Use examples

1. Example of the activity against harmful fungi

In the following experiments on the fungicidal activity of the compounds I, an emulsion was used which was composed of 10% by weight of the active ingredient and 90% by weight of a mixture of 70% by wt. of cyclohexanol, 20% by wt. of Nekanil® LN (Lutensol® AP6, wetting agent having emulsifying and dispersant action based on ethoxylated alkylphenols) and 10% by wt. of Emulphor® EL (Emulan® EL, emulsifier based on ethoxylated fatty alcohols).

The desired concentrations of active ingredients were adjusted by diluting this emulsion with water.

The comparison substance A was Compound 3.81 (WO-A 95/18,789, Table 3); the comparison substance B was Compound H-2 (WO-A 93/16,986, Table 1).

Use Example 1

Activity against powdery mildew of wheat

Leaves of wheat seedlings cv. "Frühgold", in pots, were sprayed with aqueous spray mixture comprising 10% by weight of active ingredient, 63% by weight of cyclohexanone and 27% by weight of emulsifier in the dry matter and, 24 hours after the spray coating had dried on, dusted with oidia (spores) of powdery mildew of wheat (Erysiphe graminis var. tritici). The test plants were subsequently placed in the greenhouse at from 20 to 22° C. and a relative atmospheric humidity of 75 to 80%. After 7 days, the extent of mildew development was determined visually.

In this test, the plants which had been treated with an aqueous preparation comprising 63 ppm of the compounds I.1, I.3, I.7, I.9, I.11 and I.12 showed a disease level of 15% and less, while the plants which had been treated with an equal amount of the compounds A and B, as well as the untreated plants, showed a disease level of 60%.

Use Example 2

Activity against *Plasmopara viticola*

Leaves of grapes cv. "Müller-Thurgau", in pots, were sprayed with aqueous spray mixture comprising 10% by weight of active ingredient, 63% of cyclohexanone and 27% by weight of emulsifier and dry matter. To be able to assess the duration of action of the active ingredient, the plants were placed in the greenhouse for 8 days, after the spray coating had dried on. Only then were the leaves infected with a zoospore suspension of *Plasmopara viticola* (downy mildew of grapevines). Then, the plants were first placed for 48 hours in a water-vapor-saturated chamber at 24° C. and subsequently for 5 days in a greenhouse at from 20 to 30° C. After this time, the plants were returned into the humid chamber for 16 hours to accelerate the eruption of sporangiophores. The extent of fungal eruption on the underside of the leaves was subsequently assessed visually.

In this test, a disease level of 15% and less was shown by the plants which had been treated with an aqueous preparation comprising 63 ppm of the compounds I.1, I.2, I.3, I.4, I.6, I.7, I.8, I.9, I.10 and I.11, while the plants which had been treated with the same amount of Compound A showed a disease level of 65%. The disease level of the untreated plants was 80%.

Use Example 3

Activity against *Pyricularia oryzae* (rice blast disease; protective)

Rice seedlings (variety: "Tai Nong 67") were sprayed to run-off point with the preparation of active ingredient (application rate: 63 ppm; formulation: 10% of active ingredient, 63% of cyclohexanone and 27% of emulsifier). After 24 hours, the plants were sprayed with an aqueous spore suspension of the fungus *Pyricularia oryzae* and kept for 6 days at 22–24° C. at a relative atmospheric humidity of 95–99%. The assessment was carried out visually. In this test, the plants which had been treated with the compounds I.1, I.3, I.4, 1.5, I.6, I.7 and I.10 showed a disease level of 15% and less, while the disease level of the untreated plants was 75%. The plants which had been treated with the comparison substances A and B showed disease levels of 65% and 40%, respectively.

2. Examples of the activity against animal pests

The activity of the compounds of the general formula I against animal pests was demonstrated by the following experiments:

The active ingredients were formulated a) as a 0.1% strength solution in acetone or b) as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols)

and diluted to give the desired concentration, using acetone in the case of a) and water in the case of b).

After the experiments had been concluded, in each case the lowest concentration at which the compounds still caused an 80–100% inhibition, or mortality, in comparison with untreated controls was determined (limit or minimal concentration).

We claim:

1. A cyanoiminooxime ether of the formula I

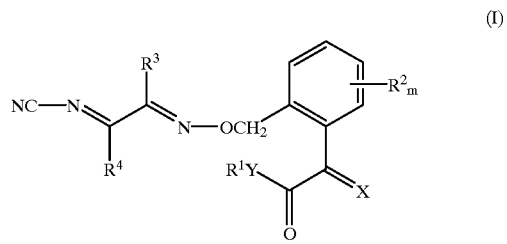

(I)

where the variables have the following meanings:

X is $NOCH_3$, $CHOCH_3$ or $CHCH_3$;

Y is O or NZ where Z is hydrogen or $C_1$–$C_4$-alkyl;

$R^1$ is hydrogen or $C_1$–$C_4$-alkyl;

$R^2$ is cyano, nitro, halogen, $C_1$–$C_4$-alkyl, trifluoromethyl or $C_1$–$C_4$-alkoxy;

m is 0, 1 or 2, the radicals $R^2$ being identical or different when m is 2;

$R^3$ is hydrogen, cyano, alkyl, haloalkyl, alkoxy or cycloalkyl;

$R^4$ is hydrogen, or is an unsubstituted or substituted alkyl, alkenyl, alkynyl, cycloalkyl, cycloalkenyl, heterocyclyl, aryl or hetaryl group, or a salt thereof.

2. A process for the preparation of a compound of the formula I defined in claim 1, which comprises reacting a benzyl compound of the formula II

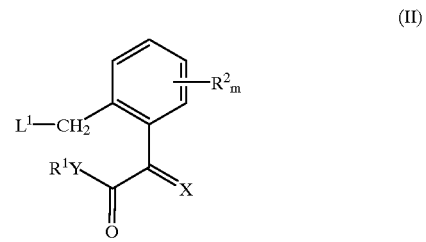

(II)

where $L^1$ is a nucleophilically exchangeable leaving group with a hydroxyimine of the formula III

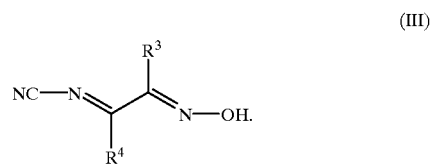

(III)

3. A process for the preparation of a compound of the formula I defined in claim 1, which comprises reacting a benzyl compound of the formula II

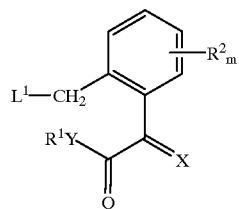

(II)

where $L^1$ is a nucleophilically exchangeable leaving group, with a carbonylhydroxyimino compound of the formula IV

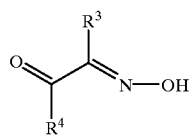

(IV)

to give a compound of the formula V

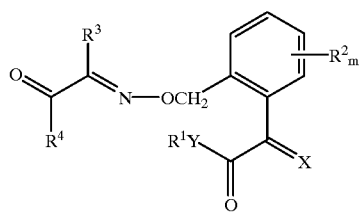

(V)

and subsequently reacting V with bis(trimethylsilyl) carbodiimide.

4. A composition suitable for controlling animal pests or harmful fungi, comprising an effective amount of a compound of the formula I or of a salt thereof as defined in claim 1, and at least one formulation auxiliary selected from the group consisting of solid or liquid carriers, surfactants and tackifiers.

5. The composition defined in claim 4 for controlling animal pests from the class of the insects, arachnids or nematodes.

6. A method of controlling animal pests or harmful fungi, which comprises treating the pests or harmful fungi, their environment, or the plants, or areas, to be protected against fungal infection, with an effective amount of a compound of the formula I or of a salt thereof as defined in claim 1.

7. A compound of the formula VII

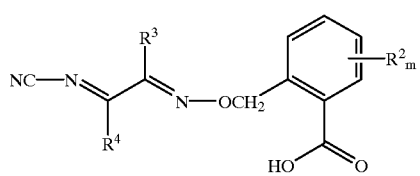

(VII)

wherein
$R^2$ is cyano, nitro, halogen, $C_1$–$C_4$-alkyl, trifluoromethyl or $C_1$–$C_4$-alkoxy;
m is 0, 1 or 2, the radicals $R^2$ being identical or different when m is 2;

$R^3$ is hydrogen, cyano, alkyl, haloalkyl, alkoxy of cycloalkyl; and
$R^4$ is hydrogen, or
is an unsubstituted or substituted alkyl, alkenyl, alkynyl, cycloalkyl, cycloalkenyl, heterocyclyl, aryl or hetaryl group.

8. A compound of the formula VIII

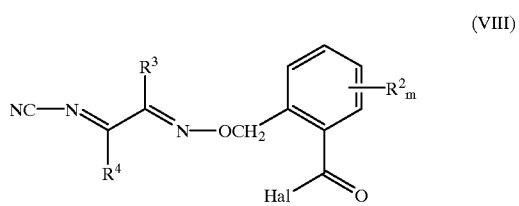

(VIII)

wherein Hal is halogen,
$R_2$ is cyano, nitro, halogen, $C_1$–$C_4$-alkyl, trifluoromethyl or $C_1$–$C_4$-alkoxy;
m is 0, 1 or 2, the radicals $R^2$ being identical or different when m is 2;
$R^3$ is hydrogen, cyanor alkyl, haloalkyl, alkoxy or cycloalkyl; and
$R^4$ is hydrogen, or
is an unsubstituted or substituted alkyl, alkenyl, alkynyl, cycloalkyl, cycloalkenyl, heterocyclyl, aryl or hetaryl group.

9. A compound of the formula IX

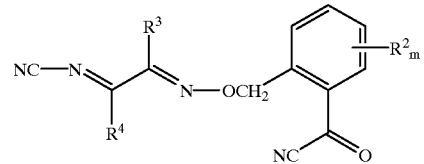

(IX)

wherein
$R^2$ is cyano, nitro, halogen, $C_1$–$C_4$-alkyl, trifluoromethyl or $C_1$–$C_4$-alkoxy;
m is 0, 1 or 2, the radicals $R^2$ being identical or different when m is 2;
$R^3$ is hydrogen, cyano, alkyl, haloalkyl, alkoxy or cycloalkyl; and
$R^4$ is hydrogen, or
is an unsubstituted or substituted alkyl, alkenyl, alkynyl, cycloalkyl, cycloalkenyl, heterocyclyl, aryl or hetaryl group.

10. A compound of the formula X

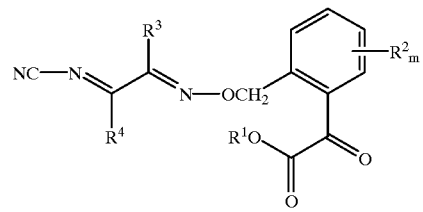

(X)

wherein
$R^2$ is cyano, nitro, halogen, $C_1$–$C_4$-alkyl, trifluoromethyl or $C_1$–$C_4$-alkoxy;

m is 0, 1 or 2, the radicals $R^2$ being identical or different when m is 2;

$R^3$ is hydrogen, cyano, alkyl, haloalkyl, alkoxy or cycloalkyl; and $R^4$ is hydrogen, or is an unsubstituted or substituted alkyl, alkenyl, alkynyl, cycloalkyl, cycloalkenyl, heterocyclyl, aryl or hetaryl group.

11. A compound of the formula XI

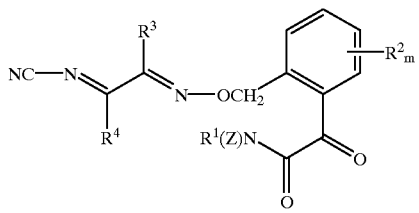

(XI)

wherein $R^2$ is cyano, nitro, halogen, $C_1$–$C_4$-alkyl, trifluoromethyl or $C_1$–$C_4$-alkoxy;

m is 0, 1 or 2, the radicals $R^2$ being identical or different when m is 2;

$R^3$ is hydrogen, cyano, alkyl, haloalkyl, alkoxy or cycloalkyl; and $R^4$ is hydrogen, or is an unsubstituted or substituted alkyl, alkenyl, alkynyl, cycloalkyl, cycloalkenyl, heterocyclyl, aryl or hetaryl group.

12. A compound of the formula XII

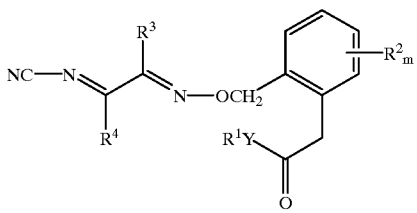

(XII)

wherein $R^2$ is cyano, nitro, halogen, $C_1$–$C_4$-alkyl, trifluoromethyl or $C_1$–$C_4$-alkoxy; m is 0, 1 or 2, the radicals $R^2$ being identical or different when m is 2;

$R^3$ is hydrogen, cyano, alkyl, haloalkyl, alkoxy or cycloalkyl; and $R^4$ is hydrogen, or is an unsubstituted or substituted alkyl, alkenyl, alkynyl, cycloalkyl, cycloalkenyl, heterocyclyl, aryl or hetaryl group.

* * * * *

UNITED STATES PATENT AND TRADEMARK OFFICE
CERTIFICATE OF CORRECTION

PATENT NO.: 6,063,813

DATED: May 16, 2000

INVENTOR(S): BAYER et al.

It is certified that error appears in the above-identified patent and that said Letters Patent is hereby corrected as shown below:

Col. 56, claim 7, line 1, "alkoxy of" should be --alkoxy or--.

Signed and Sealed this

Twentieth Day of March, 2001

Attest:

NICHOLAS P. GODICI

*Attesting Officer*     *Acting Director of the United States Patent and Trademark Office*